United States Patent
Jensen

(10) Patent No.: US 8,822,647 B2
(45) Date of Patent: Sep. 2, 2014

(54) METHOD AND COMPOSITIONS USING A CHIMERIC ANTIGEN RECEPTOR FOR ENHANCED ANTI-TUMOR EFFECTOR FUNCTIONING OF T CELLS

(75) Inventor: Michael Jensen, Pasadena, CA (US)

(73) Assignee: City of Hope, Duarte, CA (US)

(*) Notice: Subject to any disclaimer, the term of this patent is extended or adjusted under 35 U.S.C. 154(b) by 595 days.

(21) Appl. No.: 13/060,908

(22) PCT Filed: Aug. 26, 2009

(86) PCT No.: PCT/US2009/055029
§ 371 (c)(1),
(2), (4) Date: Jun. 22, 2011

(87) PCT Pub. No.: WO2010/025177
PCT Pub. Date: Mar. 4, 2010

(65) Prior Publication Data
US 2012/0148552 A1    Jun. 14, 2012

Related U.S. Application Data

(60) Provisional application No. 61/091,915, filed on Aug. 26, 2008.

(51) Int. Cl.
| | | |
|---|---|---|
| C07K 16/46 | (2006.01) | |
| C07K 19/00 | (2006.01) | |
| C12N 5/0783 | (2010.01) | |
| C12N 5/22 | (2006.01) | |
| C12N 15/63 | (2006.01) | |
| A61P 35/00 | (2006.01) | |

(52) U.S. Cl.
USPC .... 530/387.3; 530/350; 435/69.7; 435/320.1; 435/372.3; 424/93.21

(58) Field of Classification Search
None
See application file for complete search history.

(56) References Cited

U.S. PATENT DOCUMENTS

| | | |
|---|---|---|
| 5,359,046 A | 10/1994 | Capon et al. |
| 5,686,281 A | 11/1997 | Roberts |
| 6,410,319 B1 | 6/2002 | Raubitschek et al. |
| 7,070,995 B2 | 7/2006 | Jensen |
| 7,446,190 B2 | 11/2008 | Sadelain et al. |
| 7,514,537 B2 | 4/2009 | Jensen |
| 2002/0164794 A1 | 11/2002 | Wernet |
| 2003/0077249 A1 | 4/2003 | Bebbington et al. |
| 2003/0171546 A1 | 9/2003 | Jensen |

(Continued)

FOREIGN PATENT DOCUMENTS

| | | |
|---|---|---|
| JP | 2004528848 A | 9/2004 |
| WO | WO 00/23573 A2 | 4/2000 |
| WO | 02/088334 A1 | 11/2002 |
| WO | 2008095141 A2 | 8/2008 |

OTHER PUBLICATIONS

Wang et al (2007. Human Gene Therapy. 18: 712-725).*
Chang et al (2006. Journal of Immunotherapy. 29(6): 628).*

(Continued)

*Primary Examiner* — Zachary Howard
(74) *Attorney, Agent, or Firm* — Rothwell, Figg, Ernst & Manbeck P.C.

(57) ABSTRACT

Integration of costimulatory signaling domains within a tumor targeting chimeric antigen receptor (CAR), such as the IL13Rα2 specific IL13-zetakine (IL13ζ), enhances T cell-mediated responses against tumors even in the absence of expressed ligands for costimulatory receptors.

7 Claims, 31 Drawing Sheets

(56) References Cited

U.S. PATENT DOCUMENTS

| | | |
|---|---|---|
| 2005/0113564 A1 | 5/2005 | Campana et al. |
| 2006/0067920 A1 | 3/2006 | Jensen |
| 2007/0009469 A1 | 1/2007 | Kleinman et al. |

OTHER PUBLICATIONS

Altenschmidt et al., "Cytolysis of Tumor Cells Expressing in the NEU/ERBB-2, ERBB-3, and ERBB-4 Receptors by Genetically Targeted Naive T Lymphocytes" Clinical Cancer Research 2(6): 1001-1008, 1996.

Ashkenazi et al., "Immunoadhesins: An Alternative to Human Monoclonal Antibodies" Methods 8:104-115, 1995.

Bonnerot et al., "Intracellular signaling and endosomal trafficking of immunoreceptors: Shared effectors underlying MHC class II-restricted antigen presentation" Immunology Letters 57:1-4, 1997.

Campbell et al., "Totipotency Or Multipotentiality of Cultured Cells: Applications and Progress" Theriogenology 47:63-72, 1997.

Chang et al., "Transgene-enforced co-stimulation of CD4+ T cells leads to enhanced and sustained anti-tumor effector functioning" Cytotherapy, pp. 1-14, 2007.

Debinski et al., "Human Glioma Cells Overexpress Receptors for Interleukin 13 and are Extremely Sensitive to a Novel Chimeric Protein Composed of Interleukin 13 and Pseudomonas Exotoxin" Clinical Cancer Res. 1:1253-1258, 1995.

Debinski et al., "Novel Anti-Brain Tumor Cytotoxins Specific for Cancer Cells," Nature Biotechnology 16:449-453, 1998.

Debinski et al., "Receptor for Interleukin 13 is a Marker and Therapeutic Target for Human High-Grade Gliomas," Clinical Cancer Res. 5:985-990, 1999.

Debinski et al., "Receptor for Interleukin 13 is Abundantly and Specifically Over-Expressed in Patients with Glioblastoma Multiforme" Int. J. Oncology 15:481-486, 1999.

Debinski et al., "Retargeting 13 for Radioimmunodetection and Radioimmunotherapy of Human High-Grade Gliomas" Clinical Cancer Res. 5:3143s-3147s, 1999 (suppl).

Debinski et al., "Novel Way to Increase Targeting Specificity to a Human Glioblastoma-Associated Receptor for Interleukin 13" Int. J. Cancer 76:547-551, 1998.

Debinski "Expression of a Restrictive Receptor for Interleukin 13 is associated with Glial Transformation" J. Neuro-Oncology 48:103-111, 2000.

Ehtesham et al. "Recent Progress in Immunotherapy for Malignant Glioma: Treatment Strategies and Results From Clinical Trials" Cancer Control 11(3):192-207, 2004.

Jensen et al., "CD20 is a Molecular Target for scFvFc:zeta Receptor Redirected T Cells: Implications for Cellular Immunotherapy of CD20+ Malignancy" Biol. Blood Marrow Transplant 4:75-83, 1998.

Joshi et al., "Interleukin-13 Receptorα Chain: A Novel Tumor-Associated Transmembrane Protein in Primary Explants of Human Malignant Gliomas" Cancer Res. 60:1168-1172, 2000.

Kahlon et al., "Specific Recognition and Killing of Glioblastoma Multiforme by Interleukin 13-Zetakine Redirected Cytolytic T Cells" Cancer Res. 64:9160-9166, 2004.

Kahlon et al., "Redirecting T lymphocyte antigen specificity via engineered zetakine immonoreceptors: development of a prototype construct specific for the tumor-restricted IL-13alpha2 receptor" Molecular Therapy 3(5):S374, AB, 2001.

Kahlon et al., "The IL-13 zetakine chimeric immunoreceptor: a novel approach to genetically engineer T cells for glioma immunotherapy," Neuro-Oncology, 3(4):315-316, 2001.

Lazovic et al., "Imaging Immune Response In vivo: Cytolytic Action of Genetically Altered T Cells Directed to Glioblastoma Multiforme" Clin. Cancer Res. 14(12):3832-3839, 2008.

Liu et al., "Interleukin-13 Sensitivity and Receptor Phenotypes of Human Glial Cell Lines: Non-Neoplastic Glia and Low-Grade Astrocytoma Differ from Malignant Glioma" Cancer Immunol. Immunother. 49:319-324, 2000.

Melero et al., "Amplification of tumor immunity by gene transfer of the co-stimulatory 4-1BB ligand: synergy with the CD28 co-stimulatory pathway" Eur. J. Immunol. 28:1116-1121, 1998.

Minty et al., "Interleukin-13 is a New Human Lymphokine Regulating Inflammatory and Immune Responses" Nature 362:248-240, 1993.

Mintz et al., "Cancer Genetics/Epigenetics and the X Chromosome: Possible New Links for Malignant Glioma Pathogenesis and Immune-Based Therapies" Crit. Rev. Oncogenesis 11(1):77-95, 2000.

Moeller et al., "A Functional Role for CD28 Costimulation in Tumor Recognition by Single-Chain Receptor-Modified T Cells" Cancer Gene Therapy 11:371-379, 2004.

Murata et al., "Structure of IL-13 Receptor: Analysis of Subunit Composition in Cancer and Immune Cells" Biochem. Biophys. Res. Comm. 238(1):90-94, 1997.

Niederman et al., "Antitumor Activity of Cytotoxic T Lymphycyte Engineered to Target Vascular Endothelial Growth Factor Receptors" PNAS 99(10):7009-7014, 2002.

Obiri et al., "The IL-13 Receptor Structure Differs on Various Cell Types and May Share More than One Component With IL-4 Receptor" J. Immunol. 158:756-764, 1997.

Stastny et al., "Medulloblastomas Expressing IL13Rα2 are Targets for IL13-zetakine+ Cytolytic Cells," J. Pediatr. Hematol. Oncol. 29(10):669-677, 2007.

Thompson et al., "Mutants of Interleukin-13 with Altered Reactivity Toward Interleukin-13 Receptors" J. Biol. Chem. 274(42):29944-29950, 1999.

Xu et al., "Targeting and Therapy of Carcinoembryonic Antigen-Expressing Tumors in Transgenic Mice with an Antibody-Interleukin 2 Fusion Protein" Cancer Res. 60:4475-4484, 2000.

Yamasaki et al., "Specific Adoptive Immunotherapy of Malignant Glioma with Long-Term Cytotoxic T Lymphocyte Line Expanded in T-Cell Growth Factor" Experimental Study and Future Prospects, Neurosurg. Rev. 7:37-54, 1984.

Finney, H.M., "Chimeric Receptors Providing Both Primary and Costimulatory Signaling in T Cells from a Single Gene Product," Journal of Immunology, (1998), vol. 161, pp. 2791-2797, 9 pages.

Finney, H.M., "Activation of Resting Human Primary T Cells with Chimeric Receptors: Costimulation from CD28, Inducible Costimulator, CD134, and CD137 in Series with Signals from the TCRζ Chain," Journal of Immunology, (2004), vol. 172, pp. 104-113, 12 pages.

English Translation of Japanese Office Action, JP Application No. 2011-525168, Mailing Date: Feb. 28, 2014, 12 pages.

* cited by examiner

FIG. 2

```
            IL13P1
      ---------------------------------------------------->
            M  A  L  L  L  T  T  V  I  A  L  T  C  L  G  G  F
  1   TATGAATTCA TGGCCTTGCT GTTGACCACG GTCATTGCTC TCACTTGCCT TGGCGGCTTT
      ATACTTAAGT ACCGGAACGA CAACTGGTGC CAGTAACGAG AGTGAACGGA ACCGCCGAAA
            IL13P1
      <----------------------------------------------------
                                                IL13P2
                                        ---------------------------->
            A  S  P  G  P  V  P  P  S  T  A  L  R  Y  L  I  E  E  L  V
 61   GCCTCCCCAG GGCCTGTGCC TCCTCTACA GCCCTCAGGT ACCTCATTGA GGAGCTGGTC
      CGGAGGGGTC CCGGACACGG AGGAGATGT CGGGAGTCCA TGGAGTAACT CCTCGACCAG

N  I  T  Q  N  Q  K  A  P  L  C  N  G  S  M  V  W  S  I  N
121   AACATCACCC AGAACCAGAA GGCTCCGCTC TGCAATGGCA GCATGGTATG GAGCATCAAC
      TTGTAGTGGG TCTTGGTCTT CCGAGGCGAG ACGTTACCGT CGTACCATAC CTCGTAGTTG
                                         IL13P2
                                    <--------------------------------
                                                IL13P3
                                        ---------------------------->
            L  T  A  G  M  Y  C  A  A  L  E  S  L  I  N  V  S  G  C  S
181   CTGACAGCTG GCATGTACTG TGCAGCCCTG GAATCCCTGA TCAACGTGTC AGGCTGCAGT
      GACTGTCGAC CGTACATGAC ACGTCGGGAC CTTAGGGACT AGTTGCACAG TCCGACGTCA

A  I  E  K  T  Q  R  M  L  S  G  F  C  P  H  K  V  S  A  G
241   GCCATCGAGA AGACCCAGAG GATGCTGAGC GGATTCTGCC CGCACAAGGT CTCAGCTGGG
      CGGTAGCTCT TCTGGGTCTC CTACGACTCG CCTAAGACGG GCGTGTTCCA GAGTCGACCC
            IL13P3
      <----------------------------------------------------
            IL13P4
      ---------------------------------------------------->
            Q  F  S  S  L  H  V  R  D  T  K  I  E  V  A  Q  F  V  K  D
301   CAGTTTTCCA GCTTGCATGT CCGAGACACC AAAATCGAGG TGGCCCAGTT TGTAAAGGAC
      GTCAAAAGGT CGAACGTACA GGCTCTGTGG TTTTAGCTCC ACCGGGTCAA ACATTTCCTG
            IL13P4
      <----------------------------------------------------
                                IL13P5
                           --------------------------------
                           IL13P5
            L  L  L  H  L  K  K  L  F  R  E  G  R  F  N  *      (SEQ ID NO:1)
361   CTGCTCTTAC ATTTAAAGAA ACTTTTTCGC GAGGGACGTT TCAACTGAGG ATCGA  (SEQ ID NO:2)
      GACGAGAATG TAAATTTCTT TGAAAAAGCG CTCCCTGCAA AGTTGACTCC TAGCT  (SEQ ID NO:3)
```

FIG. 3A

```
            M  L  L  L  V  T  S  L  L  L  C  E  L
  1  ATCTCTAGAG CCGCCACCAT GCTTCTCCTG GTGACAAGCC TTCTGCTCTG TGAGTTACCA
     TAGAGATCTC GGCGGTGGTA CGAAGAGGAC CACTGTTCGG AAGACGAGAC ACTCAATGGT

H  P  A  F  L  L  I  P  G  P  V  P  P  S  T  A  L  R  Y  L
 61  CACCCAGCAT TCCTCCTGAT CCCAGGCCCT GTGCCTCCCT CTACAGCCCT CAGGTACCTC
     GTGGGTCGTA AGGAGGACTA GGGTCCGGGA CACGGAGGGA GATGTCGGGA GTCCATGGAG

I  E  E  L  V  N  I  T  Q  N  Q  K  A  P  L  C  N  G  S  M
121  ATTGAGGAGC TGGTCAACAT CACCCAGAAC CAGAAGGCTC CGCTCTGCAA TGGCAGCATG
     TAACTCCTCG ACCAGTTGTA GTGGGTCTTG GTCTTCCGAG GCGAGACGTT ACCGTCGTAC

V  W  S  I  N  L  T  A  G  M  Y  C  A  A  L  E  S  L  I  N
181  GTATGGAGCA TCAACCTGAC AGCTGGCATG TACTGTGCAG CCCTGGAATC CCTGATCAAC
     CATACCTCGT AGTTGGACTG TCGACCGTAC ATGACACGTC GGGACCTTAG GGACTAGTTG

V  S  G  C  S  A  I  E  K  T  Q  R  M  L  S  G  F  C  P  H
241  GTGTCAGGCT GCAGTGCCAT CGAGAAGACC CAGAGGATGC TGAGCGGATT CTGCCCGCAC
     CACAGTCCGA CGTCACGGTA GCTCTTCTGG GTCTCCTACG ACTCGCCTAA GACGGGCGTG

K  V  S  A  G  Q  F  S  S  L  H  V  R  D  T  K  I  E  V  A
301  AAGGTCTCAG CTGGGCAGTT TTCCAGCTTG CATGTCCGAG ACACCAAAAT CGAGGTGGCC
     TTCCAGAGTC GACCCGTCAA AAGGTCGAAC GTACAGGCTC TGTGGTTTTA GCTCCACCGG

Q  F  V  K  D  L  L  L  H  L  K  K  L  F  R  E  G  R  F  N
361  CAGTTTGTAA AGGACCTGCT CTTACATTTA AAGAAACTTT TTCGCGAGGG ACGGTTCAAC
     GTCAAACATT TCCTGGACGA GAATGTAAAT TTCTTTGAAA AAGCGCTCCC TGCCAAGTTG

E  S  K  Y  G  P  P  C  P  P  C  P  A  P  E  F  L  G  G  P
421  GAGTCCAAAT ATGGTCCCCC ATGCCCACCA TGCCCAGCAC CTGAGTTCCT GGGGGGACCA
     CTCAGGTTTA TACCAGGGGG TACGGGTGGT ACGGGTCGTG GACTCAAGGA CCCCCCTGGT

S  V  F  L  F  P  P  K  P  K  D  T  L  M  I  S  R  T  P  E
481  TCAGTCTTCC TGTTCCCCCC AAAACCCAAG GACACTCTCA TGATCTCCCG GACCCCTGAG
     AGTCAGAAGG ACAAGGGGGG TTTTGGGTTC CTGTGAGAGT ACTAGAGGGC CTGGGGACTC

V  T  C  V  V  V  D  V  S  Q  E  D  P  E  V  Q  F  N  W  Y
541  GTCACGTGCG TGGTGGTGGA CGTGAGCCAG GAAGACCCCG AGGTCCAGTT CAACTGGTAC
     CAGTGCACGC ACCACCACCT GCACTCGGTC CTTCTGGGGC TCCAGGTCAA GTTGACCATG

V  D  G  V  E  V  H  N  A  K  T  K  P  R  E  E  Q  F  N  S
601  GTGGATGGCG TGGAGGTGCA TAATGCCAAG ACAAAGCCGC GGGAGGAGCA GTTCAACAGC
     CACCTACCGC ACCTCCACGT ATTACGGTTC TGTTTCGGCG CCCTCCTCGT CAAGTTGTCG
```

FIG. 3B

```
          T  Y  R     V  V  S  V     L  T  V     L  H  Q     D  W  L  N     G  K  E
    661   ACGTACCGTG  TGGTCAGCGT  CCTCACCGTC  CTGCACCAAG  ACTGGCTGAA  CGGCAAGGAG
          TGCATGGCAC  ACCAGTCGCA  GGAGTGGCAG  GACGTGGTTG  TGACCGACTT  GCCGTTCCTC

Y  K  C     K  V  S  N     K  G  L     P  S  S     I  E  K  T     I  S  K
    721   TACAAGTGCA  AGGTCTCCAA  CAAAGGCCTC  CCGTCCTCCA  TCGAGAAAAC  CATCTCCAAA
          ATGTTCACGT  TCCAGAGGTT  GTTTCCGGAG  GGCAGGAGGT  AGCTCTTTTG  GTAGAGGTTT

A  K  G     Q  P  R  E     P  Q  V     Y  T  L     P  P  S  Q     E  E  M
    781   GCCAAAGGGC  AGCCCCGAGA  GCCACAGGTG  TACACCCTGC  CCCCATCCCA  GGAGGAGATG
          CGGTTTCCCG  TCGGGGCTCT  CGGTGTCCAC  ATGTGGGACG  GGGGTAGGGT  CCTCCTCTAC

T  K  N     Q  V  S  L     T  C  L     V  K  G     F  Y  P  S     D  I  A
    841   ACCAAGAACC  AGGTCAGCCT  GACCTGCCTG  GTCAAAGGCT  TCTACCCCAG  CGACATCGCC
          TGGTTCTTGG  TCCAGTCGGA  CTGGACGGAC  CAGTTTCCGA  AGATGGGGTC  GCTGTAGCGG

V  E  W     E  S  N  G     Q  P  E     N  N  Y     K  T  T  P     P  V  L
    901   GTGGAGTGGG  AGAGCAATGG  GCAGCCGGAG  AACAACTACA  AGACCACGCC  TCCCGTGCTG
          CACCTCACCC  TCTCGTTACC  CGTCGGCCTC  TTGTTGATGT  TCTGGTGCGG  AGGGCACGAC

D  S  D     G  S  F  F     L  Y  S     R  L  T     V  D  K  S     R  W  Q
    961   GACTCCGACG  GCTCCTTCTT  CCTCTACAGC  AGGCTAACCG  TGGACAAGAG  CAGGTGGCAG
          CTGAGGCTGC  CGAGGAAGAA  GGAGATGTCG  TCCGATTGGC  ACCTGTTCTC  GTCCACCGTC

E  G  N     V  F  S  C     S  V  M     H  E  A     L  H  N  H     Y  T  Q
   1021   GAGGGGAATG  TCTTCTCATG  CTCCGTGATG  CATGAGGCTC  TGCACAACCA  CTACACACAG
          CTCCCCTTAC  AGAAGAGTAC  GAGGCACTAC  GTACTCCGAG  ACGTGTTGGT  GATGTGTGTC

K  S  L     S  L  S  L     G  K  M     A  L  I     V  L  G  G     V  A  G
   1081   AAGAGCCTCT  CCCTGTCTCT  GGGTAAAATG  GCCCTGATTG  TGCTGGGGGG  CGTCGCCGGC
          TTCTCGGAGA  GGGACAGAGA  CCCATTTTAC  CGGGACTAAC  ACGACCCCCC  GCAGCGGCCG

L  L  L     P  I  G  L     G  I  F     F  R  V     K  F  S  R     S  A  D
   1141   CTCCTGCTTT  TCATTGGGCT  AGGCATCTTC  TTCAGAGTGA  AGTTCAGCAG  GAGCGCAGAC
          GAGGACGAAA  AGTAACCCGA  TCCGTAGAAG  AAGTCTCACT  TCAAGTCGTC  CTCGCGTCTG

A  P  A     Y  Q  Q  G     Q  N  Q     L  Y  N     E  L  N  L     G  R  R
   1201   GCCCCCGCGT  ACCAGCAGGG  CCAGAACCAG  CTCTATAACG  AGCTCAATCT  AGGACGAAGA
          CGGGGGCGCA  TGGTCGTCCC  GGTCTTGGTC  GAGATATTGC  TCGAGTTAGA  TCCTGCTTCT

E  E  Y     D  V  L  D     K  R  R     G  R  D     P  E  M  G     G  K  P
   1261   GAGGAGTACG  ATGTTTTGGA  CAAGAGACGT  GGCCGGGACC  CTGAGATGGG  GGGAAAGCCG
          CTCCTCATGC  TACAAAACCT  GTTCTCTGCA  CCGGCCCTGG  GACTCTACCC  CCCTTTCGGC
```

FIG. 3C

```
        R   R   K     N   P   Q   E     G   L   Y     N   E   L     Q   K   D   K     M   A   E
1321  AGAAGGAAGA  ACCCTCAGGA  AGGCCTGTAC  AATGAACTGC  AGAAAGATAA  GATGGCGGAG
      TCTTCCTTCT  TGGGAGTCCT  TCCGGACATG  TTACTTGACG  TCTTTCTATT  CTACCGCCTC

A   Y   S     E   I   G   M     K   G   E     R   R   R     G   K   G     H   D   G   L
1381  GCCTACAGTG  AGATTGGGAT  GAAAGGCGAG  CGCCGGAGGG  GCAAGGGGCA  CGATGGCCTT
      CGGATGTCAC  TCTAACCCTA  CTTTCCGCTC  GCGGCCTCCC  CGTTCCCCGT  GCTACCGGAA

Y   Q   G     L   S   T   A     T   K   D     T   Y   D     A   L   H   M     Q   A   L
1441  TACCAGGGTC  TCAGTACAGC  CACCAAGGAC  ACCTACGACG  CCCTTCACAT  GCAGGCCCTG
      ATGGTCCCAG  AGTCATGTCG  GTGGTTCCTG  TGGATGCTGC  GGGAAGTGTA  CGTCCGGGAC

P   P   R     *   (SEQ ID NO:4)
1501  CCCCCTCGCT  AAGCGGCCGC  AT   (SEQ ID NO:5)
      GGGGGAGCGA  TTCGCCGGCG  TA   (SEQ ID NO:6)
```

GM-CSFR alpha signal peptide (nucleotides 18-84; SEQ ID NO:7)
IL13 (EmY) (nucleotides 85-420; SEQ ID NO:8)
IgG4 (SmP) (nucleotides 421-1107; SEQ ID NO:9)
CD4tm (nucleotides 1108-1173; SEQ ID NO:10)
CD3 zeta (nucleotides 1174-1512; SEQ ID NO:11)

FIG. 5A

```
        (hEF1p-)
  1   TCGAAGGATC TGCGATCGCT CCGGTGCCCG TCAGTGGGCA GAGCGCACAT CGCCCACAGT
        AGCTTCCTAG ACGCTAGCGA GGCCACGGGC AGTCACCCGT CTCGCGTGTA GCGGGTGTCA

61   CCCCGAGAAG TTGGGGGGAG GGGTCGGCAA TTGAACCGGT GCCTAGAGAA GGTGGCGCGG
        GGGGCTCTTC AACCCCCCTC CCCAGCCGTT AACTTGGCCA CGGATCTCTT CCACCGCGCC

121   GGTAAACTGG GAAAGTGATG TCGTGTACTG GCTCCGCCTT TTTCCCGAGG GTGGGGGAGA
        CCATTTGACC CTTTCACTAC AGCACATGAC CGAGGCGGAA AAAGGGCTCC CACCCCCTCT

181   ACCGTATATA AGTGCAGTAG TCGCCGTGAA CGTTCTTTTT CGCAACGGGT TTGCCGCCAG
        TGGCATATAT TCACGTCATC AGCGGCACTT GCAAGAAAAA GCGTTGCCCA AACGGCGGTC

241   AACACAGCTG AAGCTTCGAG GGGCTCGCAT CTCTCCTTCA CGCGCCCGCC GCCCTACCTG
        TTGTGTCGAC TTCGAAGCTC CCCGAGCGTA GAGAGGAAGT GCGCGGGCGG CGGGATGGAC

301   AGGCTGCCAT CCACGCCGGT TGAGTCGCGT TCTGCCGCCT CCCGCCTGTG TGCCTCCTG
        TCCGACGGTA GGTGCGGCCA ACTCAGCGCA AGACGGCGGA GGGCGGACAC ACGGAGGAC

361   AACTGCGTCC GCCGTCTAGG TAAGTTTAAA GCTCAGGTCG AGACCGGGCC TTTGTCCGGC
        TTGACGCAGG CGGCAGATCC ATTCAAATTT CGAGTCCAGC TCTGGCCCGG AAACAGGCCG

421   GCTCCCTTGG AGCCTACCTA GACTCAGCCG GCTCTCCACG CTTTGCCTGA CCCTGCTTGC
        CGAGGGAACC TCGGATGGAT CTGAGTCGGC CGAGAGGTGC GAAACGGACT GGGACGAACG

481   TCAACTCTAC GTCTTTGTTT CGTTTTCTGT TCTGCGCCGT TACAGATCCA AGCTGTGACC
        AGTTGAGATG CAGAAACAAA GCAAAAGACA AGACGCGGCA ATGTCTAGGT TCGACACTGG

541   GGCGCCTACG TAAGTGATAT CTACTAGATT TATCAAAAAG AGTGTTGACT TGTGAGCGCT
        CCGCGGATGC ATTCACTATA GATGATCTAA ATAGTTTTTC TCACAACTGA ACACTCGCGA

601   CACAATTGAT ACGGATTCAT CGAGAGGGAC ACGTCGACTA CTAACTTCT TCTCTTTCCT
        GTGTTAACTA TGCCTAAGTA GCTCTCCCTG TGCAGCTGAT GATTGAAGA AGAGAAAGGA
```

FIG. 5B (IL13zetakine-)
```
                                    M  L  L     V  T  S     L  L  L
 661  ACAGCTGAGA TCACCCTAGA GCCGCCACCA TGCTTCTCCT GGTGACAAGC CTTCTGCTCT
      TGTCGACTCT AGTGGGATCT CGGCGGTGGT ACGAAGAGGA CCACTGTTCG GAAGACGAGA C  E  L  P  H  P  A  F  L  L  I  P  G  P  V  P  P  S  T  A
 721  GTGAGTTACC ACACCCAGCA TTCCTCCTGA TCCCAGGCCC TGTGCCTCCC TCTACAGCCC
      CACTCAATGG TGTGGGTCGT AAGGAGGACT AGGGTCCGGG ACACGGAGGG AGATGTCGGG L  R  Y  L  I  E  E  L  V  N  I  T  Q  N  Q  K  A  P  L  C
 781  TCAGGTACCT CATTGAGGAG CTGGTCAACA TCACCCAGAA CCAGAAGGCT CCGCTCTGCA
      AGTCCATGGA GTAACTCCTC GACCAGTTGT AGTGGGTCTT GGTCTTCCGA GGCGAGACGT N  G  S  M  V  W  S  I  N  L  T  A  G  M  Y  C  A  A  L  E
 841  ATGGCAGCAT GGTATGGAGC ATCAACCTGA CAGCTGGCAT GTACTGTGCA GCCCTGGAAT
      TACCGTCGTA CCATACCTCG TAGTTGGACT GTCGACCGTA CATGACACGT CGGGACCTTA S  L  I  N  V  S  G  C  S  A  I  E  K  T  Q  R  M  L  S  G
 901  CCCTGATCAA CGTGTCAGGC TGCAGTGCCA TCGAGAAGAC CCAGAGGATG CTGAGCGGAT
      GGGACTAGTT GCACAGTCCG ACGTCACGGT AGCTCTTCTG GGTCTCCTAC GACTCGCCTA F  C  P  H  K  V  S  A  G  Q  F  S  S  L  H  V  R  D  T  K
 961  TCTGCCCCCA CAAGGTCTCA GCTGGCCAGT TTTCCAGCTT GCATGTCCGA GACACCAAAA
      AGACGGGGGT GTTCCAGAGT CGACCGGTCA AAAGGTCGAA CGTACAGGCT CTGTGGTTTT I  E  V  A  Q  F  V  K  D  L  L  L  H  L  K  K  L  F  R  E
1021  TCGAGGTGGC CCAGTTTGTA AAGGACCTGC TCTTACATTT AAAGAAACTT TTTCGCGAGG
      AGCTCCACCG GGTCAAACAT TTCCTGGACG AGAATGTAAA TTTCTTTGAA AAAGCGCTCC G  R  F  N     E  S  K     Y  G  P  F  C  P  P  C  P  A  P  E  F
1061  GACGGTTCAA CGAGTCCAAA TATGGTCCCC CATGCCCACC ATGCCCAGCA CCTGAGTTCC
      CTGCCAAGTT GCTCAGGTTT ATACCAGGGG GTACGGGTGG TACGGGTCGT GGACTCAAGG L  G  G  P  S  V  F  L  F  P  P  K  P  K  D  T  L  M  I  S
1141  TGGGGGGACC ATCAGTCTTC CTGTTCCCCC CAAAACCCAA GGACACTCTC ATGATCTCCC
      ACCCCCCTGG TAGTCAGAAG GACAAGGGGG GTTTTGGGTT CCTGTGAGAG TACTAGAGGG
```

FIG. 5C

```
        R  T  P  E     V  T  C     V  V  V  D     V  S  Q     E  D  P     E  V  Q
1201 GGACCCCTGA GGTCACGTGC GTGGTGGTGG ACGTGAGCCA GGAAGACCCC GAGGTCCAGT
     CCTGGGGACT CCAGTGCACG CACCACCACC TGCACTCGGT CCTTCTGGGG CTCCAGGTCA

F  N  W  Y     V  D  G     V  E  V  H     N  A  K     T  K  P     R  E  E
1261 TCAACTGGTA CGTGGATGGC GTGGAGGTGC ATAATGCCAA GACAAAGCCG CGGGAGGAGC
     AGTTGACCAT GCACCTACCG CACCTCCACG TATTACGGTT CTGTTTCGGC GCCCTCCTCG

Q  F  N  S     T  Y  R     V  V  S  V     L  T  V     L  H  Q     D  W  L
1321 AGTTCAACAG CACGTACCGT GTGGTCAGCG TCCTCACCGT CCTGCACCAG GACTGGCTGA
     TCAAGTTGTC GTGCATGGCA CACCAGTCGC AGGAGTGGCA GGACGTGGTC CTGACCGACT

N  G  K  E     Y  K  C     K  V  S  N     K  G  L     P  S  S     I  E  K
1381 ACGGCAAGGA GTACAAGTGC AAGGTCTCCA ACAAAGGCCT CCCGTCCTCC ATCGAGAAAA
     TGCCGTTCCT CATGTTCACG TTCCAGAGGT TGTTTCCGGA GGGCAGGAGG TAGCTCTTTT

T  I  S  K     A  K  G     Q  P  R  E     P  Q  V     Y  T  L     P  P  S
1441 CCATCTCCAA AGCCAAAGGG CAGCCCCGAG AGCCACAGGT GTACACCCTG CCCCCATCCC
     GGTAGAGGTT TCGGTTTCCC GTCGGGGCTC TCGGTGTCCA CATGTGGGAC GGGGGTAGGG

Q  E  E  M     T  K  N     Q  V  S  L     T  C  L     V  K  G     F  Y  P
1501 AGGAGGAGAT GACCAAGAAC CAGGTCAGCC TGACCTGCCT GGTCAAAGGC TTCTACCCCA
     TCCTCCTCTA CTGGTTCTTG GTCCAGTCGG ACTGGACGGA CCAGTTTCCG AAGATGGGGT

S  D  I  A     V  E  W     E  S  N  G     Q  P  E     N  N  Y     K  T  T
1561 GCGACATCGC CGTGGAGTGG GAGAGCAATG GCCAGCCGGA GAACAACTAC AAGACCACGC
     CGCTGTAGCG GCACCTCACC CTCTCGTTAC CGGTCGGCCT CTTGTTGATG TTCTGGTGCG

P  P  V  L     D  S  D     G  S  F  F     L  Y  S     R  L  T     V  D  K
1621 CTCCCGTGCT GGACTCCGAC GGCTCCTTCT TCCTCTACAG CAGGCTAACC GTGGACAAGA
     GAGGGCACGA CCTGAGGCTG CCGAGGAAGA AGGAGATGTC GTCCGATTGG CACCTGTTCT

S  R  W  Q     E  G  N     V  F  S  C     S  V  M     H  E  A     L  H  N
1681 GCAGGTGGCA GGAGGGGAAT GTCTTCTCAT GCTCCGTGAT GCATGAGGCT CTGCACAACC
     CGTCCACCGT CCTCCCCTTA CAGAAGAGTA CGAGGCACTA CGTACTCCGA GACGTGTTGG
```

FIG. 5D

```
           H  Y  T  Q     K  S  L     S  L  S  L     G  K  M     A  L  I     V  L  G
1741  ACTACACACA  GAAGAGCCTC  TCCCTGTCCC  TAGGTAAAAT  GGCCCTGATT  GTGCTGGGGG
      TGATGTGTGT  CTTCTCGGAG  AGGGACAGGG  ATCCATTTTA  CCGGGACTAA  CACGACCCCC

G  V  A  G     L  L  L     F  I  G  L     G  I  P     F  R  V     K  F  S
1801  GGGTCGCCGG  CCTCCTGCTT  TTCATTGGGC  TAGGCATCTT  CTTCAGAGTG  AAGTTCAGCA
      CCCAGCGGCC  GGAGGACGAA  AAGTAACCCG  ATCCGTAGAA  GAAGTCTCAC  TTCAAGTCGT

R  S  A  D     A  P  A     Y  Q  Q  G     Q  N  Q     L  Y  N     E  L  N
1861  GGAGCGCAGA  CGCCCCTGCG  TACCAGCAGG  GCCAGAACCA  GCTCTATAAC  GAGCTCAATC
      CCTCGCGTCT  GCGGGGACGC  ATGGTCGTCC  CGGTCTTGGT  CGAGATATTG  CTCGAGTTAG

L  G  R  R     E  E  Y     D  V  L  D     K  R  R     G  R  D     P  E  M
1921  TAGGACGAAG  AGAGGAGTAC  GATGTTTTGG  ACAAGAGACG  TGGCCGGGAC  CCTGAGATGG
      ATCCTGCTTC  TCTCCTCATG  CTACAAAACC  TGTTCTCTGC  ACCGGCCCTG  GGACTCTACC

G  G  K  P     R  R  K     N  P  Q  E     G  L  Y     N  E  L     Q  K  D
1981  GGGGAAAGCC  GAGAAGGAAG  AACCCTCAGG  AAGGCCTGTA  CAATGAACTG  CAGAAAGATA
      CCCCTTTCGG  CTCTTCCTTC  TTGGGAGTCC  TTCCGGACAT  GTTACTTGAC  GTCTTTCTAT

K  M  A  E     A  Y  S     E  I  G  M     K  G  E     R  R  R     G  K  G
2041  AGATGGCGGA  GGCCTACAGT  GAGATTGGGA  TGAAAGGCGA  GCGCCGGAGG  GGCAAGGGGC
      TCTACCGCCT  CCGGATGTCA  CTCTAACCCT  ACTTTCCGCT  CGCGGCCTCC  CCGTTCCCCG

H  D  G  L     Y  Q  G     L  S  T  A     T  K  D     T  Y  D     A  L  H
2101  ACGATGGCCT  TTACCAGGGT  CTCAGTACAG  CCACCAAGGA  CACCTACGAC  GCCCTTCACA
      TGCTACCGGA  AATGGTCCCA  GAGTCATGTC  GGTGGTTCCT  GTGGATGCTG  CGGGAAGTGT

M  Q  A  L     P  P  R     *
2161  TGCAGGCCCT  GCCCCCTCGC  TGACGGCCGG  CGAAGGAGG  CCTAGATCTA  TCGATTGTAC
      ACGTCCGGGA  CGGGGGAGCG  ACTGCCGGCC  GCTTCCTCC  GGATCTAGAT  AGCTAACATG (Late SV40pAn-)
2221  AGCTAGCTCG  ACATGATAAG  ATACATTGAT  GAGTTTGGAC  AAACCACAAC  TAGAATGCAG
      TCGATCGAGC  TGTACTATTC  TATGTAACTA  CTCAAACCTG  TTTGGTGTTG  ATCTTACGTC
```

FIG. 5E

```
2281 TGAAAAAAAT GCTTTATTTG TGAAATTTGT GATGCTATTG CTTTATTGT GAAATTTGTG
     ACTTTTTTA  CGAAATAAAC ACTTTAAACA CTACGATAAC GAAATAAACA CTTTAAACAC

2341 ATGCTATTGC TTTATTTGTA ACCATTATAA GCTGCAATAA ACAAGTTAAC AACAACAATT
     TACGATAACG AAATAAACAT TGGTAATATT CGACGTTATT TGTTCAATTG TTGTTGTTAA

2401 GCATTCATTT TATGTTCAG GTTCAGGGG AGGTGTGGGA GGTTTTTAA AGCAAGTAAA
     CGTAAGTAAA ATACAAGTC CAAGTCCCCC TCCACACCCT CCAAAAATT TCGTTCATTT (Ori ColE1~)
2461 ACCTCTACAA ATGTGGTAGA TCCATTTAAA TGTTAGCGAA GAACATGTGA GCAAAAGGCC
     TGGAGATGTT TACACCATCT AGGTAAATTT ACAATCGCTT CTTGTACACT CGTTTTCCGG

2521 AGCAAAAGGC CAGGAACCGT AAAAAGGCCG CGTTGCTGGC GTTTTTCCAT AGGCTCCGCC
     TCGTTTTCCG GTCCTTGGCA TTTTTCCGGC GCAACGACCG CAAAAAGGTA TCCGAGGCGG

2581 CCCCTGACGA GCATCACAAA AATCGACGCT CAAGTCAGAG GTGGCGAAAC CCGACAGGAC
     GGGGACTGCT CGTAGTGTTT TTAGCTGCGA GTTCAGTCTC CACCGCTTTG GGCTGTCCTG

2641 TATAAAGATA CCAGGCGTTT CCCCCTGGAA GCTCCCTCGT GCGCTCTCCT GTTCCGACCC
     ATATTTCTAT GGTCCGCAAA GGGGGACCTT CGAGGGAGCA CGCGAGAGGA CAAGGCTGGG

2701 TGCCGCTTAC CGGATACCTG TCCGCCTTTC TCCCTTCGGG AAGCGTGGCG CTTTCTCAAT
     ACGGCGAATG GCCTATGGAC AGGCGGAAAG AGGGAAGCCC TTCGCACCGC GAAAGAGTTA

2761 GCTCACGCTG TAGGTATCTC AGTTCGGTGT AGGTCGTTCG CTCCAAGCTG GGCTGTGTGC
     CGAGTGCGAC ATCCATAGAG TCAAGCCACA TCCAGCAAGC GAGGTTCGAC CCGACACACG

2821 ACGAACCCCC CGTTCAGCCC GACCGCTGCG CCTTATCCGG TAACTATCGT CTTGAGTCCA
     TGCTTGGGGG GCAAGTCGGG CTGGCGACGC GGAATAGGCC ATTGATAGCA GAACTCAGGT

2881 ACCCGGTAAG ACACGACTTA TCGCCACTGG CAGCAGCCAC TGGTAACAGG ATTAGCAGAG
     TGGGCCATTC TGTGCTGAAT AGCGGTGACC GTCGTCGGTG ACCATTGTCC TAATCGTCTC

2941 CGAGGTATGT AGGCGGTGCT ACAGAGTTCT TGAAGTGGTG GCCTAACTAC GGCTACACTA
     GCTCCATACA TCCGCCACGA TGTCTCAAGA ACTTCACCAC CGGATTGATG CCGATGTGAT
```

FIG. 5F

```
3001  GAAGAACAGT ATTTGGTATC TCGCTCTGC TGAAGCCAGT TACCTTCGGA AAAAGAGTTG
      CTTCTTGTCA TAAACCATAG ACGCGAGACG ACTTCGGTCA ATGGAAGCCT TTTTCTCAAC

3061  GTAGCTCTTG ATCCGGCAAA CAAACCACCG CTGGTAGCGG TGGTTTTTTT GTTTGCAAGC
      CATCGAGAAC TAGGCCGTTT GTTTGGTGGC GACCATCGCC ACCAAAAAAA CAAACGTTCG

3121  AGCAGATTAC GCGCAGAAAA AAAGGATCTC AAGAAGATCC TTTGATCTTT TCTACGGGGT
      TCGTCTAATG CGCGTCTTTT TTTCCTAGAG TTCTTCTAGG AAACTAGAAA AGATGCCCCA

PacI
                                                                 --------
3181  CTGACGCTCA GTGGAACGAA AACTCACGTT AAGGGATTTT GGTCATGGCT AGTTAATTAA
      GACTGCGAGT CACCTTGCTT TTGAGTGCAA TTCCCTAAAA CCAGTACCGA TCAATTAATT (SpAn-)
3241  GCTGCAATAA ACAATCATTA TTTTCATTGG ATCTGTGTGT TGGTTTTTTG TGTGGCTTG
      CGACGTTATT TGTTAGTAAT AAAAGTAACC TAGACACACA ACCAAAAAAC ACACCGAAC

3301  GGGGAGGGGG AGGCCAGAAT GACTCCAAGA GCTACAGGAA GGCAGGTCAG AGACCCCACT
      CCCCTCCCCC TCCGGTCTTA CTGAGGTTCT CGATGTCCTT CCGTCCAGTC TCTGGGTGA

3361  GGACAAACAG TGGCTGGACT CTGCACCATA ACACACAATC AACAGGGGAG TGAGCTGGAT
      CCTGTTTGTC ACCGACCTGA GACGTGGTAT TGTGTGTTAG TTGTCCCCTC ACTCGACCTA (hCMV-1Aprom-)
3421  CGAGCTAGAG TCCGTTACAT AACTTACGGT AAATGGCCCG CCTGGCTGAC CGCCCAACGA
      GCTCGATCTC AGGCAATGTA TTGAATGCCA TTTACCGGGC GGACCGACTG GCGGGTTGCT 3481  CCCCCGCCCA TTGACGTCAA TAATGACGTA TGTTCCCATA GTAACGCCAA TAGGGACTTT
      GGGGGCGGGT AACTGCAGTT ATTACTGCAT ACAAGGGTAT CATTGCGGTT ATCCCTGAAA 3541  CCATTGACGT CAATGGGTGG AGTATTTACG GTAAACTGCC CACTTGGCAG TACATCAAGT
      GGTAACTGCA GTTACCCACC TCATAAATGC CATTTGACGG GTGAACCGTC ATGTAGTTCA 3601  GTATCATATG CCAAGTACGC CCCCTATTGA CGTCAATGAC GGTAAATGGC CCGCCTGGCA
      CATAGTATAC GGTTCATGCG GGGGATAACT GCAGTTACTG CCATTTACCG GGCGGACCGT
```

FIG. 5G

```
3661  TTATGCCCAG TACATGACCT TATGGACTT TCCTACTTGG CAGTACATCT ACGTATTAGT
      AATACGGGTC ATGTACTGGA ATACCCTGAA AGGATGAACC GTCATGTAGA TGCATAATCA

3721  CATGGCTATT ACCATGGTGA TGCGGTTTTG GCAGTACATC AATGGGCGTG GATAGCGGTT
      GTACCGATAA TGGTACCACT ACGCCAAAAC CGTCATGTAG TTACCCGCAC CTATCGCCAA

3781  TGACTCACGG GGATTTCCAA GTCTCCACCC CATTGACGTC AATGGGAGTT TGTTTTGGCA
      ACTGAGTGCC CCTAAAGGTT CAGAGGTGGG GTAACTGCAG TTACCCTCAA ACAAAACCGT

3841  CCAAAATCAA CGGGACTTTC CAAAATGTCG TAACAACTCC GCCCCATTGA CGCAAATGGG
      GGTTTTAGTT GCCCTGAAAG GTTTTACAGC ATTGTTGAGG CGGGGTAACT GCGTTTACCC

3901  CGGTAGGCGT GTACGGTGGG AGGTCTATAT AAGCAGAGCT CGTTTAGTGA ACCGTCAGAT
      GCCATCCGCA CATGCCACCC TCCAGATATA TTCGTCTCGA GCAAATCACT TGGCAGTCTA

3961  CGCCTGGAGA CGCCATCCAC GCTGTTTTGA CCTCCATAGA AGACACCGGG ACCGATCCAG
      GCGGACCTCT GCGGTAGGTG CGACAAAACT GGAGGTATCT TCTGTGGCCC TGGCTAGGTC

4021  CCTCCGCGGC CGGGAACGGT GCATTGGAAC GCGGATTCCC CGTGCCAAGA GTGACGTAAG
      GGAGGCGCCG GCCCTTGCCA CGTAACCTTG CGCCTAAGGG GCACGGTTCT CACTGCATTC

4081  TACCGCCTAT AGAGTCTATA GGCCCACCTA GTTGTGACCG GCGCCTAGTG TTGACAATTA
      ATGGCGGATA TCTCAGATAT CCGGGTGGAT CAACACTGGC CGCGGATCAC AACTGTTAAT

4141  ATCATCGGCA TAGTATAATA CGACTCACTA TAGGAGGGCC ACCATGTCGA CTACTAACCT
      TAGTAGCCGT ATCATATTAT GCTGAGTGAT ATCCTCCCGG TGGTACAGCT GATGATTGGA (HyTK-)
                                                        M  K  P  E  L
4201  TCTTCTCTTT CCTACAGCTG AGATCACCGG TAGGAGGGCC ATCATGAAAA AGCCTGAACT
      AGAAGAGAAA GGATGTCGAC TCTAGTGGCC ATCCTCCCGG TAGTACTTTT TCGGACTTGA

T  A  T  S  V  A  K  F  L  T  E  K  F  D  S  V  S  D  L  M
4261  CACCGCGACG TCTGTCGCCA AGTTTCTGAT CGAAAAGTTC GACAGCGTCT CCGACCTGAT
      GTGGCGCTGC AGACAGCGGT TCAAAGACTA GCTTTTCAAG CTGTCGCAGA GGCTGGACTA
```

FIG. 5H

```
            Q   L   S   E   G   E   S   R   A   F   S   F   D   V   G   R   G   Y
4321   GCAGTCTCG GAGGGCGAAG AATCTCGTGC TTTCAGCTTC GATGTAGGAG GGCGTGGATA
       CGTCAGAGC CTCCCGCTTC TTAGAGCACG AAAGTCGAAG CTACATCCTC CCGCACCTAT

V   L   R   V   N   S   C   A   D   G   F   Y   K   D   R   Y   V   R   H
4381   TGTCCTGCGG GTAAATAGCT GCGCCGATGG TTCTACAAA GATCCTTATG TTTATCGGCA
       ACAGGACGCC CATTTATCGA CGCGGCTACC AAAGATGTTT CTAGCAATAC AAATAGCCGT

F   A   S   A   A   L   P   I   P   E   V   L   D   I   G   E   F   S   E   S
4441   CTTTGCATCG GCCGCGCTCC CGATTCCGGA AGTGCTTGAC ATTGGGGAAT TCAGCGAGAG
       GAAACGTAGC CGGCGCGAGG GCTAAGGCCT TCACGAACTG TAACCCCTTA AGTCGCTCTC

L   T   Y   C   I   S   R   R   Q   G   V   T   L   Q   D   L   P   E   T
4501   CCTGACCTAT TGCATCTCCC GCCGTGCACA GGGTGTCACG TTGCAAGACC TGCCTGAAAC
       GGACTGGATA ACGTAGAGGG CGGCACGTGT CCCACAGTGC AACGTTCTGG ACGGACTTTG

E   L   P   A   V   L   Q   P   V   A   E   L   M   D   A   I   A   A   D
4561   CGAACTGCCC GCTGTTCTGC AACCCGTCGC GGAGCTCATG GATGCGATCG CTGCGGCCGA
       GCTTGACGGG CGACAAGACG TTGGGCAGCG CCTCGAGTAC CTACGCTAGC GACGCCGGCT

L   S   Q   T   S   G   F   G   P   F   G   P   Q   G   I   G   Q   Y   T   T
4621   TCTTAGCCAG ACGAGCGGGT TCGGCCCATT CGGACCGCAA GGAATCGGTC AATACACTAC
       AGAATCGGTC TGCTCGCCCA AGCCGGGTAA GCCTGGCGTT CCTTAGCCAG TTATGTGATG

W   R   D   F   I   C   A   I   A   D   F   H   V   Y   H   N   Q   T   V   M
4681   ATGGCGTGAT TTCATATGCG CGATTGCTGA TCCCCATGTG TATCACTTGC AAACTGTGAT
       TACCGCACTA AAGTATACGC GCTAACGACT AGGGGTACAC ATAGTGACCG TTTGACACTA

D   D   T   V   S   A   S   V   A   Q   A   L   D   S   L   M   L   W   A   E
4741   GGACGACACC GTCAGTGCGT CCGTCGCGCA GGCTCTCGAT AGCTGATCC TTTGGCCGA
       CCTGCTGTGG CAGTCACGCA GGCAGCGCGT CCGAGAGCTA CTCGACTACG AAACCCGGCT

D   C   P   E   V   R   H   L   V   H   A   D   F   G   S   N   V   L   T
4801   GGACTGCCCC GAAGTCCGGC ACCTCGTGCA CGCGGATTTC GGCTCCAACA ATGTCCTGAC
       CCTGACGGGG CTTCAGGCCG TGGAGCACGT GCGCCTAAAG CCGAGGTTGT TACAGGACTG
```

FIG. 5I

```
           D  N  G     R  I  P     A  V  I  D     W  S  E     A  M  P     G  D  S  Q
4861  GGACAATGGC CGCATAACAG CGGTCATTGA CTGGAGCGAG GCGATGTTCG GGGATTCCCA
      CCTGTTACCG GCGTATTGTC GCCAGTAACT GACCTCGCTC CGCTACAAGC CCCTAAGGGT

Y  E  V     A  N  I     F  F  W  R     F  W  L     A  C  M     E  Q  Q  T
4921  ATACGAGGTC GCCAACATCT TCTTCTGGAG GCCGTGGTTG GCTTGTATGG AGCAGCAGAC
      TATGCTCCAG CGGTTGTAGA AGAAGACCTC CGGCACCAAC CGAACATACC TCGTCGTCTG

R  Y  F     E  R  R     R  P  E  L     A  G  S     P  R  L     R  A  Y  M
4981  GCGCTACTTC GAGCGGAGGC ATCCGGAGCT TGCAGGATCG CCGCGGCTCC GGGCGTATAT
      CGCGATGAAG CTCGCCTCCG TAGGCCTCGA ACGTCCTAGC GGCGCCGAGG CCCGCATATA

L  R  I     G  L  D     Q  L  Y  Q     S  L  V     D  G  N     F  D  D  A
5041  GCTCCGCATT GGTCTTGACC AACTCTATCA GAGCTTGGTT GACGGCAATT TCGATGATGC
      CGAGGCGTAA CCAGAACTGG TTGAGATAGT CTCGAACCAA CTGCCGTTAA AGCTACTACG

A  W  A     G  R  C     D  A  I  V     R  S  G     A  G     T  V  G  R
5101  AGCTTGGGCG CAGGGTCGAT GCGACGCAAT CGTCCGATCC GGAGCCGGGA CTGTCGGGCG
      TCGAACCCGC GTCCCAGCTA CGCTGCGTTA GCAGGCTAGG CCTCGGCCCT GACAGCCCGC

T  Q  I     A  R  R     S  A  A  V     W  T  D     G  C  V     E  V  A  S
5161  TACACAAATC GCCCGCAGAA GCGCGGCCGT CTGGACCGAT GGCTGTGTAG AAGTCGCGTC
      ATGTGTTTAG CGGGCGTCTT CGCGCCGGCA GACCTGGCTA CCGACACATC TTCAGCGCAG

A  P  D     Q  A  A     R  S  R  G     H  S  N     R  R  T     A  L  R  P
5221  TGCGTTCGAC CAGGCTGCGC GTTCTCGCGG CCATAGCAAC CGACGTACGG CGTTGCGCCC
      ACGCAAGCTG GTCCGACGCG CAAGAGCGCC GGTATCGTTG GCTGCATGCC GCAACGCGGG

R  R  Q     E  A     T  E  V  R     P  E  Q     K  M  P     T  L  L  R
5281  TCGCCGGCAG CAAGAAGCCA CGGAAGTCCG CCCGGAGCAG AAAATGCCCA CGCTACTGCG
      AGCGGCCGTC GTTCTTCGGT GCCTTCAGGC GGGCCTCGTC TTTTACGGGT GCGATGACGC

V  Y  I     D  G  P     H  G  M  G     K  T  T     T  T  Q     L  L  V  A
5341  GGTTTATATA GACGGTCCCC ACGGGATGGG GAAAACCACC ACCACGCAAC TGCTGGTGGC
      CCAAATATAT CTGCCAGGGG TGCCCTACCC CTTTTGGTGG TGGTGCGTTG ACGACCACCG
```

FIG. 5J

```
        L  G  S     R  D  D     I  V  Y  V     P  E  P        M  T  Y     W  R  V  L
5401    CCTGGTTCG   CGGACGATA   TCGTCTACGT   ACCCGAGCCG   ATGACTTACT   GGCGGGTGCT
        GGACCCAAGC   GCCTGCTAT   AGCAGATGCA   TGGGCTCGGC   TACTGAATGA   CCGCCCACGA

G  A  S     E  T  I     A  N  I  Y     T  T  Q     H  R  L     D  Q  G  E
5461    GGGGCTTCC   GAGACAATCG   CGAACATCTA   CACCACACAA   CACCGCCTGG   ACCAGGGTGA
        CCCCGAAGG   CTCTGTTAGC   GCTTGTAGAT   GTGGTGTGTT   GTGGCGGACC   TGGTCCCACT

I  S  A     G  D  A     V  V  M     T  S  A     Q  I  T     M  G  M  P
5521    GATATCGGCC   GGGGACGCGG   CGGTGGTAAT   GACAAGCGCC   CAGATAACAA   TGGGCATGCC
        CTATAGCCGG   CCCCTGCGCC   GCCACCATTA   CTGTTCGCGG   GTCTATTGTT   ACCCGTACGG

Y  A  V     T  D  A     V  L  P     H  I  G     E  A     G  S  S  H
5581    TTATGCCGTG   ACCGACGCCG   TTCTGGCTCC   TCATATCGGG   GGGAGGCTG   GGAGCTCACA
        AATACGGCAC   TGGCTGCGGC   AAGACCGAGG   AGTATAGCCC   CCCCTCCGAC   CCTCGAGTGT

A  P  P     P  A  L     T  L  I  F     D  R  H     P  I  A     A  L  L  C
5641    TGCCCCGCCC   CCGGCCCTCA   CCCTCATCTT   CGACCGCCAT   CCCATCGCCG   CCCTCCTGTG
        ACGGGGCGGG   GGCCGGGAGT   GGGAGTAGAA   GCTGGCGGTA   GGGTAGCGGC   GGGAGGACAC

Y  P  A     A  R  Y     L  G  S     M  T  P     Q  A  V     L  A  F  V
5701    CTACCCCGCC   GCGCGGTACC   TTATGGGCAG   CATGACCCCC   CAGGCCGTGC   TGGCGTTCGT
        GATGGGCCGG   CGCGCCATGG   AATACCCGTC   GTACTGGGGG   GTCCGGCACG   ACCGCAAGCA

A  L  I     P  P  T     L  P  G     T  N  I  V     L  G  A     L  P  E  D
5761    GGCCCTCATC   CCGCCGACCT   TGCCCGGCAC   CAACATCGTG   CTTGGGGCCC   TTCCGGAGGA
        CCGGGAGTAG   GGCGGCTGGA   ACGGGCCGTG   GTTGTAGCAC   GAACCCCGGG   AAGGCCTCCT

R  H  I     D  R  L     A  K  R  Q     R  P  G     E  R  L     D  L  A  M
5821    CAGACACATC   GACCGCCTGG   CCAAACGCCA   GCGCCCCGGC   GAGCGGCTGG   ACCTGGCTAT
        GTCTGTGTAG   CTGGCGGACC   GGTTTGCGGT   CGCGGGGCCG   CTCGCCGACC   TGGACCGATA

L  A  A     I  E  K     V  Y  G  L     A  N     T  V  R     Y  L  Q  C
5881    GCTGGCTGCG   ATTGAGAAG   GTTTACGGCT   ACTTGCCAAT   ACGGTGCGGT   ATCTGCAGTG
        CGACCGACGC   TAACGCTTC   CAAATGCCGA   TGAACGGTTA   TGCCACGCCA   TAGACGTCAC
```

FIG. 5K

```
             G  G  S     W  R     D  W  G  Q     L  S  G     T  A  V     P  P  Q  G
     5941   CGGCGGGTCG  TGGCGGGAGG  ACTGGGCACA  GCTTTCGGGG  ACGGCCGTGC  CGCCCCAGGG
            GCCGCCCAGC  ACCGCCCTCC  TGACCCGTGT  CGAAAGCCCC  TGCCGGCACG  GCGGGGTCCC

A  E  P     Q  S  N     A  G  P  R     P  H  I     G  D  T     L  F  T  L
     6001   TGCCGAGCCC  CAGAGCAACG  CGGGCCCACG  ACCCCATATC  GGGGACACGT  TATTTACCCT
            ACGGCTCGGG  GTCTCGTTGC  GCCCGGGTGC  TGGGGTATAG  CCCCTGTGCA  ATAAATGGGA

F  R  A     P  E  L     L  A  P  N     G  D  L     Y  N  V     F  A  W  A
     6061   GTTTCGGGCC  CCCGAGTTGC  TGGCCCCCAA  CGGCGACCTG  TATAACGTGT  TTGCCTGGGC
            CAAAGCCCGG  GGGCTCAACG  ACCGGGGGTT  GCCGCTGGAC  ATATTGCACA  AACGGACCCG

L  D  V     L  A  K     R  L  S     M  H  V     F  I  L     D  Y  D  Q
     6121   CTTGGACGTC  TTGGCCAAAC  GCCTCCGTTC  CATGCACGTC  TTTATCCTGG  ATTACGACCA
            GAACCTGCAG  AACCGGTTTG  CGGAGGCAAG  GTACGTGCAG  AAATAGGACC  TAATGCTGGT

S  P  A     G  C  R     D  A  L  L     Q  L  T     S  G  M     V  Q  T  H
     6181   ATCGCCCGCC  GGCTGCCGGG  ACGCCCTGCT  GCAACTTACC  TCCGGGATGG  TCCAGACCCA
            TAGCGGGCGG  CCGACGGCCC  TGCGGGACGA  CGTTGAATGG  AGGCCCTACC  AGGTCTGGGT

V  T  T     P  G  S     I  P  T  I     C  D  L     A  R  T     F  A  R  E
     6241   CGTCACCACC  CCCGGCTCCA  TACCGACGAT  ATGCGACCTG  GCGCGCACGT  TTGCCCGGGA
            GCAGTGGTGG  GGGCCGAGGT  ATGGCTGCTA  TACGCTGGAC  CGCGCGTGCA  AACGGGCCCT

M  G  E     A  N  * (BGh pAn-)
     6301   GATGGGGGAG  GCTAACTGAG  TCGAGAATTC  GCTAGAGGGC  CCTATTCTAT  AGTGTCACCT
            CTACCCCCTC  CGATTGACTC  AGCTCTTAAG  CGATCTCCCG  GGATAAGATA  TCACAGTGGA

6361   AAATGCTAGA  GCTCGCTGAT  CAGCCTCGAC  TGTGCCTTCT  AGTTGCCAGC  CATCTGTTGT
            TTTACGATCT  CGAGCGACTA  GTCGGAGCTG  ACACGGAAGA  TCAACGGTCG  GTAGACAACA

6421   TTGCCCCTCC  CCCGTGCCTT  CCTTGACCCT  GGAAGGTGCC  ACTCCCACTG  TCCTTTCCTA
            AACGGGGAGG  GGGCACGGAA  GGAACTGGGA  CCTTCCACGG  TGAGGGTGAC  AGGAAAGGAT

6481   ATAAAATGAG  GAAATTGCAT  CGCATTGTCT  GAGTAGGTGT  CATTCTATTC  TGGGGGGTGG
            TATTTTACTC  CTTTAACGTA  GCGTAACAGA  CTCATCCACA  GTAAGATAAG  ACCCCCCACC
```

FIG. 5L

```
6541  GGTGGGGCAG GACAGCAAGG GGGAGGATTG GGAAGACAAT AGCAGGCATG CGCAGGGCCC
      CCACCCCGTC CTGTCGTTCC CCCTCCTAAC CCTTCTGTTA TCGTCCGTAC GCGTCCCGGG

6601  AATTGCTCGA GCGGCCGCAA TAAAATATCT TTATTTTCAT TACATCTGTG TGTTGGTTTT
      TTAACGAGCT CGCCGGCGTT ATTTTATAGA AATAAAAGTA ATGTAGACAC ACAACCAAAA

6661  TTGTGTGAAT CTAACTAAC ATACGCTCTC CATCAAAACA AAACGAAACA AAACAAACTA
      AACACACTTA GATTGATTG TATGCGAGAG GTAGTTTTGT TTTGCTTTGT TTTGTTTGAT

6721  GCAAAATAGG CTGTCCCCAG TGCAAGTGCA GGTGCCAGAA CATTTCTCTA  (SEQ ID NO:13)
      CGTTTTATCC GACAGGGGTC ACGTTCACGT CCACGGTCTT GTAAAGAGAT  (SEQ ID NO:14)
```

IL13zetakine amino acid sequence (SEQ ID NO:15).
HyTK amino acid sequence (SEQ ID NO:16).

FIG. 14

```
                                        ATGCTGCTGC TGGTGACCAG
CCTGCTGCTG TCGAGCTGC CCCACCCCGC CTTTCTGCTG ATCCCTGGCC CCGTGCCCCC
TAGCACCGCC CTGCGCTACC TGATCGAGGA ACTGGTGAAC ATCACCCAGA ACCAGAAAGC
CCCCCTGTGC AACGGCAGCA TGGTGTGGAG CATCAACCTG ACGGCCGGCA TGTACTGTGC
CGCCCTGGAA AGCCTGATCA ACGTGAGCGG CTGCAGCGCC ATCGAGAAAA CCCAGCGGAT
GCTGTCCGGC TTCTGCCCCC ACAAGGTGTC CGCCGGACAG TTCAGCAGCC TGCACGTGCG
GGACACCAAG ATCGAGGTGG CCCAGTTCGT GAAGGACCTG CTGCTGCACC TGAAGAAGCT
GTTCCGGGAG GGCCGGTTCA ACGAGAGCAA GTACGGCCCT CCCTGCCCCC CTTGCCCTGC
CCCAGAGTTC CTGGGCGGAC CCAGCGTGTT CCTGTTCCCC CCCAAGCCCA AGGACACCCT
GATGATCAGC CGGACCCCTG AGGTGACCTG CGTGGTGGTG GACGTGAGCC AGGAAGATCC
TGAGGTCCAG TTCAATTGGT ACGTGGACGG CGTGGAAGTG CACAACGCCA AGACCAAGCC
CAGAGAGGAA CAGTTCAACA GCACCTACCG GGTGGTGTCT GTGCTGACCG TGCTGCACCA
GGACTGGCTG AACGGCAAAG AATACAAGTG CAAGGTGTCC AACAAGGGCC TGCCCAGCAG
CATCGAAAAG ACCATCAGCA AGGCCAAGGG CCAGCCTCGC GAGCCCCAGG TGTACACCCT
GCCTCCCTCC CAGGAAGAGA TGACCAAGAA CCAGGTGTCC CTGACCTGCC TGGTGAAGGG
CTTCTACCCC AGCGACATCG CCGTGGAGTG GGAGAGCAAC GGCCAGCCTG AGAACAACTA
CAAGACCACC CCTCCCGTGC TGGACAGCGA CGGCAGCTTC TTCCTGTACA GCCGGCTGAC
CGTGGACAAG AGCCGGTGGC AGGAAGGCAA CGTCTTTAGC TGCAGCGTGA TGCACGAGGC
CCTGCACAAC CACTACACCC AGAAGAGCCT GAGCCTGTCC CTGGGCAAGA TGTTCTGGGT
GCTGGTGGTG GTGGGCGGGG TGCTGGCCTG CTACAGCCTG CTGGTGACAG TGGCCTTCAT
CATCTTTTGG GTGCGGAGCA AGCGGAGCAG AGGCGGCCAC AGCGACTACA TGAACATGAC
CCCCAGACGG CCTGGCCCA CCCGGAAGCA CTACCAGCCC TACGCCCCAC CCAGGGACTT
TGCCGCCTAC CGGTCCGGCG GAGGGCGGGT GAAGTTCAGC AGAAGCGCCG ACGCCCCTGC
CTACCAGCAG GGCCAGAATC AGCTGTACAA CGAGCTGAAC CTGGGCAGAA GGGAAGAGTA
CGACGTCCTG GATAAGCGGA GAGGCCGGGA CCCTGAGATG GGCGGCAAGC CTCGGCGGAA
GAACCCCCAG GAAGGCCTGT ATAACGAACT GCAGAAAGAC AAGATGGCCG AGGCCTACAG
CGAGATCGGC ATGAAGGGCG AGCGGAGGCG GGGCAAGGGC CACGACGGCC TGTATCAGGG
CCTGTCCACC GCCACCAAGG ATACCTACGA CGCCCTGCAC ATGCAGGCCC TGCCCCAAG
GTGA  (SEQ ID NO:36)
```

FIG. 15

```
              ATGCT TCTCCTGGTG ACAAGCCTTC TGTCTGTGA GTTACCACAC
CCAGCATTCC TTCTGATCCC AGGCCCTGTG CCTCCTCTA CAGCCCTCAG GGAGCTCATT
GAGGAGCTGG TCAACATCAC CCAGAACCAG AAGGCTCCGC TCTGCAATGG CAGCATGGTA
TGGAGCATCA ACCTGACAGC TGGCATGTAC TGTGCAGCCC TGGAATCCCT GATCAACGTG
TCAGGCTGCA GTGCCATCGA GAAGACCCAG AGGATGCTGA GCGGATTCTG CCCCCACAAG
GTCTCAGCTG GGCAGTTTTC CAGCTTGCAT GTCGAGACA CCAAAATCGA GGTGGCCCAG
TTTGTAAAGG ACCTGCTCTT ACATTTAAAG AAACTTTTTC GCGAGGGACG GTTCAACGAG
TCCAAATATG GTCCCCCATG CCCACCATGC CCAGCACCTG AGTTCCTGGG GGGACCATCA
GTCTTCCTGT TCCCCCCAAA ACCCAAGGAC ACTCTCATGA TCTCCCGGAC CCCTGAGGTC
ACGTGCGTGG TGGTGGACGT GAGCCAGGAA GACCCCGAGG TCCAGTTCAA CTGGTACGTG
GATGGCGTGG AGTGCATAA TGCCAAGACA AAGCCGCGGG AGGAGCAGTT CAACAGCACG
TACCGTGTGG TCAGCGTCCT CACCGTCCTG CACCAGGACT GGCTGAACGG CAAGGAGTAC
AAGTGCAAGG TCTCCAACAA AGGCCTCCCG TCCTCCATCG AGAAAACCAT CTCCAAAGCC
AAAGGGCAGC CCCGAGAGCC ACAGGTGTAC ACCCTGCCCC CATCCCAGGA GGAGATGACC
AAGAACCAGG TCAGCCTGAC CTGCCTGGTC AAAGGCTTCT ACCCCAGCGA CATCGCCGTG
GAGTGGGAGA GCAATGGGCA GCCGGAGAAC AACTACAAGA CCACGCCTCC CGTGCTGGAC
TCCGACGGCT CCTTCTTCCT CTACAGCAGG CTAACCGTGG ACAAGAGCAG GTGGCAGGAG
GGGAATGTCT TCTCATGCTC CGTGATGCAT GAGGCTCTGC ACAACCACTA CACACAGAAG
AGCCTCTCCC TGTCTCTGGG TAAAATGGCC CTGATTGTGC TGGGGGCGT CGCCGGCCTC
CTGCTTTTCA TTGGGCTAGG CATCTTCTTC AGGAGTAAGA GGAGCAGGCT CCTGCACAGT
GACTACATGA ACATGACTCC CCGCCGCCCT GGGCCCACCC GCAAGCATTA CCAGCCCTAT
GCCCCACCAC GGGACTTCGC AGCCTATCGC TCCGAGGTG GCAAACGGGG CAGAAAGAAA
CTCCTGTATA TATTCAAACA ACCATTTATG AGACCAGTAC AAACTACTCA AGAGGAAGAT
GGCTGTAGCT GCCGATTTCC AGAAGAAGAA GAAGGAGGAT GTGAACTGGG AGGTGGCAGA
GTGAAGTTCA GCAGGAGCGC AGACGCCCCC GCGTACCAGC AGGGCCAGAA CCAGCTCTAT
AACGAGCTCA ATCTAGGACG AAGAGAGGAG TACGATGTTT TGGACAAGAG ACGTGGCCGG
GACCCTGAGA TGGGGGGAAA GCCGAGAAGG AAGAACCCTC AGGAAGGCCT GTACAATGAA
CTGCAGAAAG ATAAGATGGC GGAGGCCTAC AGTGAGATTG GGATGAAAGG CGAGCGCCGG
AGGGGCAAGG GGCACGATGG CCTTTACCAG GGTCTCAGTA CAGCCACCAA GGACACCTAC
GACGCCCTTC ACATGCAGGC CCTGCCCCCT CGCTGA   (SEQ ID NO:37)
```

FIG. 16

```
                  AT GCTTCTCCTG GTGACAAGCC TTCTGCTCTG TGAGTTACCA
CACCCAGCAT TCTCCTGAT CCCAGGCCCT GTGCCTCCT CTACAGCCCT CAGGTACCTC
ATTGAGGAGC TGGTCAACAT CACCCAGAAC CAGAAGGCTC CGCTCTGCAA TGGCAGCATG
GTATGGAGCA TCAACCTGAC AGCTGGCATG TACTGTGCAG CCCTGGAATC CCTGATCAAC
GTGTCAGGCT GCAGTGCCAT CGAGAAGACC CAGAGGATGC TGAGCGGATT CTGCCCGCAC
AAGGTCTCAG CTGGCAGTT TTCCAGCTTG CATGTCCGAG ACACCAAAAT CGAGGTGGCC
CAGTTTGTAA AGGACCTGCT CTTACATTTA AAGAAACTTT TTCGCGAGGG ACGGTTCAAC
GAGTCCAAAT ATGGTCCCCC ATGCCCACCA TGCCCAGCAC CTGAGTTCCT GGGGGGACCA
TCAGTCTTCC TGTTCCCCCC AAAACCCAAG GACACTCTCA TGATCTCCCG GACCCCTGAG
GTCACGTGCG TGGTGGTGGA CGTGAGCCAG GAAGACCCCG AGGTCCAGTT CAACTGGTAC
GTGGATGGCG TGGAGGTGCA TAATGCCAAG ACAAAGCCGC GGGAGGAGCA GTTCAACAGC
ACGTACCGTG TGGTCAGCGT CCTCACCGTC CTGCACCAGG ACTGGCTGAA CGGCAAGGAG
TACAAGTGCA AGGTCTCCAA CAAAGGCCTC CCGTCCTCCA TCGAGAAAAC CATCTCCAAA
GCCAAAGGGC AGCCCCGAGA GCCACAGGTG TACACCCTGC CCCCATCCCA GGAGGAGATG
ACCAAGAACC AGGTCAGCCT GACCTGCCTG GTCAAAGGCT TCTACCCCAG CGACATCGCC
GTGGAGTGGG AGAGCAATGG GCAGCCGGAG AACAACTACA AGACCACGCC TCCCGTGCTG
GACTCCGACG GCTCCTTCTT CCTCTACAGC AAGCTAACCG TGGACAAGAG CAGGTGGCAG
GAGGGGAATG TCTTCTCATG CTCCGTGATG CATGAGGCTC TGCACAACCA CTACACACAG
AAGAGCCTCT CCCTGTCCCT AGGTAAATTT TGGTGCTGG TGTGGTTGG TGAGTCCTG
GCTTCCTATA GCTTGTAGT AACAGTGGCC TTTATTATTT TCTGGGTGAG GAGTAAGAGG
AGCAGGCTCC TGCACAGTGA CTACATGAAC ATGACTCCCC GCCGCCCGG GCCCACCCGC
AAGCATTACC AGCCCTATGC CCACCACGC GACTTCCCAG CCTATCGCTC AGGGACCAG
AGGCTGCCCC CCGATGCCCA CAAGCCCCCT GGGGGAGGCA GTTTCCGGAC CCCCATCCAA
GAGGAGCAGG CCGACGCCCA CTCCACCCTG GCCAAGATCA GAGTGAAGTT CAGCAGGAGC
GCAGACGCCC CGGCGTACCA GCAGGGCCAG AACCAGCTCT ATAACGAGCT CAATCTAGGA
CGAAGAGAGG AGTACGATGT TTTGGACAAG AGACGTGGCC GGGACCCTGA GATGGGGGGA
AAGCCGAGAA GGAAGAACCC TCAGGAAGGC CTGTACAATG AACTGCAGAA AGATAAGATG
GCGGAGGCCT ACAGTGAGAT TGGGATGAAA GGCGAGCGCC GGAGGGGCAA GGGTCACGAT
GGCCTTTACC AGGGTCTCAG TACAGCCACC AAGGACACCT ACGACGCCCT TCACATGCAG
GCCCTGCCCC CTCGCTGA    (SEQ ID NO:38)
```

FIG. 17

```
ATGCTTCTCC TGGTGACAAG CCTCTGCTC TGTGAGTTAC CACACCCAGC ATTCCTCCTG
ATCCCAGGCC CTGTGCCTCC CTCTACAGCC CTCAGGTACC TCATTGAGGA GCTGGTCAAC
ATCACCCAGA ACCAGAAGGC TCCGCTCTGC AATGGCAGCA TGGTATGGAG CATCAACCTG
ACAGCTGGCA TGTACTGTGC AGCCCTGGAA TCCCTGATCA ACGTGTCAGG CTGCAGTGCC
ATCGAGAAGA CCCAGAGGAT GCTGAGCGGA TTCTGCCCGC ACAAGGTCTC AGCTGGGCAG
TTTTCCAGCT TGCATGTCCG AGACACCAAA ATCGAGGTGG CCCAGTTTGT AAAGGACCTG
CTCTTACATT TAAAGAAACT TTTTCGCGAG GGACGGTTCA ACGAGTCCAA ATATGGTCCC
CCATGCCCAC CATGCCCAGC ACCTGAGTTC CTGGGGGGAC CATCAGTCTT CCTGTTCCCC
CCAAAACCCA AGGACACTCT CATGATCTCC CGGACCCCTG AGGTCACGTG CGTGGTGGTG
GACGTGAGCC AGGAAGACCC CGAGGTCCAG TTCAACTGGT ACGTGGATGG CGTGGAGGTG
CATAATGCCA AGACAAAGCC GCGGGAGGAG CAGTTCAACA GCACGTACCG TGTGGTCAGC
GTCCTCACCG TCCTGCACCA GGACTGGCTG AACGGCAAGG AGTACAAGTG CAAGGTCTCC
AACAAAGGCC TCCCGTCCTC CATCGAGAAA ACCATCTCCA AAGCCAAAGG GCAGCCCCGA
GAGCCACAGG TGTACACCCT GCCCCCATCC CAGGAGGAGA TGACCAAGAA CCAGGTCAGC
CTGACCTGCC TGGTCAAAGG CTTCTACCCC AGCGACATCG CCGTGGAGTG GGAGAGCAAT
GGGCAGCCGG AGAACAACTA CAAGACCACG CCTCCCGTGC TGGACTCCGA CGGCTCCTTC
TTCCTCTACA GCAGGCTAAC CGTGGACAAG AGCAGGTGGC AGGAGGGGAA TGTCTTCTCA
TGCTCCGTGA TGCATGAGGC TCTGCACAAC CACTACACAC AGAAGAGCCT CTCCCTGTCC
CTAGGTAAAA TGTTTTGGGT GCTGGTGGTG GTTGGTGGAG TCCTGGCTTG CTATAGCTTG
CTAGTAACAG TGGCCTTTAT TATTTTCTGG GTGAGGAGTA AGAGGAGCAG GGGCGGACAC
AGTGACTACA TGAACATGAC TCCCCGCCGC CCTGGGCCCA CCCGCAAGCA TTACCAGCCC
TATGCCCCAC CACGCGACTT CGCAGCCTAT CGCTCCGGAG GTGGCAAACG GGCAGAAAG
AAACTCCTGT ATATATTCAA ACAACCATTT ATGAGACCAG TACAAACTAC TCAAGAGGAA
GATGGCTGTA GCTGCCGATT TCCAGAAGAA GAAGAAGGAG GATGTGAACT GGGAGGTGGC
AGAGTGAAGT TCAGCAGGAG CGCAGACGCC CCCGCGTACC AGCAGGGCCA GAACCAGCTC
TATAACGAGC TCAATCTAGG ACGAAGAGAG GAGTACGATG TTTTGGACAA GAGACGTGGC
CGGGACCCTG AGATGGGGGG AAAGCCGAGA AGGAAGAACC CTCAGGAAGG CCTGTACAAT
GAACTGCAGA AAGATAAGAT GGCGGAGGCC TACAGTGAGA TTGGGATGAA AGGCGAGCGC
CGGAGGGGCA AGGGGCACGA TGGCCTTTAC CAGGGTCTCA GTACAGCCAC CAAGGACACC
TACGACGCCC TTCACATGCA GGCCCTGCCC CCTCGCTGA    (SEQ ID NO:39)
```

FIG. 18

```
                                        ATGCTTCTCC TGGTGACAAG CCTTCTGCTC
TGTGAGTTAC CACACCCAGC ATTCCTCCTG ATCCAGGCC CTGTGCCTCC CTCTACAGCC
CTCAGGTACC TCATTGAGGA GCTGGTCAAC ATCACCCAGA ACCAGAAGGC TCCGCTCTGC
AATGGCAGCA TGGTATGGAG CATCAACCTG ACAGCTGGCA TGTACTGTGC AGCCCTGGAA
TCCCTGATCA ACGTGTCAGG CTGCAGTGCC ATCGAGAAGA CCCAGAGGAT GCTGAGCGGA
TTCTGCCCGC ACAAGGTCTC AGCTGGGCAG TTTCCAGCT TGCATGTCCG AGACACCAAA
ATCGAGGTGG CCCAGTTTGT AAAGGACCTG CTCTTACATT TAAAGAAACT TTTTCGCGAG
GGACGGTTCA ACGAGTCCAA ATATGGTCCC CCATGCCCAC CATGCCCAGC ACCTGAGTTC
CTGGGGGGAC CATCAGTCTT CCTGTTCCCC CCAAAACCCA AGGACACTCT CATGATCTCC
CGGACCCCTG AGGTCACGTG CGTGGTGGTG GACGTGAGCC AGGAAGACCC CGAGGTCCAG
TTCAACTGGT ACGTGGATGG CGTGGAGGTG CATAATGCCA AGACAAAGCC GCGGGAGGAG
CAGTTCAACA GCACGTACCG TGTGGTCAGC GTCCTCACCG TCCTGCACCA GGACTGGCTG
AACGGCAAGG AGTACAAGTG CAAGGTCTCC AACAAAGGCC TCCCGTCCTC CATCGAGAAA
ACCATCTCCA AAGCCAAAGG GCAGCCCCGA GAGCCACAGG TGTACACCCT GCCCCCATCC
CAGGAGGAGA TGACCAAGAA CCAGGTCAGC CTGACCTGCC TGGTCAAAGG CTTCTACCCC
AGCGACATCG CCGTGGAGTG GGAGAGCAAT GGGCAGCCGG AGAACAACTA CAAGACCACG
CCTCCCGTGC TGGACTCCGA CGGCTCCTTC TTCCTCTACA GCAGGCTAAC CGTGGACAAG
AGCAGGTGGC AGGAGGGGAA TGTCTTCTCA TGCTCCGTGA TGCATGAGGC TCTGCACAAC
CACTACACAC AGAAGAGCCT CTCCCTGTCC CTAGGTAAAA TGTTTTGGGT GCTGGTGGTG
GTTGGTGGAG TCCTGGCTTG CTATAGCTTG CTAGTAACAG TGGCCTTTAT TATTTTCTGG
GTGAGGAGTA AGAGGAGCAG GGGCGGACAC AGTGACTACA TGAACATGAC TCCCCGCCGC
CCTGGGCCCA CCCGCAAGCA TTACCAGCCC TATGCCCCAC CACGCGACTT CGCAGCCTGA
GGTGGCGGAG GTGGCAAACG GGGCAGAAAG AAACTCCTGT ATATATTCAA ACAACCATTT
ATGAGACCAG TACAAACTAC TCAAGAGGAA GATGGCTGTA GCTGCCGATT TCCAGAAGAA
GAAGAAGGAG GATGTGAACT GGGAGTGGC AGAGTGAAGT TCAGCAGGAG CGCAGACGCC
CCCGCGTACC AGCAGGGCCA GAACCAGCTC TATAACGAGC TCAATCTAGG ACGAAGAGAG
GAGTACGATG TTTTGGACAA GAGACGTGGC CGGGACCCTG AGATGGGGGG AAAGCCGAGA
AGGAAGAACC CTCAGGAAGG CCTGTACAAT GAACTGCAGA AAGATAAGAT GGCGGAGGCC
TACAGTGAGA TTGGGATGAA AGGCGAGCGC CGGAGGGGCA AGGGGCACGA TGGCCTTTAC
CAGGGTCTCA GTACAGCCAC CAAGGACACC TACGACGCCC TTCACATGCA GGCCCTGCCC
CCTCGCTGA   (SEQ ID NO:40)
```

METHOD AND COMPOSITIONS USING A CHIMERIC ANTIGEN RECEPTOR FOR ENHANCED ANTI-TUMOR EFFECTOR FUNCTIONING OF T CELLS

CROSS REFERENCE TO RELATED APPLICATION(S)

This application is a 35 U.S.C. §371 National Phase Entry Application from PCT/US2009/055029, filed Aug. 26, 2009, and designating the United States and also claims the benefit of U.S. Provisional Application No. 61/091,915, filed Aug. 26, 2008. The disclosures of which are incorporated herein in its entirety by reference.

STATEMENT REGARDING FEDERALLY SPONSORED RESEARCH

This invention was made with government support in the form of Cancer Center Support Grant no. P30-CA33572-21 from the United States Department of Health and Human Services, National Institutes of Health. The United States government has certain rights in the invention.

BACKGROUND OF THE INVENTION

1. Technical Field

The invention relates to the field of biomedicine and specifically methods useful for cancer therapy. In particular, embodiments of the invention relate to methods for specific CTL immunotherapeutic strategies for cancer including the use of genetically-modified T lymphocytes expressing chimeric immunoreceptors in the treatment of human brain tumors and other cancers.

2. Description of the Background Art

Tumor-specific T cell based immunotherapies have been investigated for anti-tumor treatment, however the T cells suffer from the problem of not surviving and remaining active in vivo for a long enough period. Often, adoptively transferred T cells do not have the desired potency and duration of tumor cell killing. Therefore, there is a need in the art for tumor-specific cancer therapies with longer term anti-tumor functioning.

Cancer-directed immunotherapies traditionally focus on eliciting $CD8^+$ CTL responses. However, stimulation of $CD4^+$ T cell (helper) responses also is important to successful immunotherapy against cancer. $CD4^+$ T cells can influence natural tumor-specific CTL responses directly or indirectly, through conditioning of professional antigen presenting cells via CD40-CD40L, and through the production of cytokines such as IL2 and IFN-γ. The cytocidal effector mechanisms used by $CD4^+$ T cells are mediated either through release of cytokines that activate death receptors on the tumor cell surface, or through direct cell contact where Fas/FasL, TNF-related apoptosis-inducing ligand (TRAIL), or granzyme-perforin dependent pathways mediate tumor cell apoptosis. These helper cells can augment the early clonal expansion and generation of primary $CD8^+$ CTL effectors, and also may affect both the generation and the expansion of functional memory $CD8^+$ T cells.

Full activation of natural $CD4^+$ T cells requires both an antigen-specific signal through engagement of the T cell receptor/CD3 complex with appropriate peptide/MHC class II complexes and costimulatory signals. These costimulatory signals usually are delivered by ligands that are selectively expressed on specialized antigen presenting cells. T cell costimulation is thought to help maintain tolerance to normal self-antigens expressed by tissues that do not deliver this secondary signal. Because most tumor cells, similar to normal tissues, do not express MHC class II or costimulatory molecules, it stands to reason that they also do not normally promote $CD4^+$ T cell stimulation directly. This theory is supported by several studies that have demonstrated enhanced T cell mediated anti-tumor immunity by vaccination with tumor cells that were transfected with the costimulatory ligand B7-1.

While altering tumor cell expression of costimulatory molecules is one way to help drive T cell activation, alternative strategies would be very desirable, particularly strategies which involve allowing the T cell to receive and act on costimulatory signals without the need for actual costimulatory ligand(s).

SUMMARY OF THE INVENTION

Accordingly, embodiments of the present invention provide methods and compositions for enhanced anti-tumor effector functioning of $CD4^+$ and $CD8^+$ T cells for cancer immunotherapy; and specifically to chimeric transmembrane immunoreceptors (termed chimeric antigen receptors or "CARs") which comprise an extracellular domain, a transmembrane region and an intracellular signaling domain. The extracellular domain is made up of a soluble receptor ligand (that is specific for a target tumor antigen or other tumor cell-surface molecule) linked to an optional support region capable of tethering the extracellular domain to a cell surface. The intracellular signaling domain contains the signaling domain from the zeta chain of the human CD3 complex (CD3ζ) and one or more costimulatory signaling domains, such as those from CD28, 4-1BB and OX-40. The extracellular domain contains a recognition element that enables the CAR, when expressed on the surface of a T cell, to direct T cell activity to those cells expressing a receptor or ligand for which this recognition element is specific. For example, a CAR which contains an extracellular domain that contains a recognition element specific for a tumor antigen can direct T cell activity to tumor cells that bear this antigen. The intracellular region enables the T cell to receive costimulatory signals. The costimulatory signaling domains preferably are selected from CD28, 4-1BB, OX-40 or any combination of these. Preferred chimeric receptors comprise a human CD4 transmembrane region, a human $IgG_4$ Fc and a receptor or ligand that is tumor-specific, such as an IL13 or IL3 molecule. The IL13 molecule may contain the E13Y mutation.

Embodiments of the invention also provide a method of cancer immunotherapy which comprises administering to a patient in need thereof a receptor such as those described above. Preferred methods targeting IL13Rα2 are useful in treatment of those cancers, including, for example, glioblastoma, breast cancer, head and neck cancer, kidney cancer, ovarian cancer and Kaposi's sarcoma. The methods are useful in treating any accessible tumor that bears an element that specifically binds to the recognition element on the CAR.

Further embodiments of the invention provide a method of enhancing activity of a chimeric antigen receptor (CAR) against a tumor, which comprises adding CD28, and/or 4-1BB OX-40 signaling domains to the receptor.

Particular embodiments encompassed by the invention include a tumor-specific chimeric antigen receptor (CAR) which comprises a specific recognition element, an optional support or linker region, a transmembrane region, the signaling domain for CD3 zeta chain and at least one additional costimulatory signaling receptor. Such CARs may include those with two costimulatory signaling receptors, for example those selected from the group consisting of CD28, 4-1BB and OX-40, for example CD28 and 4-1BB.

The inventive CARs include those wherein the transmembrane region is a human CD4 transmembrane region, a human CD28 transmembrane region, or a human IgG$_4$ Fc region. Specific recognition elements of the CARs can be an IL13 molecule, an IL3 molecule or the extracellular binding domain of a single chain immunoglobulin that recognizes an antigen selected from the group consisting of Her/2Neu, α3 integrin, CD20, CD19 and EGFRVIII and preferably is an IL13 molecule, most preferably an IL13 molecule that contains the E13Y mutation, such as IL13-CD28-41BBζ.

Embodiments of the invention also encompass isolated polynucleic acids that encode any of the CARs discussed herein and isolated T lymphocytes that express any of the CARs discussed herein. In addition, embodiments of the invention include methods of cancer immunotherapy which comprises administering to a patient in need thereof such polynucleic acids or T lymphocytes, including as treatments for any of the following cancers: glioblastoma, medulloblastoma, breast cancer, head and neck cancer, kidney cancer, ovarian cancer, Kaposi's sarcoma, acute myelogenous leukemia, and B-lineage malignancies.

Further embodiments include methods of enhancing activity of a chimeric antigen receptor against a tumor, which comprises adding CD28 and 4-1BB signaling domains to the receptor.

BRIEF DESCRIPTION OF THE DRAWINGS

FIG. 2 shows the locations of exemplary primers for IL13ζ CAR construction on the native IL13 sequence as indicated. The arrows indicate the position of the primers on the IL13 sequence.

FIG. 3 (given as FIGS. 3A-3C) provides an exemplary IL13 zetakine-encoding nucleotide sequence (SEQ ID NO:5, upper strand; SEQ ID NO:6, lower strand). The segments of DNA in the sequence include GM-CSFR alpha signal peptide (SEQ ID NO:7), IL13(E13Y) (SEQ ID NO:8), IgG$_4$(SmP) (SEQ ID NO:9), CD4tm(SEQ ID NO:10) and CD3zeta (SEQ ID NO:11). The complete amino acid sequence is provided as SEQ ID NO:4.

FIG. 5 (given as FIGS. 5A-5L) provides the sequence of an exemplary plasmid DNA vector (SEQ ID NO:13, upper strand; SEQ ID NO:14, lower strand). An IL13zetakine amino acid sequence (SEQ ID NO:15) and an HyTk amino acid sequence (SEQ ID NO:16) also are indicated. The segments of DNA which make up the complete sequence include hEF1p (nucleotides 6-549; SEQ ID NO:41), IL13 zetakine (nucleotides 690-2183; SEQ ID NO:42), late sv40pAn (nucleotides 2230-2498; SEQ ID NO:43), Ori ColE1 (nucleotides 2499-3245; SEQ ID NO:44), SpAn (nucleotides 3246-3432; SEQ ID NO:45), hCMV-1Aprom (nucleotides 3433-4075; SEQ ID NO:46), HyTK (nucleotides 4244-6319; SEQ ID NO:47) and BGh pAna (nucleotides 6320-6618; SEQ ID NO:48).

FIG. 6A shows a IL13ζ construct and FIG. 6B shows a IL13-CD28-41BBζ construct.

FIG. 14 provides the sequence of IL13-IgG$_4$-cd28tm-CD28gg-Zeta (CO) (SEQ ID NO:36).

FIG. 15 provides the sequence of IL13-IgG$_4$-cd4tm-CD28-4-1BB-Zeta, also referred to herein as IL13-CD28-41BBζ used/discussed above with respect to the examples below (SEQ ID NO:37). This sequence was used to genetically alter T cells to express the IL13-CD28-41BBζ CAR as described and used in FIGS. 1, 6, 7, 8, 10, 11, 12 and 13.

FIG. 16 provides the sequence of IL13-IgG$_4$-cd28tm-CD28-Ox40-Zeta (SEQ ID NO:38).

FIG. 17 provides the sequence of IL13-IgG$_4$-cd28tm-CD28gg-4-1BB-Zeta (SEQ ID NO:39).

FIG. 18 provides the sequence of IL13-IgG$_4$-cd28tm-CD28gg^199-4-1BB-Zeta (SEQ ID NO:40).

DETAILED DESCRIPTION OF THE PREFERRED EMBODIMENTS

Figure 1:
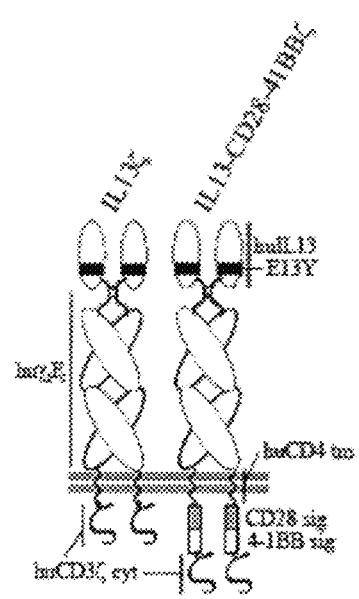
FIG. 1 is a schematic representation of the IL13ζ and IL13-CD28-41BBζ chimeric antigen receptor (CAR) protein molecules.

Adoptive immunotherapy using T lymphocytes that express tumor-specific chimeric antigen receptors (CARs) can be a powerful therapeutic strategy for the treatment of cancer. CARs are made up of an extracellular specific recognition element (such as a receptor that binds a tumor antigen) linked via a transmembrane domain to the CD3ζ cytoplasmic signaling domain. These receptors therefore are able both to bind antigen and to transduce T cell activation, independent of MHC restriction. Thus, CARs are "universal" immunoreceptors which can treat a population of patients with antigen-positive tumors irrespective of their HLA genotype.

According to embodiments of this invention, CARs contain the signaling domain for CD3ζ and the signaling domains of one or more costimulatory receptors that further promote the recycling, survival and/or expansion of adoptively transferred cells expressing the CARs, in addition to specific receptors which allow the cells to engage targets such as tumors. The signaling domains of the costimulatory receptors are the intracellular portions of each receptor protein that generate the activating signal in the cell. Examples are amino acids 180-220 of the native CD28 molecule and amino acids 214-255 of the native 4-1BB molecule. An especially preferred CAR comprises an extracellular recognition element that is specific for a unique cancer cell surface receptor, is stable in vivo and has low immunogenicity. Derivation from a naturally-occurring soluble cell signal molecule helps to achieve these objectives.

The term "CAR" refers to a chimeric antigen receptor which is a recombinant biomolecule that contains an extracellular recognition domain, a transmembrane region, and an intracellular signaling domain. The term "antigen," therefore, is not limited to molecules that bind antibodies, but to any molecule that can bind specifically to any receptor. "Antigen" thus refers to the recognition domain of the CAR. The extracellular recognition domain (also referred to as the extracellular domain or simply by the recognition element which it contains) comprises a recognition element that specifically binds to a molecule present on the cell surface of a target cell. The transmembrane region anchors the CAR in the membrane. The intracellular signaling domain comprises the signaling domain from the zeta chain of the human CD3 complex and optionally comprises one or more co-stimulatory signaling domains.

A CAR that contains the IL13 domain with the E13Y mutation (IL13(E13Y)) and the CD3 zeta chain signalling domain is referred to herein as "IL13ζ" This term includes any chimeric antigen receptor (CAR) that contains an IL13 extracellular recognition domain (a domain that specifically recognizes IL13Rα2 on tumor cells) a transmembrane region, and a CD3 zeta chain intracellular signaling domain. Non-limiting examples of such CARs are provided in Examples 8-12. A CAR that contains IL13(E13Y) and also contains the optional co-stimulatory intracellular domains CD28 and 4-1BB is termed "IL13-CD28-41BBζ" herein.

Persons of skill will recognize that any nucleotide sequence that encodes IL13(E13Y) would also be suitable for this same purpose. The unmutated sequence of the IL13 signaling domain also is suitable. Any IL13 or IL13(E13Y) encoding sequence including variants with 90%, 95%, 98% or 99% homology to the native sequence may be used here. Such sequences which are useful for specifically recognizing an IL13 receptor tumor antigen such as IL13Rα2, therefore include those encoded by the native nucleic acid (see Smernov et al., Gene 155:277-281, 1995, the disclosures of which are hereby incorporated by reference), the same nucleic acid sequence lacking the E13Y mutation, sequences that are 95%, 98% or 99% homologous to these sequences, longer sequences that comprise those sequences but also include additional nucleotides at the 3' or 5' end, for example any number of additional nucleotides or codons, such as 3, 6, 9, 12 or more nucleotides, or up to about 12, 20, 50 or 100 additional nucleotides, and any sequence that encodes the same amino acid sequence as these nucleic acids due to the degeneracy of the genetic code. In particular, sequences that are codon optimized (CO) for expression by the desired host are contemplated as part of the invention.

Soluble recognition elements as used in this invention are derived from de novo synthesized polypeptides, as described for the IL13 (E13Y) coding sequence in Example 1 or from polypeptides of combinatorial libraries such as phage-display libraries or chemically synthesized libraries. Preferred soluble recognition elements are of human origin and are therefore non-immunogenic, but can be tailored in affinity or specificity through mutagenesis. Upon their expression on T cells, soluble recognition elements are able to bind a target element on the target cell (for example a tumor cell, but not to any appreciable extent on non-target cells), in such a way that results in T cell activation. Thus, the soluble recognition elements that are suitable for this invention have certain advantages over antibody fragments or cell adhesion molecules for target specificity in the inventive CARs, since they are more likely to be stable in the extracellular environment, non-antigenic, and more selective, and therefore are preferred. Examples of suitable soluble receptor elements include autocrine and paracrine growth factors, chemokines, cytokines, hormones, and engineered artificial small molecule ligands that exhibit the required specificity. Natural ligand sequences can be engineered to increase their specificity for a particular target cell. Selection of a recognition element for use in a particular CAR is governed by the nature of the target cell, and the qualities discussed above. In one preferred embodiment of the invention, the CAR exploits the tumor-restricted expression of IL13Rα2 by malignant glioma, renal cell carcinoma and other tumors by using as the recognition element a mutant of IL13(E13Y) to direct T cells specifically to IL13Rα2-expressing tumor cells. Analogous recognition elements can be created that are specific to any of a variety of cancer cell types that selectively express receptors antigens or any specific molecule on their cell surfaces, for which selective recognition elements are known or can be engineered.

Examples of suitable support (transmembrane) regions for use with the invention include the constant (Fc) regions of immunoglobins, human CD8a, and artificial linkers that serve to move the targeting moiety away from the cell surface for improved access to and binding on target cells. A preferred support region is the Fc region of an IgG (such as $IgG_4$). Examples of suitable transmembrane domains include the transmembrane domains of the leukocyte CD markers, preferably that of CD4 or CD28. Examples of intracellular receptor signaling domains include the T cell antigen receptor complex, preferably the zeta chain of CD3, however any transmembrane region sufficient to anchor the CAR in the membrane can be used. Persons of skill are aware of numerous transmembrane regions and the structural elements (such as lipophilic amino acid regions) that produce transmembrane domains in numerous membrane proteins and therefore can substitute any convenient sequence. T cell costimulatory signaling receptors suitable for improving the function and activity of CAR-expressing cells include, but are not limited to, CD28 and 4-1BB also known as (CD137), and OX-40.

Signaling via CD28 is required for IL2 production and proliferation, but does not play a primary role in sustaining T cell function and activity. 4-1BB (a tumor necrosis factor-receptor family member expressed following CD28 activation) and OX-40 are involved in driving long-term survival of T cells, and accumulation of T cells. The ligands for these receptors typically are expressed on professional antigen presenting cells such as dendritic cells and activated macrophages, but not on tumor cells. Expressing a CAR that incorporates CD28 and/or 4-1BB signaling domains in $CD4^+$ T cells enhances the activity and anti-tumor potency of those cells compared to those expressing a CAR that contains only the CD3ζ signaling domain. Preferably, the inventive CARs contain both CD28 and 4-1BB signaling domains.

In order for the CAR to target tumor cells, they contain an extracellular binding molecule that binds a tumor surface marker and preferably specifically binds to a unique tumor surface molecule. Some cancers express or overexpress molecules of the immune system. Gliomas, for example, express IL13 receptors, and in particular, high-affinity IL13 receptors. However, unlike the IL13 receptor trimolecular complex used by the immune system, (which consists of the IL13Rα1, the IL4Rβ, and γc), glioma cells overexpress a unique IL13Rα2 chain capable of binding IL13 independently of the requirement for IL4Rβ or γc44. Like its homolog IL4, IL13 has pleotropic immunoregulatory activity outside the CNS. Both IL13 and IL4 stimulate IgE production by B lymphocytes and suppress pro-inflammatory cytokine production by macrophages.

Detailed studies using autoradiography with radiolabeled IL13 have demonstrated abundant IL13 binding on nearly all malignant glioma tissues studied. This binding is highly homogeneous within tumor sections and in single cell analysis. However, molecular probe analysis specific for IL13Rα2 mRNA did not detect expression of the glioma-specific receptor by normal brain elements and autoradiography with radiolabeled IL13 also could not detect specific IL13 binding in the normal CNS. These studies suggest that the shared IL13Rα1/IL41β/γc receptor is not expressed detectably in the normal CNS. Therefore, IL13Rα2 is a very specific cell-surface target for glioma and is a highly suitable target for this invention. Persons of skill are aware of other suitable targets for CARs, which are expressed or overexpressed on the cells to be targeted and preferably are not expressed, or are expressed to a much lesser degree, on other cells. Another example of a tumor-specific target suitable for targeting with CARs of this invention is IL3 receptor (IL3R; e.g., expressed on acute myeloid leukemia (AML) cells.

Binding of IL13-based cytotoxins to the broadly expressed IL13Rα1/IL41β/γc receptor complex, however, has the potential of mediating undesired toxicities to normal tissues outside the CNS, and thus limits the systemic administration of these agents. An amino acid substitution in the IL13 alpha helix A at amino acid 13 of tyrosine for the native glutamic acid selectively reduces the affinity of IL13 to the IL13Rα1/IL41β/γc receptor. Binding of this mutant (termed IL13 (E13Y) to IL13Rα2, however, was increased relative to wild-type IL13 by 50-fold. Thus, this minimally altered IL13 analog simultaneously increases IL13's specificity and affinity for glioma cells. Therefore, a preferred embodiment of the invention employs an IL13 containing a mutation at amino acid 13. IL13 having the natural sequence also may be used with the invention, however, and can be useful, particularly in situations where the modified T cells are to be locally administered, such as by injection directly into a tumor mass.

A preferred type of CAR for specifically targeting tumors that express IL13Rα2 is made up of an extracellular IL13-mutant cytokine in which the IL13 protein contains a substitution of tyrosine for the naturally-occurring glutamic acid at amino acid 13 of the protein (termed IL13(E13Y) here), connected to a human IgG$_4$ hinge-Fc domain support region which is fused to a CD4 transmembrane domain and a cytoplasmic CD3ζ signaling sequence. See FIG. 1, left side. This CAR is referred to herein as an "IL13ζ CAR". When this CAR also contains the CD28 and 4-1BB signaling domains, it is referred to as IL13-CD28-41BBζ. See FIG. 1, right side.

An immunoreceptor according to the present invention can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, PCR, primer-assisted ligation, site-directed mutagenesis, etc.) as is convenient. The resulting coding region is preferably inserted into an expression vector and used to transform a suitable expression host cell line, preferably a T lymphocyte cell line, and most preferably an autologous T lymphocyte cell line.

Briefly, an IL13ζ CAR may be constructed using known methods as follows. The IL13 mutant DNA IL13(E13Y) can be synthesized by PCR with primers based on the known IL13 mRNA sequence. The complete IL13 gene sequence is reported in Smernov et al., "Tandem arrangement of human genes for interleukin-4 and interleukin-13: resemblance in their organization." Gene 155:277-281, 1995, the disclosures of which are hereby incorporated by reference. De novo synthesis of the IL13(E13Y) was performed using forward primer IL13P1 and four reverse primers, IL13P2, IL13P3, IL13P4, and IL13P5, shown in Table I, below, and FIG. 2. This IL13 mutant sequence then can be modified to contain a 5' leader sequence, if desired. A transmembrane anchor such as the human IgG$_4$-CD4 transmembrane (IgG$_4$-CD4tm) and CD3 zetachain (CD3ζ) cytoplasmic sequences also can be added to the 3' end by PCR fusion techniques or any convenient method. The complete IL13ζ sequence is given in FIG. 3 as an example of the invention. The same methods can be used to construct equivalent molecules using different recognition elements. The final construct then can be ligated into any suitable plasmid expression vector. A preferred plasmid expression vector is pMG (available from Invivogen™).

The IL13(E13Y)-containing CAR specifically directs T cells to target IL13 receptor α2 (termed IL13Rα2 here)-expressing glioma cells, renal carcinoma cells and cells of any cancer expressing IL13Rα2 in an MHC-independent manner. Anti-tumor CD4$^+$ T cell effectors were generated to be re-directed to recognize tumor cells using a CAR containing the signaling domains derived from CD3-ζ, CD28 and 4-1BB. Either the IL13ζ or IL13-CD28-41BBζ CAR was transfected into human primary T cells using a non-viral plasmid vector (pEK) and electroporation methods (Nucleofector Technology™ of Amaxa Biosystems™, Gaithersburg, Md.). CD4$^+$ T cells expressing either CAR (IL13ζ or IL13-CD28-41BBζ) were compared for their potential to activate effector-associated signaling pathways, produce cytokines, lyse target cells and control in vivo tumor growth. The results showed that addition of the CD28 and 4-1BB signaling domains to IL13ζ enhances the anti-tumor effector functions of CD4$^+$ T cells expressing the CAR. Effector T cells expressing the IL13-CD28-41BBζ immunoreceptor were able to mediate costimulatory signals through JNK, p38 and AKT kinases in the tumor environment where costimulation would be expected to be limiting. The enforced costimulation in the human primary CD4$^+$ T cells supports the polarization of these cells to a Th$_1$ phenotype in a manner that is associated with sustained anti-tumor efficacy both in vitro and in vivo. Effector signals downstream of the CAR in CD4$^+$ T cells were demonstrated. These effector signals correlated with the observed Th$_1$ bias and the prolonged anti-tumor effector activity of these cells both in vitro and in vivo.

CD3ζ signaling alone drives ERK activation. This correlates well with the finding here that ERK activity is not enhanced in IL13-CD28-41BBζ-expressing cells compared to IL13ζ-expressing controls (both CARs contain the CD3ζ signaling domain). Costimulation of CD3 with CD28 drives activation of JNK and p38; 4-1BB-mediated co-stimulation of CD3 also involves JNK activation. Both JNK and p38 play primary roles in driving Th$_1$-polarized immune responses by CD4$^+$ T cells, including their production of IL2, IFN-γ and TNF-α. The activation of AKT kinase, another downstream signaling component of both CD28 and 4-1BB, also is involved in up-regulation of IL2 and INF-γ, but not Th$_2$ cytokines. The association of a pronounced Th$_1$ phenotype (see examples, below) with enhanced JNK and p38 MAP kinase induction and sustained ATK activation (see examples, below) in IL13-CD28-41BBζ-expressing T cells strongly indicates that the CD28 and 4-1BB signaling moieties work with the CD3ζ signaling domain in this chimeric receptor to retain the capacity to transduce the downstream signaling pathways normally associated with these costimulatory receptors. Regardless of how strong the activated Th$_1$ phenotype driven by costimulatory domain signals may be, retention and recycling of functional anti-tumor effector CD4$^+$ T cells within the tumor microenvironment greatly assists in achieving anti-tumor potency.

Compared to CD3ζ-mediated activation alone, CD4+ effector T cells expressing the IL13-CD28-41BBζ CAR exhibited augmented/sustained MAPK and AKT activity, upregulated Th$_1$ cytokine production, and enhanced cytolytic potency against tumor targets. Moreover, upon recursive stimulation with tumor, the IL13-CD28-41BBζ$^+$ CD4$^+$ cells retained/recycled their lytic function whereas IL13ζ$^+$ CD4$^+$ cells were effective, but sooner became anergic/exhausted. These in vitro observations correlated with enhanced in vivo control of established orthotopic CNS glioma xenografts in immunodeficient mice mediated by adoptively transferred ex vivo expanded CD4$^+$ T cells expressing the costimulatory CAR. These studies therefore demonstrate the effect of integrating costimulation with CD3ζ signaling events to fully activate CD4$^+$ anti-tumor effector cells for sustained function in the tumor microenvironment.

CD28 and 4-1BB costimulatory signals mediated via AKT can inhibit activation-induced cell death through up-regulation of anti-apoptotic proteins. The enhanced AKT activation seen in the IL13-CD28-41BBζ-expressing T cells was associated with enhanced recycling of tumor specific activity in vitro as well as prolonged tumor growth control in vivo. Thus, the costimulatory CAR can enhance the duration and/or retention of anti-tumor activity in a manner that can significantly improve the clinical efficacy of adoptive therapy protocols.

Tumor-specific CARs that contain their own costimulatory signaling domains provide a new approach for activating T lymphocytes against a wider variety of solid tumors that do not express these costimulatory ligands. IL13Rα2, for example, has been identified as an over-expressed cell-surface target on various human tumors, including breast cancer, head and neck cancer, kidney cancer, ovarian cancer and Kaposi's sarcoma as well as gliomas. Thus, T cells expressing a CAR that contains an IL13 zetakine and CD28 and 4-1BB can be used to treat glioblastomas (glioma) and any cancer, such as those listed above, that have the IL13 target on their surface.

The invention specifically contemplates CARs that contain CD3, CD28 and 4-1BB (and/or other costimulatory signaling domains) which can be directed to any tumor by incorporating a moiety that binds to a cell-surface-expressed tumor target, for example an antigen. Examples of other tumor-specific target binders include Her2/Neu (ErbB-2), α3 integrin, CD20, CD19, EGFRVIII, IL3Rα (CD123), LEA, CD44v6 or any target specific to a tumor, preferably a solid tumor that does not express the costimulatory signaling domain which is contained on the CAR. Therefore, constructs for targeting human tumors in this manner can include those with specificities for Her2/Neu (ErbB-2), α3 integrin, CD20, CD19, EGFRVIII, IL3Rα (CD123), LEA, CD44v6 or any specific tumor antigen or other cell-surface component accessible to binding by a chimeric T cell receptor. Persons of skill are aware of these specific tumor antigens and receptors which can be exploited to target a specific tumor, and are aware of the tumors that can be targeted in this manner.

Both CD4$^+$ and CD8$^+$ T cell effector functions can be triggered via these receptors, therefore both of these T cell types are contemplated for use with the invention. CD8$^+$ T cells expressing the IL13 CARs of this invention may be used to lyse target cells and to produce IL2 in the presence of target cells, among the other functions of these cells. Expression of the appropriate costimulatory CAR in either or both CD4$^+$ and CD8$^+$ T cells would be used to provide the most effective population of cells for adoptive immunotherapy, consisting therefore of either or both professional helper and killer T cells that exhibit enhanced and/or long term viability and anti-tumor activity.

All references cited in this specification are hereby incorporated by reference in their entirety. The following examples are solely for the purpose of illustrating one embodiment of the invention.

EXAMPLES

Example 1

Transfection and Expression of IL13Rα2-Specific Chimeric Receptors in Primary Human T Lymphocytes To engage both T cell receptor (TCR)- and costimulatory-like signaling cascades upon interaction with glioma tumor antigen IL13Rα2, signaling elements derived from CD28 and 4-1BB were integrated into an IL13-zetakine (IL13ζ) chimeric antigen receptor (CAR). The preferred IL13ζ CAR is composed of the extracellular IL13(E13Y) mutein, human IgG$_4$ hinge-Fc linked to the human cytoplasmic CD3ζ via the transmembrane domain of human CD4. See FIG. 1. De novo synthesis of the IL13(E13Y) coding sequence was performed using primers IL13P1, IL13P2, IL13P3, IL13P4, and IL13P5. See Table I, below, and FIG. 2. The final sequence (417 bp) was end-digested with EcoRI-BamHI, and ligated into the plasmid pSK (Stratagene™) as ligation 312#3. Ligation 312#3 was mutagenized (Stratagene™ kit, per manufacturer's instructions) to repair a deleted nucleotide using the primers IL13 312#3 mut5-3 and IL13 312#3 mut3-5 and ligation 312#3 as a template, to form ligation 348#1 (IL13ζ/pSK).

The human GM-CSFR alpha chain signal peptide (hsp) coding sequence was fused to the 5' end of IL13(E13Y) by standard PCR splice overlap extension. The hsp sequence was obtained from the template ligation 301#10 (hsp/pSK) using primers 5':19hsp5' and 3': hsp-IL13FR. See Table I. The IL13 sequence was obtained using the primers 5': hsp-IL13FF and 3': IL13-IgG4FR, and ligation 312#3 as template. See Table I.

A sequence encoding the IgG4 Fc, CD4 transmembrane and CD3ζ cytoplasmic regions (IgG4m:zeta; nucleotides 421-1512 of the complete IL13ζ sequence of FIG. 3 (SEQ ID NO:12)) was fused to the 3' end of the human signal peptide-IL13 fusion sequence using the same methods. The IgG4m:zeta sequence was obtained using the primers 5': IL13-IgG4FF and 3': ZetaN3' (see Table 1), using the sequence R9.10 (IgG4mZeta/pSK) as template. The 1119 bp IgG4m:zeta sequence was fused to the hsp-IL13 fusion sequence using the respective sequences as templates, and the primers 5': 19hsp5' and 3': ZetaN3' (see Table 1), to yield a 1522 bp hsp-IL13-IgG4m:zeta fusion sequence. The ends were digested with XbaI-NotI, and ligated into pSK as ligation 351#7, to create the plasmid IL13ζ/pSK (4464 bp) (i.e. the IL13ζ sequence of FIG. 3, within pSK cloning vector.

Figure 4:
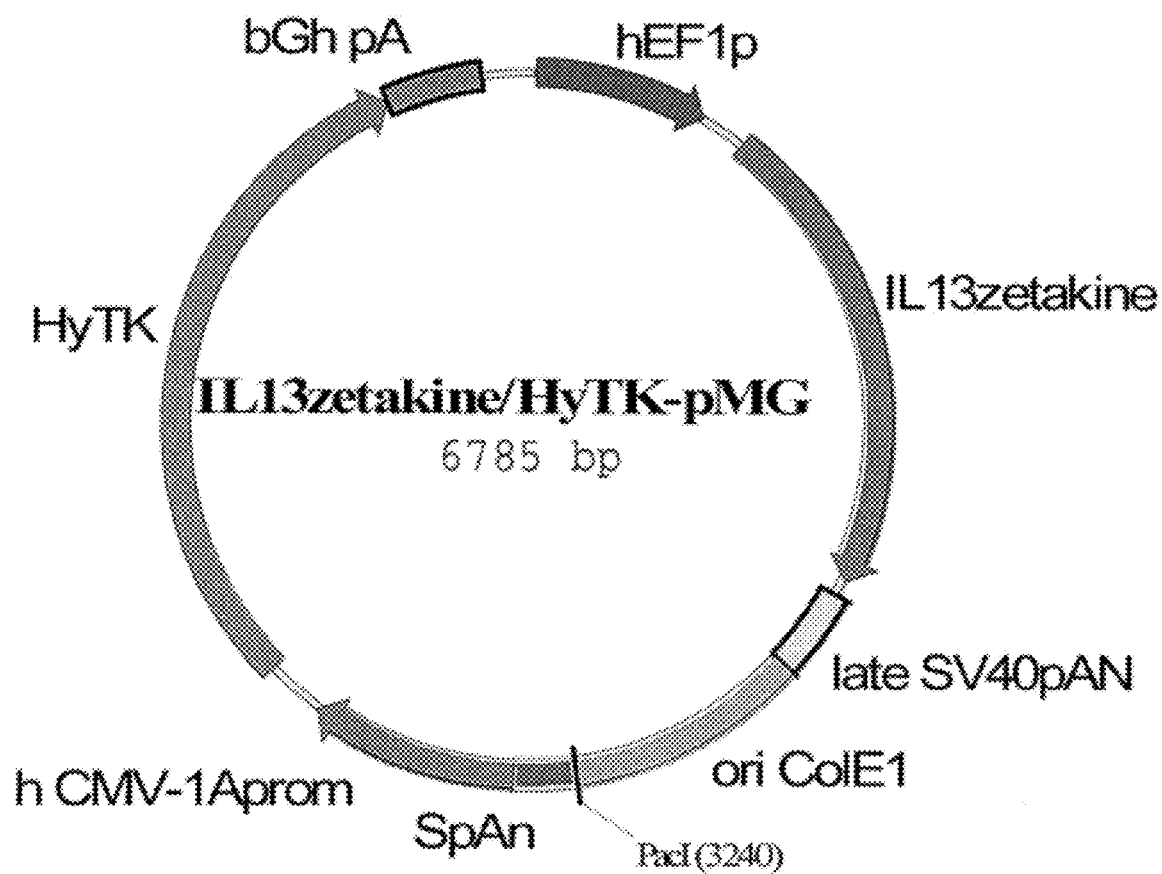
FIG. 4 is a map of the vector IL13zetakine/HyTK-pMG. An exemplary sequence of such a vector is provided in FIG. 5.

An expression vector containing the IL13ζ coding sequence was created by digesting IL13ζ/pSK with XbaI-NotI, and creating blunt ends with Klenow, and ligating the resulting fragment into the plasmid pMG^Pac (Invitrogen™) (first prepared by opening with SgrAI, blunting with Klenow, and dephosphorylation with SAP), to yield the plasmid IL13ζ/pMG. The hygromycin resistance region of IL13ζ/pMG was removed by digestion with NotI-NheI, and replaced by the selection/suicide fusion HyTK, obtained from plasmid CE7R/HyTK-pMG by digestion with NotI-NheI, to create the expression vector IL13ζ/HyTK-pMG (6785 bp). This plasmid comprises the human elongation factor-1a promoter (hEF1p) at bases 6-549, the IL13ζ coding sequence at bases 690-2183, the Simian Virus 40 Late polyadenylation signal (Late SV40pAN) at bases 2230-2498, a minimal E. coli origin of replication (Ori ColE1) at bases 2499-3245, a synthetic polyA and Pause site (SpAN) at bases 3246-3432, the Immediate-early CMV enhancer/promoter (hCMV-1Aprom) at bases 3453-4075, the Hygromycin resistance-Thymidine kinase coding region fusion (HyTK) at bases 4244-6319, and the bovine growth hormone polyadenylation signal and a transcription pause (BGh pAn) at bases 6320-6618. The plasmid has a PacI linearization site at bases 3233-3240. The hEF1p, late SV40pAN, on ColE1, SpAn, and hCMV-1Aprom elements all were derived from the parent plasmid pMG^Pac. In sum, IL13ζ/HyTK-pMG is a modified pMG backbone, expressing the IL13ζ gene from the hEF1promoter, and the HyTK fusion from the hCMV-1A promoter. A map of the plasmid IL13ζ/HyTK-pMG appears in FIG. 4. The full nucleic acid sequence of the plasmid is shown in FIGS. 5A-5L (SEQ ID NOs:13 and 14. The sequence of the IL13ζ insert also is given in FIG. 3 (SEQ ID NOs:5 and 6).

Assessment of the integrity of the expressed construct was confirmed by western blot using the anti-human CD3ζ monoclonal antibody clone 8D3 (BD PharMingen™, San Diego, Calif.) to probe whole cell lysates derived from Jurkat T cell stable transfectants cocultured in the presence or absence of tunicamycin, an inhibitor of glycosylation. Jurkat T cell stable transfectants (Jurkat-IL13-pMG bulk line) were obtained by electroporating Jurkat T cells with the IL13ζ/HyTK-pMG expression vector, followed by selection and expansion of positive transfectants. $2 \times 10^6$ cells from the Jurkat-IL13-pMG bulk line were plated per well in a 24-well plate with or without 5 μg/mL, 10 μg/mL, or 20 μg/mL Tunicamycin. The plate was incubated at 37° C. for 22 hours. Cells were harvested from each well, and each sample was washed with PBS and resuspended in 50 μL RIPA buffer (PBS, 1% NP40, 0.5% sodium deoxycholate, 0.1% SDS) containing protease inhibitor (1 tablet/10 mL Complete Protease Inhibitor Cocktail). Samples were incubated on ice for one hour, before being centrifuged at 4° C. for 20 minutes at 14,000 rpm. Samples of centrifuged lysate supernatant were harvested and boiled in a 1:3 volume of sample buffer under reducing conditions, then subjected to SDS-PAGE electrophoresis on a 12% acrylamide gel. Following transfer to nitrocellulose, the membrane then was blocked in a Blotto™ solution containing 4% non-fat dried milk in T-TBS (0.1% Tween 20™ in Tris buffered saline pH 8.0) for 1 hour. Membrane was then incubated with the primary mouse anti-human CD3ζ monoclonal antibody at a concentration of 0.5 μg/mL for one hour, washed, and then incubated with a 1:3000 dilution (in Blotto™ solution) of goat anti-mouse IgG alkaline phosphatase conjugated secondary antibody (Bio-Rad™ ImmunoStar™ Kit) for 1 hour. Prior to developing, the membrane was washed 4 additional times in T-TBS, and then incubated with 3 mL phosphatase substrate solution (Bio-Rad™ ImmunoStar™ Kit) for 5 minutes at room temperature. The membrane was then covered with a plastic development folder (Tropix™) and exposed to X-ray film. Consistent with the known glycosylation pattern of wild-type human IL13, the electrophoretic mobility of the expressed IL13(E13Y) zetakine indicates a heavily glycosylated protein which, when expressed in the presence of tunicamycin, is reduced to an amino acid backbone of approximately 54 kDa.

Construction of the co-stimulatory CAR was initiated with an HyTK-2A-IL13ζ-pcDNA3.1(+) construct, which encodes the selection/suicide fusion gene HyTK, the de novo synthesized self-cleavable foot-and-mouth disease 2A peptide (TCTAGAGGAGCATGCCAGCTGT-TGAATTTTGACCTTCTTAAGCTTGCGG-GAGACGTCGAGTCCAACCCTGGGCC; SEQ ID NO: 49), and the IL13ζ, molecule (FIG. 3), cloned into pcDNA3.1 (+) (Invitrogen™). To confer resistance to methotrexate (MTX), the HyTK gene was replaced by PCR with an dihydrofolate reductase (DHFR) gene (amplified from a cDNA library derived from peripheral blood mononuclear cells (PBMC) that had been stimulated for three days with the OKT3 antibody which recognizes the CD3 chain of the T cell receptor which contained L22F and F33S mutations generated using a QuikChange™ Site-Directed Mutagenesis Kit (Stratagene™). The resulting DHFRdm-2A-IL13ζ construct was then excised with NheI and NotI, eluted and ligated into the similarly digested mammalian plasmid expression vector pEK. The pEK vector had been modified originally from pcDNA3.1(+) by removing the CMV promoter and the ampicillin gene and replacing them with the human Elongation Factor 1α promoter (EF1p) gene derived from pMG (Invivogen™) to create the plasmid DHFRdm-2A-IL13ζ_pEK (pJ01275-9). CD28 cDNA was purchased from Invitrogen™ and 4-1BB coding region was amplified by PCR from a cDNA library derived from peripheral blood mononuclear cells (PBMC) that had been stimulated for three days with the OKT3 antibody (using primers 41BB5' and 41BB3', see Table 1).

Figure 6:
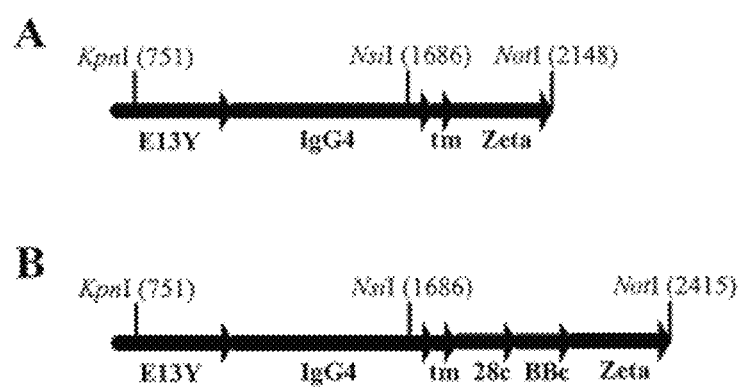
FIG. 6 contains two schematic representations of exemplary CAR linear plasmid constructs.

The intracellular signaling regions of CD28 and 4-1BB (amino acids 180-220 and 214-255, respectively, of the native CD28 and 4-1BB sequences) were fused by PCR (using the primers CD4-CD28F, CD28-4-1-BBR, CD28-4-1bbF, and 41bb93 provided in Table I) into the junction between the CD4 transmembrane and cytoplasmic CD3ζ (amino acids 52-164 of native CD3ζ) regions. See FIG. 6, which provides schematic representations of examples of IL13ζ (FIG. 6A) and IL13-CD28-41BBζ (FIG. 6B) linear plasmid constructs. The placement of human IL13 mutein (E13Y), human IgG$_4$ hinge-Fc (IgG$_4$), human CD4 transmembrane (tm), human CD3ζ cytoplasmic (Zeta), CD28 cytoplasmic (28c) and 4-1BB cytoplasmic (BBc) segments are indicated in FIG. 6. Restriction enzyme sites that were used to insert the different PCR fragments also are indicated in FIG. 6 (NheI, KpnI, NsiI, NotI), with their predicted base pair locations provided in parentheses. As shown in FIG. 6A, the CAR, IL13-CD28-41BBζ, comprises the cytoplasmic domain of CD28 and 4-1BB fused to that of CD3ζ. Each construct shown in FIG. 6A has a huIL13 domain containing the E13Y mutation which makes it IL13Rα2-specific, a human IgG$_4$ hinge-Fc domain (huγ$_4$Fc), a human CD4 transmembrane (huCD4tm) domain, and a human CD3ζ cytoplasmic (huCD3ζ cyt) domain; the IL13-CD28-41BBζ CAR has the signaling (sig)

domains of CD28 and 4-1BB inserted between the CD4 transmembrane and CD3ζ cytoplasmic domains. The PCR primers used in construction of the plasmids and used in expression analysis are provided in Table I.

Bulk cultures of CD4+ T cells obtained by MACS™ separation using the manufacturer's protocol (Miltenyi Biotec™ Inc.) were maintained in RPMI media with 10% FCS, 1% L-glutamine, 2.5% HEPES buffer, 50 U/mL rhIL2, 10 ng/mL rhIL15 and 0.1 μM MTX. Isolation, activation, and electroporation of human T cells was performed as follows. PBMC were isolated by density gradient centrifugation over Ficoll-Paque (Pharmacia Biotech™) of heparinized peripheral blood obtained from consenting healthy donors. The cells were resuspended in nucleofection solution using the Amaxa™ Human T cell Nucleofector kit (Amaxa™ Inc.). Plasmid (1 μg/5×10$^6$ cells) was added, and cells were electroporated using the Amaxa™ Nucleofector I (Amaxi™ Inc.), program U-14. Cells then were harvested in phenol red-free medium with 10% FCS, allowed to rest overnight, and then stimulated with 30 ng/mL OKT3 and 5 ng/mL rhIL15 in RPMI with 10% FCS for three days. Successful transfectants were selected using media containing 0.1 μM MTX and 5 ng/mL rhIL15.

Figure 7:
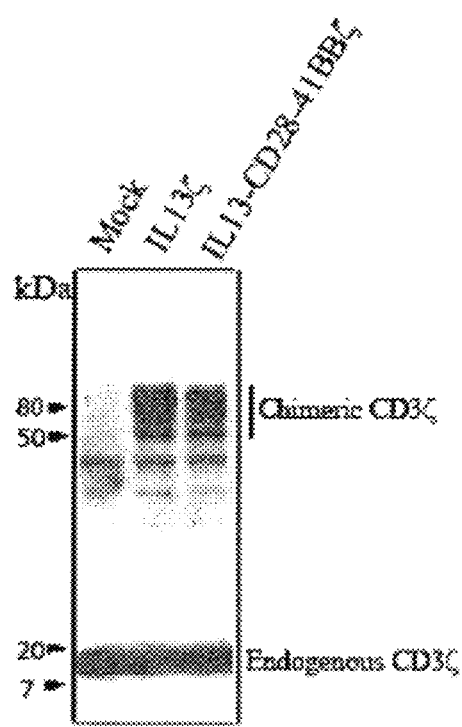
FIG. 7 shows western blot analysis of cell lysates derived from mock-, IL13ζ- and IL13-CD28-41BBζ-transfected CD4$^+$ T cells for CAR expression using a mouse anti-human CD3ζ specific mAb.

The expression of CARs was assessed by immunoblotting analysis with an antibody specific to CD3ζ. Whole cell lysates of bulk MTX-selected CD4+ T cells (mock-, IL13ζ- and IL13-CD28-41BBζ-transfected) were tested for the CAR expression (chimeric CD3ζ) using known methods and a commercially available mouse anti-human CD3ζ-specific monoclonal antibody, 1D3. As expected with such highly glycosylated proteins, multiple bands within the expected molecular weights were observed. See FIG. 7.

Figure 8:
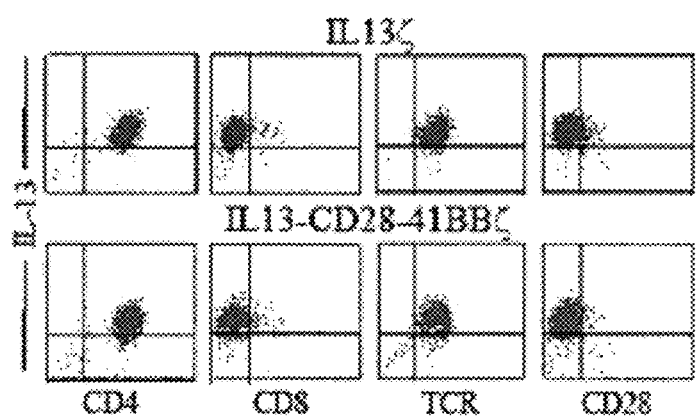
FIG. 8 is a panel of eight flow cytometry analyses that compare the cell surface phenotype of IL13ζ- and IL13-CD28-41BBζ-expressing bulk CD4$^+$ cells.

The levels of IL13ζ or IL13-CD28-41BBζ CAR expressed on the surface of CD4+ T cells were examined by detection of membrane-bound IL13 using flow cytometry. See FIG. 8. PBMC transfected with cDNA encoding IL13ζ or IL13-CD28-41BBζ CAR were propagated for an average of 10 weeks under selective concentrations of MTX (0.1 μM), magnetically sorted for CD4+ cells by MACS™ separation, and examined for surface expression of IL13-containing CAR (Y-axes), and CD4, CD8, TCRα/β, or CD28 (X-axes) as indicated. Isotype-matched fluorescent mAbs were used to establish the quadrants. These genetically modified T cell populations were not only predominantly CD4+ and CD8−, as expected after magnetic bead based MACS™ purification of CD4+ cells, but also expressed high and equivalent levels of endogenous TCR and low to undetectable levels of costimulatory CD28. See FIG. 8.

Figure 9:
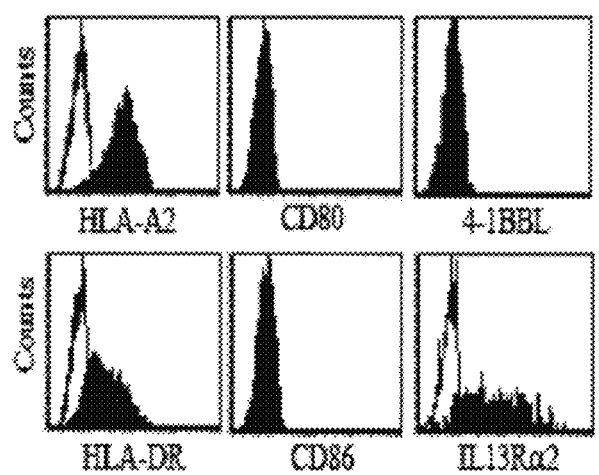
FIG. 9 is a panel of six graphs that show flow cytometry results of surface staining of HLA-A2 and HLA-DR (MHC molecules), IL13Rα2 and the costimulatory molecules CD80, CD86, and CD137-L (4-1BBL) (filled histograms) as indicated, compared to isotype controls (open histograms) on U87 glioma target cells.

The IL13Rα2+ human glioblastoma tumor cell target line used in these studies, U87, also was phenotyped to confirm that those cells express MHC class I and class II on their surface and do not express the costimulatory ligands CD80/86 or 4-1BBL. See FIG. 9, which shows the surface staining of MHC molecules HLA-A2 and HLA-DR, IL13R and costimulatory molecules CD80, CD86, and CD137-L (4-1BBL) (filled histograms) as indicated, compared to isotype controls (open histograms) on U87 glioma target cells, as analyzed by flow cytometry.

Flow cytometric analysis involved evaluating the cell-surface expression of the IL13-CAR constructs by staining with PE-conjugated or FITC-conjugated anti-human IL13 monoclonal antibodies (BD PharMingen™). The cell-surface phenotype of primary human T cell transfectants was assayed with FITC-conjugated anti-CD4, anti-CD8, and anti-TCR α/β antibodies or with PE-conjugated anti-CD28 antibodies (BD PharMingen™). The cell-surface phenotype of human U87 glioma cells was assayed with FITC-conjugated anti-HLA-A2, anti-HLA-DR, and anti-CD80 antibodies, or with PE-conjugated anti-CD86 and anti-CD137-L (4-1BBL) antibodies, compared to FITC- and PE-conjugated isotype controls (BD PharMingen™). IL13Rα2 expression was assayed using goat anti-human IL13Rα2 (R&D Systems™) followed by FITC-conjugated mouse anti-goat IgG (Jackson ImmunoResearch™)

TABLE I

PCR primers for CAR Construction.

| Primer Name | Primer Sequence (5'-3') | SEQ ID NO: |
|---|---|---|
| IL3P1 | TATGAATTCATGGCGCTTTTGTTGACCACGGTCATTGCTCTCACTTGCCTTGGCGGCTTTGCCTCCCCAGGCCCTGTGCCTCCCTCTACAGCCCTCAGGTAC | 17 |
| IL3P2 | GTTGATGCTCCATACCATGCTGCCATTGCAGAGCGGAGCCTTCTGGTTCTGGGTGATGTTGACCAGCTCCTCAATGAGGTACCTGAGGGCTGTAGAGGGAG | 18 |
| IL3P3 | CTCTGGGTCTTCTCGATGGCACTGCAGCCTGACACGTTGATCAGGGATTCCAGGGCTGCACAGTACATGCCAGCTGTCAGGTTGATGCTCCATACCATGC | 19 |
| IL3P4 | CCTCGATTTTGGTGTCTCGGACATGCAAGCTGGAAAACTGCCCAGCTGAGACCTTGTGCGGGCAGAATCCGCTCAGCATCCTCTGGGTCTTCTCGATGGC | 20 |
| IL3P5 | TCGGATCCTCAGTTGAACCGTCCCTCGCGAAAAAGTTTCTTTAAATGTAAGAGCAGGTCCTTTACAAACTGGGCCACCTCGATTTTGGTGTCTCGG | 21 |
| IL13 312#3 mut5-3 | CAACCTGACAGCTGGCATGTACTGTGCAGCCCTGGAATC | 22 |
| IL13 312#3 mut3-5 | GTTGGACTGTCGACCGTACATGACACGTCGGGACCTTAG | 23 |
| 5': 19hsp5' | ATCTCTAGAGCCGCCACCATGCTTCTCCTGGTGACAAGCCTTC | 24 |
| 3': hsp-IL13FR | GAGGGAGGCACAGGGCCTGGGATCAGGAGGAATG | 25 |

TABLE I-continued

PCR primers for CAR Construction.

| Primer Name | Primer Sequence (5'-3') | SEQ ID NO: |
|---|---|---|
| 5': hsp-IL13FF | CATTCCTCCTGATCCCAGGCCCTGTGCCTCCCTC | 26 |
| 3': IL13-IgG4FR | GGGACCATATTTGGACTCGTTGAACCGTCCCTCGC | 27 |
| 5': IL13-IgG4FF | GCGAGGGACGGTTCAACGAGTCCAAATATGGTCCC | 28 |
| 3': ZetaN3' | ATGCGGCCGCTCAGCGAGGGGGCAGG | 29 |
| 41BB5' | ATCGAATTCGCCGCCACCATGGGAAACAGCTGTTACAAC | 30 |
| 41BB3' | GATAAGCTTATCGATTCACCACATCCTCCTTCAGTT | 31 |
| CD4-CD28F | CATTGGGCTAGGCATCTTCTTCAGGAGTAAGAGGAGCAGGCTC | 32 |
| CD28-4-1BBR | GTTTCTTTCTGCCCCGTTTGCCACCTCCGGAGCGATAGGCTGCGAAG | 33 |
| CD28-4-1BBF | CTTCGCAGCCTATCGCTCCGGAGGTGGCAAACGGGGCAGAAAGAAAC | 34 |
| 4-1BB93' | GTTGCGGCCGCTCACAGTTCACATCCTCCTTCTTCTTC | 35 |

Example 2

Potentiation of JNK and p38 MAPK Signaling with Sustained AKT Signaling by IL13-CD28-41BBζ

T cells stimulated by the engagement of the TCR-CD3 complex along with the auxiliary receptors CD28 or 4-1BB are known to drive signals through AKT as well as the mitogen-activated protein kinases (MAPKs). To investigate the ability of costimulatory CARs to influence these downstream effector pathways, in vitro kinase assays were used to evaluate and compare the activity of AKT and MAPK family members ERK, JNK and p38 in IL13ζ- and IL13-CD28-41BBζ-expressing CD4$^+$ T cells following engagement of U87 target cells. Human glioma line, U87, was obtained from ATCC (Rockville, Md.). All tumor lines are adherent, and were grown in DMEM (Irvine Scientific™) supplemented with 10% heat-inactivated FCS, 25 mM HEPES, and 2 mM L-glutamine. CD4$^+$ T cells expressing IL13ζ or IL13-CD28-41BBζ CAR were incubated with U87 glioma cells for the times indicated in FIG. 10 prior to assay.

After IL13ζ- or IL13-CD28-41BBζ-expressing CD4$^+$ T cells were stimulated with tumor target cells for up to 48 hours (FIG. 10A) or 72 hours (FIG. 10B), levels of the JNK, p38 and AKT total protein substrates (i.e., cJun, ATF2, and GSK3, respectively) and the phosphorylated substrates (P-cJun, P-ATF2, and P-GSK3, respectively) were measured by Western immunoblot. The fold increase in the phosphorylation of each substrate, as a measure of kinase activity, is indicated at the bottom of each group in FIG. 10.

A non-radioactive solid-state kinase assay was performed using a method modified from Hibi et al., "Identification of an oncoprotein- and UV-responsive protein kinase that binds and potentiates the c-Jun activation domain." Genes Dev. 7:2135-2148, 1993. Using T cell lysates that had been separated from target cells by gentle centrifugation (1000 rpm, <3 minutes), the selected kinase was immunoprecipitated overnight at 4° C. using antibodies specific to ERK1/2, JNK, p38, and AKT (Cell Signaling Technology Inc.™). The immunoprecipitated complexes were washed in lysis buffer (PBS with 1% NP40, 0.1% SDS, and 0.5% sodium deoxycholate) and kinase buffer (25 mM Tris, pH 7.5, containing 10 mM MgCl$_2$ and 2 mM EGTA), and the assay was performed at 30° C. for 30 minutes, using 1 μg of substrate in the presence of 10 μM ATP.

Glutathione S transferase (GST) fusion proteins: GST-ELK, GST-ATF2 and GST-GSK3β (Cell Signaling Technology™ Inc.), and GST-cJun(1-79) (as described in Chang et al., Cell 124:601-613, 2006) were used as the substrates for the ERK, p38, AKT, and JNK kinase assays, respectively. The resulting products were resolved in 12% NuPAGE™ (Invitrogen™) according to standard methods and transferred to nitrocellulose membrane using the Xcell II Blot Module™ (Invitrogen™). The blots were probed with antibodies to phospho-ELK, ATF2, cJun and GSK3β (Cell Signaling Technology™ Inc.) to detect phosphorylated GST fusion proteins and antibodies to GST (BD PharMingen™) to detect the total amount of substrate. The immunoblots then were incubated with IRDye 680-conjugated rabbit or IRDye800-conjugated mouse immunoglobulin-specific antibodies (LI-COR™). Blocking buffer (purchased from LI-COR™) was used to pretreat blots and for antibody dilution. The blots were viewed and recorded using an Odyssey™ Infrared Imaging System (LI-COR™) and band intensities were quantitated using Odyssey™ v2.0 software (LI-COR™). Phosphorylation of substrate, a measure of kinase activity, was quantitated and normalized to corresponding detected amounts of immunoprecipitated kinase and total kinase substrate. Relative kinase activity of IL13ζ$^+$ CD4$^+$ T cells at t=0 was given an arbitrary value of 1.0; dashes (-) indicate fold differences <1.0 (see FIG. 10).

Figure 10:
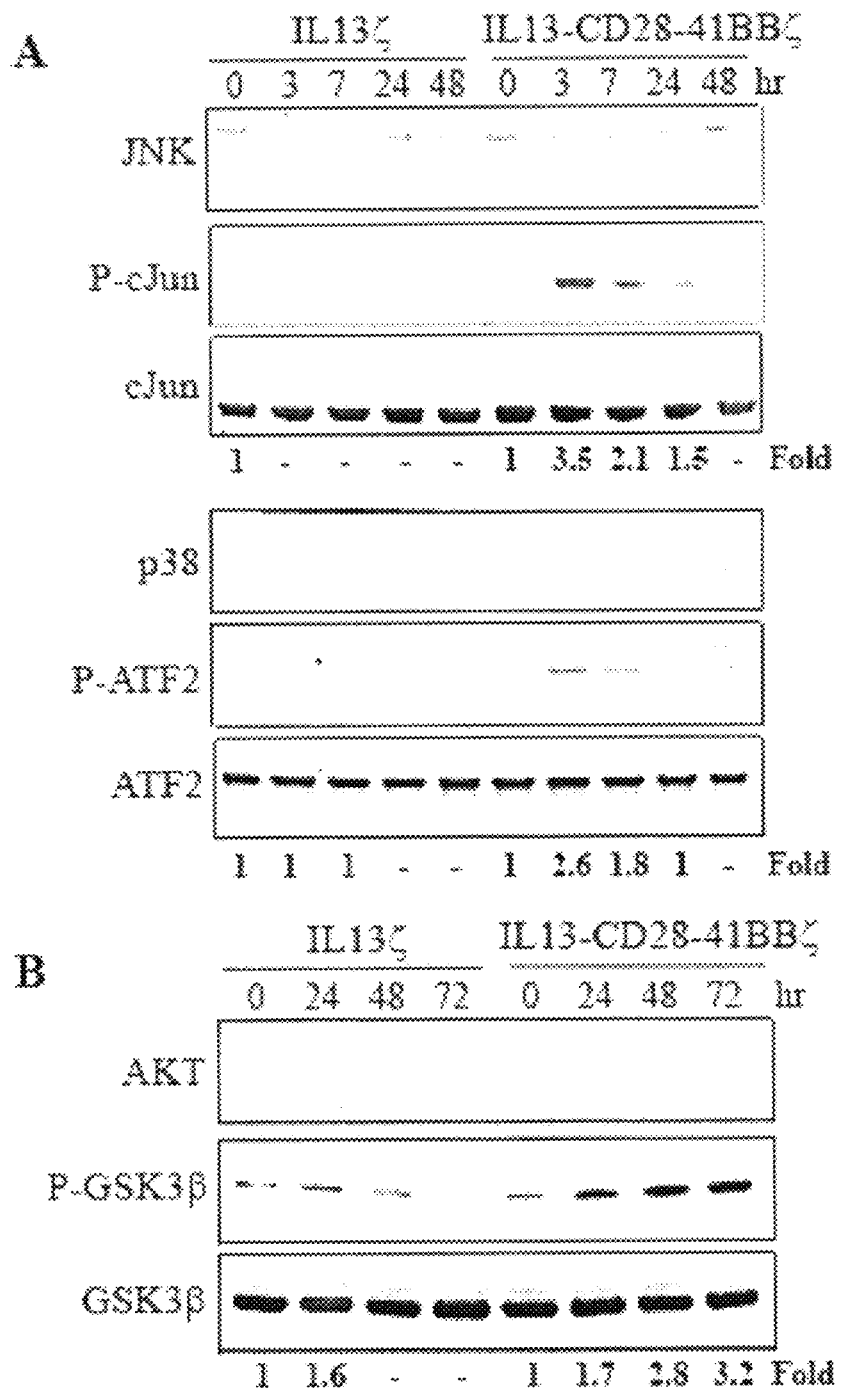
FIG. 10 is a series of immunoblots showing the results of a kinase assay to determine the kinetics of JNK and p38 (3A) and AKT (3B) activation, which is measured via phosphorylation of their respective substrates (i.e., P-cJun (phosphorylated c-Jun proto-oncogene), p-GSK3 (phosphorylated glycogen synthase kinase 3) and P-ATF2 (phosphorylated activating transcription factor 2)).

The kinase assay was able to detect enhanced JNK and p38 MAPK activity and prolonged AKT kinase activity in IL13-CD28-41BBζ$^+$ CD4$^+$ T cells after co-culture with U87 glioma cells. As shown in FIG. 10, JNK and p38 activation was stronger in CD4$^+$ T cells expressing IL13-CD28-41BBζ than in those expressing IL13ζ. See FIG. 10. In contrast, activation of another MAPK, ERK, was comparable between the two cell types. Activation of AKT was observed in both T cell populations, but was elevated only up to 24 hours in IL13ζ$^+$ cells while IL13-CD28-41BBζ cells displayed elevated AKT activity for up to 72 hours or more. See FIG. 10B. Thus, both CARs were effective, but the costimulatory domains within the IL13-CD28-41BBζ CAR produced more sustained AKT activity compared to that observed with the IL13ζ CAR.

Example 3

Figure 11:
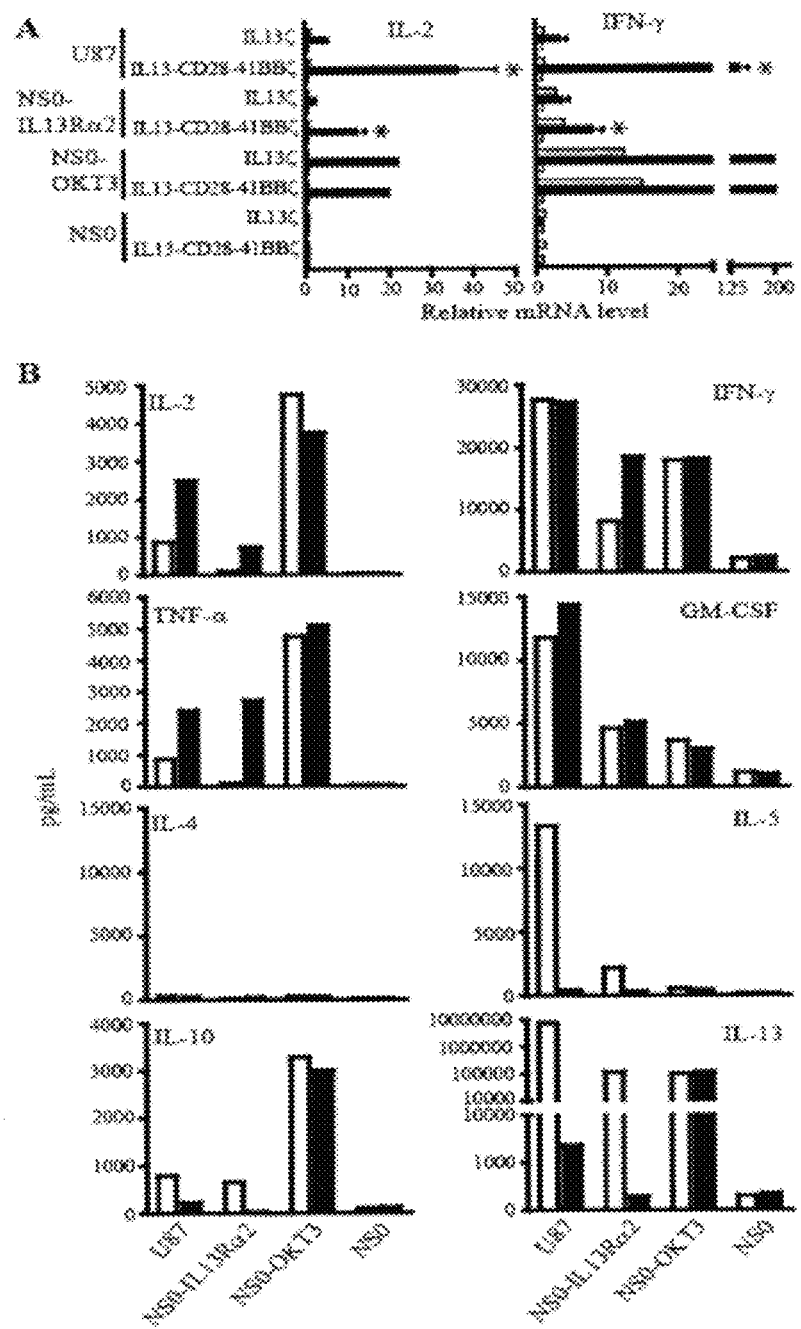
FIG. 11 shows the enhanced Th$_1$ polarization of IL13-CD28-41BBζ$^+$ CD4$^+$ T cells in terms of T cell Th$_1$ cytokine mRNA (FIG. 11A) and Th$_1$ and Th$_2$ cytokine protein production (FIG. 11B).

Costimulation Signals Enforce $Th_1$ Polarization of Tumor Re-Directed $CD4^+$ Effectors Because p38 activity has been detected in $Th_1$ but not $Th_2$ cells, and JNK/p38 activation is known to induce $Th_1$ production of associated TNF-α and IFN-γ cytokines, the effect of CD28 and 4-1BB costimulatory function on CAR-mediated induction of $Th_1$-associated cytokines was investigated. Genetically modified $CD4^+$ T cells ($10^6$ cells) expressing IL13ζ or IL13-CD28-41BBζ were co-cultured in 24-well tissue culture plates with different stimulator cells ($5\times10^5$ cells) in 2 mL of culture medium. The stimulator cells were U87 glioma cells (U87), parental NS0 mouse myeloma cells (NS0), NS0 cells stably expressing surface IL13Rα2 (NS0-IL13Rα2) or NS0 cells stably expressing membrane bound OKT3 (NS0-OKT3) as indicated in FIG. 11A.

Real-time quantitative RT-PCR (qPCR) was used to measure relative mRNA levels after culture. For gene expression analysis, total cellular RNA of the $CD4^+$ T cell transfectants was isolated using an RNeasy™ kit (Qiagen™). Reverse transcription of 5 µg total RNA in a volume of 30 mL (containing 1× reverse transcriptase buffer, 2.5 mM oligo dT, 0.25 mM dNTP, 0.01 M dithiothreitol, 20 U of Rnasin and 200 U of SuperScript™ II RNase H⁻ reverse transcriptase (Invitrogen™)) was used to synthesize cDNA. Samples were incubated at 42° C. for 1 hour and the reverse transcriptase then was inactivated by heating 5 minutes at 70° C. Resulting cDNA, equivalent to 0.2 µg of total RNA, was subjected to qPCR analysis using SYBR Green™ PCR master mix (Applied Biosystems™) and designed primers by DNA Engine Opticon 2™ real time PCR detection system (MJ Research Inc.™). Primer sequences of the tested genes IL2 and IFN-γ are as follows: IL2 forward: CAAGAATCCCAAACTCAC-CAG, SEQ ID NO: 50; IL2 reverse: CGTTGATATTGCT-GATTAAGTCC, SEQ ID NO: 51; IFN-γ forward: ATC-CCAGTAATGGTTGTCCTGCCT, SEQ ID NO: 52; IFN-γ reverse: TCTTGCTTAGGTTGGCTGCCTAGT, SEQ ID NO: 53. The average cycle threshold value (CT) of cyclophilin mRNA (as described in Chang et al., "The E3 ubiquitin ligase itch couples JAK activation to TNFalpha-induced cell death by inducing c-FLIP(L) turnover." Cell 124:601-613, 2006) was used to normalize the tested genes. The average CT values were determined by triplicate qPCR measurements for each gene in each experimental condition.

T cell total mRNA was collected at 0 hours (FIG. 11A, white bars), 7 hours (FIG. 11A, black bars) and 24 hours (FIG. 11A, shaded bars) for qPCR analysis of the indicated human mRNAs. * indicates a p<0.05 when compared to 7 hour values of IL13ζ-expressing $CD4^+$ T cells using an unpaired Student's t-test. The mouse myeloma line NS0 was electroporated with either IL13Rα2-IMPDH2_pMG (pJ00659), which confers expression of the IL13Rα2 target antigen and resistance to mycophenolic acid (MPA) or OKT3-IMPDH2_pcDNA3.1(+) (pJ01056), which confers expression of the CD3-crosslinking (and thus T cell stimulatory) OKT3 molecule along with resistance to MPA, and then cloned in the presence of 6 µM mycophenolic acid (MPA) and screened for human IL13Rα2 transgene expression. For the experiments using U87 and NS0-IL13Rα2 tumor cells, n=3; for the experiment using NS0-OKT3 and NS0 tumor cells, n=1.

The levels of IL2 and INF-γ mRNA were higher in IL13-CD28-41BBζ⁺ T cells than in IL13ζ+ T cells after culture with U87 glioblastoma cells. See FIG. 11A. No IL2 or INF-γ mRNA induction was observed with either T cell population when co-cultured with NS0 cells. Stimulation by IL13Rα2 transgene-expressing NS0 cells restored IL2 and INF-γ mRNA induction in IL13-CD28-41BBζ– but not in IL13ζ–expressing T cells, indicating that cytokine induction genes were IL13Rα2-dependent. The relative amounts of induced IL2 and INF-γ mRNA directly correlate with IL13Rα2 surface expression levels on U87 and transgene expressing-NS0 cells; the U87 level is higher than that of NS0-IL13Rα2 cells. In contrast, induction of the IL2 and INF-γ genes in IL13ζ⁺ T cells was similar to that seen in IL13-CD28-41BBζ⁺ T cells when each population was co-cultured with NS0 cells that stably expressed membrane bound OKT3, an agonist immunoglobulin molecule that activates T cells via engagement of CD3ε. These results indicate that the lower induction of IL2 and INF-γ mRNA mediated by the engagement of IL13ζ with IL13Rα2 is not due to an intrinsic defect in these T cells, but to the lack of CD28 and 4-1BB costimulatory domains within the CAR.

To quantitate the amounts of $Th_1$ versus $Th_2$ cytokine proteins released from these CAR-expressing T cells, supernatants from these co-cultures were assayed for cytokine content. After a 24-hour incubation, culture supernatants of IL13ζ⁺ (white bars) or IL13-CD28-41BBζ⁺ (black bars) were harvested and assayed for $Th_1$ and $Th_2$ cytokines by multiplex cytometric bead array using the human 17-Plex Panel™ kit per the manufacturer's instructions (Bio-Rad™ Laboratories). See FIG. 11B.

U87 glioma or IL13Rα2⁺ NS0 cells stimulated more $Th_1$ cytokine release (IL2, IFN-γ, TNF-α and GM-CSF) and less $Th_2$ cytokine release (IL5, IL10 and IL13) from IL13-CD28-41BBζ⁺ T cells than from IL13ζ⁺ T cells. Equivalent levels of $Th_1$ and $Th_2$ cytokines were produced by IL13ζ- and IL13-CD28-41BBζ-expressing $CD4^+$ T cells cultured with OKT3 expressing NS0 cells, indicating that these cells remain unpolarized upon polyclonal activation via endogenous CD3. Levels of cytokines were all low to undetectable when the T cells were cultured with parental NS0 cells. Levels of the $Th_2$ cytokine IL4 also were low to undetectable when the T cells were cultured with any of the tumor cell lines. Overall, these data show that the presence of CD28 and 4-1BB costimulatory domains within the CAR help drive $CD4^+$ T cell transcription and secretion of $Th_1$-like cytokines.

Example 4

Increase in Recycling Anti-Tumor Lytic Activity in IL13-CD28-41BBζ⁺ $CD4^+$ T cells To determine if costimulatory CAR affected the tumor specific cytotoxic activity of $CD4^+$ T cells, luminescent cytolytic assays (LCA) were performed to detect the firefly luciferase (ffLuc) transgene luminescence activity of tumor cells in vitro. This assay was performed as described by Brown et al., "Biophotonic cytotoxicity assay for high-throughput screening of cytolytic killing." J. Immunol. Meth. 297:39-52, 2005, with 0.14 mg/mL D-luciferin and using a Victor2™ Luminometer. Briefly, ffLuc transgene luminescence activity of tumor cells in vitro was analyzed by LCA with 0.14 mg/mL D-luciferin (Xeonogen™) using a Victor2™ luminometer. See FIG. 12A, which shows enhanced cytotoxic activity of IL13-CD28-41BBζ⁺ $CD4^+$ T cells (■) against U87 targets compared to IL13ζ⁺ $CD4^+$ T cells (○) at the indicated E:T ratio after 4 hours. The mean±SE of triplicate values are indicated; * indicates a p<0.05 using an unpaired Student's t-test.

After 4 hours of co-culture with ffLuc-transfected U87 target cells, IL13-CD28-41BBζ+ cells displayed a statistically significant enhancement in lytic activity compared to IL13ζ+ cells. If co-culture was extended to 48 hours, no difference in cytotoxic activity was observed between the IL13ζ- and IL13-CD28-41BBζ-expressing cells (100% specific lysis was reached with both cells). The data in FIG. 12B indicate specific lysis by LCA assay after 48 hours of co-culture at an E:T ratio of 2:1, and then again after addition of fresh targets for another 48 hours of co-culture at an E:T ratio of 2:1. The mean±SE of triplicate values are indicated; * indicates a p<0.05 (paired Student's t-test) comparing IL13-CD28-41BB+ CD4+ T cells (black bars) to IL13ζ+ CD4+ T cells (white bars) in the indicated co-culture.

Figure 12:
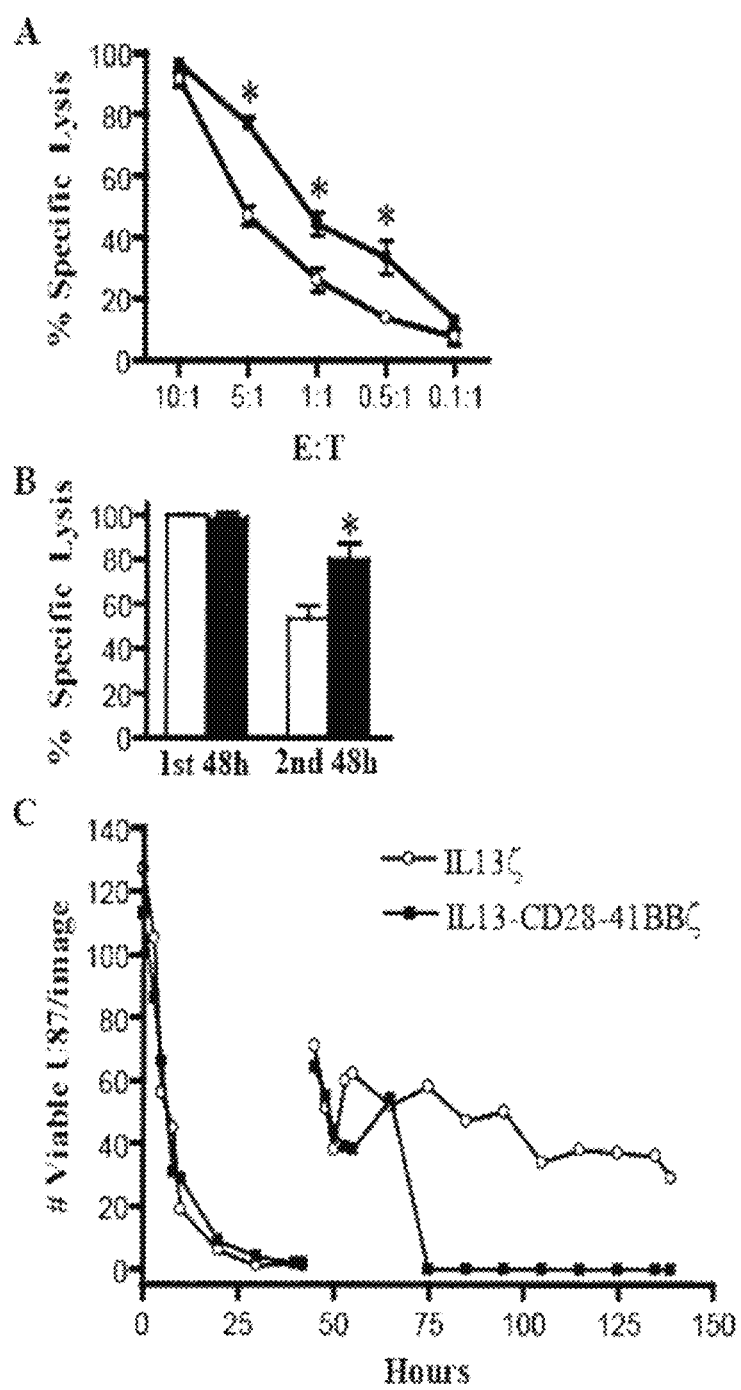
FIG. 12A provides data showing enhanced cytotoxic activity of IL13-CD28-41BBζ$^+$ CD4$^+$ T cells (■) against U87 targets compared to that of IL13ζ$^+$ CD4$^+$ T cells (○) at the indicated E:T ratio in a 4 hour luciferase cytotoxicity assay (LCA).
FIG. 12B shows similar data for IL13-CD28-41BBζ$^+$ CD4$^+$ T cells (black bars) and IL13ζ$^+$ CD4$^+$ T cells (white bars) co-cultured for 48 hours at an E:T ratio of 2:1, and then again co-cultured for an additional 48 hours after addition of fresh targets at the same E:T ratio.
FIG. 12C provides data obtained with video imaging of T cells expressing the indicated CAR co-cultured with adherent U87 cells, which indicates the number of viable cells per image.

Perforin and granzyme B mRNA levels were equally upregulated in IL13ζ+ and IL13-CD28-41BBζ+ cells, suggesting that these CAR-expressing T cells can use similar mechanisms of killing. However, if fresh ffLuc+ targets were added for a second round of 48 hour co-culture with the same CAR-expressing CD4+ T cells, the IL13-CD28-41BBζ+ cells displayed significantly higher lytic activity than IL13ζ+ cells (FIG. 12B). This suggests that the costimulatory CAR beneficially affects the duration and/or recycling of CD4+ T cell killing activity.

To further examine this phenomenon, viability of U87 tumor cells was analyzed during co-culture with IL13ζ+ or IL13-CD28-41BBζ+ T cells using video time-lapse microscopy (VTLM) of co-cultures of 6×10^5 adherent U87 glioma cells with 1.2×10^6 IL13ζ- or IL13-CD28-41BBζ-expressing CD4+ T cells. The cultures were washed 45 hours later and then re-cultured with fresh U87 glioma cells (6×10^6). Numbers of viable tumor cells were plotted over 42 hours (the first killing) and from 45 hours to 139 hours (the second killing). See FIG. 12C.

Imaging was simultaneously undertaken in a 37° C. warm room on four Eclipse TS100™ microscopes (Nikon™ Inc.), each equipped with a tungsten-halogen lamp, GIF (green) filter, ELWD 0.3 NA condenser, Plan Fluor™ 4×/0.13 PhL DL infinity corrected objective lens, D10NLC 1× lensless C-mount adapter (Diagnostic Instruments™) and VCB-3524 B/W RS-170 video ½" CCD camera (Sanyo™ North America Corp.). To collect the data, 1.2×10^6 T cells (in 200 μL Hank's balanced salt solution supplemented with 0.1% human serum albumin) were added to T-25 flasks containing 6×10^5 adherent U87 cells (plated 1 day prior at 3×10^5 cells/flask). The flasks were allowed to equilibrate on the microscope stage for 30 minutes prior to imaging. Time-lapse acquisition rate was at 2-minute intervals. Several frames of tumor cells alone were acquired in each video, followed by addition of T cells, The combined cells then were recorded continuously for 80 hours. After adding the T cells, each flask was gassed with 5% $CO_2$ for 10 seconds and sealed with parafilm to insure good pH control (bicarbonate in HBSS) and stable focus, respectively. Images were acquired using the COH VTLF Camera Organizer and digitized at 640×480 pixels using a Matrox™ 4-channel frame grabber board. Viable tumor cell counts were performed at <10 hour intervals using the "Manually Count Objects" command in MetaMorph™ 6.33 (Universal Imaging/Molecular Devices™ Corp.). All datasets were imported into MetaMorph™ and saved as MetaMorph™ stacks and AVI movies.

The capacity of either of the genetically modified CD4+ T cells to kill tumor cells during the first 42 hours of co-culture was substantially the same (almost 100% of the U87 cells were killed by 30 hours). However, in the second encounter with U87 tumor cells, the recovered IL13-CD28-41BBζ+ T cells retained greater cytolytic activity than the IL13ζ+ T cells. Importantly, enumeration of T cells prior to addition of U87 cells for a second time revealed that there were no significant differences in cell number. Furthermore, CFSE-based assays performed over 72 hours of co-culture with U87 cells revealed no differences in proliferation of IL13ζ+ or IL13-CD28-41BBζ+ T cells in vitro. This demonstrates that the greater cytolytic activity upon addition of fresh targets was not due to the presence of more killers, but to an enhanced ability of individual killers to function. Together, these data show that the costimulatory CAR supports the recycling and retention of CD4+ T cell function.

Example 5

Enhanced In Vivo Tumor Clearance by IL13-CD28-41BBζ+ CD4+ T Cells

The ability of CARs with CD28 and 4-1BB signaling domains to enhance the anti-tumor efficacy of CD4+ T cells was assessed using established U87 tumors in an orthotopic murine xenograft model. For in vivo studies, the U87 cells were transfected with ffluc-zeocin_pcDNA3.1(+) (pJ00778, a plasmid expressing a protein fusion of the firefly luciferase enzyme and the zeocin drug resistance gene) and IL2(2)_HyTk-pMG (pJ00976, a plasmid expressing the IL2 cytokine and the selection/suicide fusion gene HyTK) using oligofectimine (Invitrogen™) according to the manufacturer's instructions and then cloned in the presence of 0.2 mg/mL Zeocin and 0.1 mg/mL Hygromycin.

To produce the orthotopic glioma xenograft model, mice were treated as follows. One day after irradiation with 250 rads, male 6- to 8-week-old NOD-scid mice were anesthetized, shaved and immobilized in a Cunningham™ Mouse/Neonatal Rat Adaptor stereotactic apparatus restraint (Stoelting™). Mice then received a stereotactically guided injection of tumor (U87 glioma) 2 mm lateral and 0.5 mm anterior to Bregma over 3-5 mm. U87-ffLucZeo/IL2+ tumor cells (2×10^5 cells/mouse), suspended in 2 μL of phenol-free RPMI (Irvine Scientific, Irvine, Calif.), were injected at a depth of 2.5 mm from the dura. Seven days after tumor inoculation, 10^6 T cells expressing either IL13ζ or IL13-CD28-41BBζ were delivered (adoptively transferred) in 2 μL to the tumor coordinates in the cerebrum. Control animals received PBS only ("sham control"). Burr holes were sealed with bone-wax and the incision closed with Nexaband™ glue. Animals received a subcutaneous injection of 0.1 mg/kg Buprenex™ for post-surgical recovery. In this model, tumors start to spontaneously regress at 13-14 days after injection due to recovery of the endogenous immune system, so experiments were completed by day 12.

Orthotopic tumor growth can be quantitated noninvasively by monitoring ffLuc flux signals derived from tumors in established U87 glioblastoma cells that stably express firefly luciferase (ffLuc) and human IL2. The in vivo luciferase activity was detected using in vivo biophotonic tumor imaging in mice with the Xenogen™ In Vivo Imaging System (IVIS) as previously described by Kahlon et al., "Specific recognition and killing of glioblastoma multiforme by interleukin 13-zetakine redirected cytolytic T cells." Cancer Res. 64:9160-9166, 2004. Briefly, to monitor ffLuc flux, mice were injected intraperitoneally with 4.29 mg D-luciferin, anesthetized (1.5 L/min Oxygen+4% Isoflurane), and light emission was measured over an integration time of 1 minute at 14 minutes post injection of luciferin. The flux (photons/ second) was quantitated as total counts measured over time in the region of interest. See results in FIG. 13. The values on the Y-axis represent the mean I SD of total flux levels of ffLuc$^+$ tumors from sham and treated groups (n=6 for each group) at the indicated days after tumor engraftment. "Tx" indicates treatment with adoptively transferred T cells.

Figure 13:
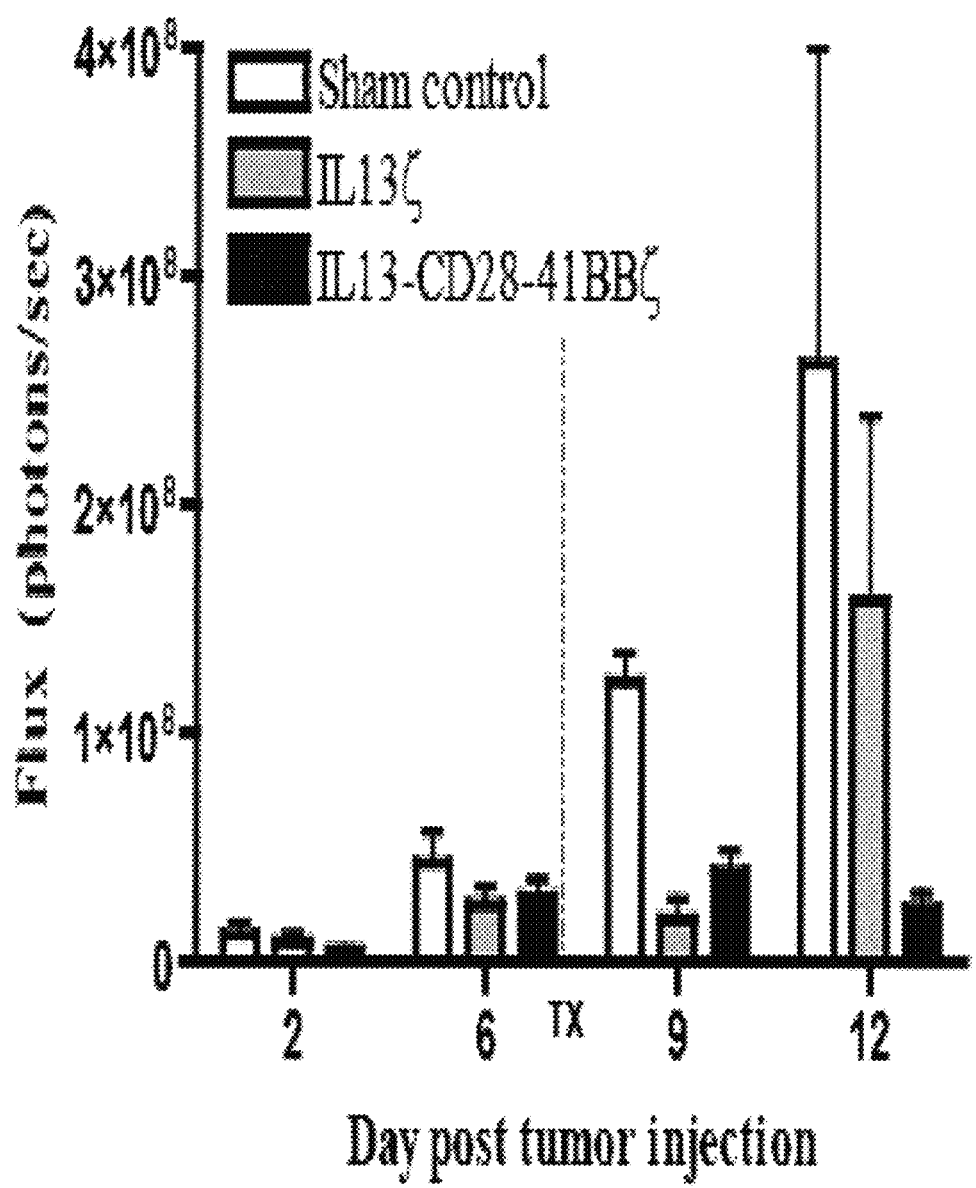
FIG. 13 provides flux data showing sustained anti-tumor effect against established glioblastoma xenografts in vivo by IL13-CD28-41BBζ$^+$ CD4$^+$ T cells. Results observed with IL13ζ- and sham-transfected T cells also are shown.

Prior to adoptive transfer of CAR-expressing CD4$^+$ T cells, all the mice exhibited increasing levels of tumor-derived ffLuc flux signals as expected (see FIG. 13; compare days 2 and 6 after tumor engraftment). Two days following adoptive transfer (Tx), tumor ffLuc flux levels were reduced in the mice treated with either IL1 or IL13-CD28-41BBζ-expressing T cells, when compared to the sham treated mice. However, 5 days post T cell treatment (day 12 after engraftment), tumor flux signals in the mice treated with IL13-CD28-41BBζ$^+$ T cells remained low, while flux signals from mice treated with IL13ζ$^+$ T cells had increased to a level similar to that of the sham treated (control) group. The costimulatory signaling domains of CD28 and 4-1BB thus enhanced and/or prolonged tumor growth control by the genetically re-directed T cells.

Example 6

Preparation of T Cells Suitable for Therapy

T lymphocytes were obtained from a patient by leukopheresis, and the autologous T cells were genetically altered to express the CAR, then administered back to the patient to achieve anti-cancer therapy.

To prepare IL13ζ$^+$ T cells suitable for therapeutic use, mononuclear cells were separated from leukopheresed blood by centrifugation over clinical grade Ficoll™ PBMC were washed twice in sterile phosphate-buffered saline containing 0.526 mM EDTA and then once in sterile PBS, and suspended in culture media consisting of RPMI 1640 HEPES, 10% heat inactivated FCS, and 4 mM L-glutamine. T cells present in patient PBMC were polyclonally activated by addition of Orthoclone™ OKT3 (30 ng/mL) to the culture. Cell cultures then were incubated in vented T-75 tissue culture flasks in the study subject's designated incubator. Twenty-four hours after initiation of culture, rhIL2 was added at 25 U/mL. Three days after the initiation of culture, PBMC were harvested, centrifuged, and resuspended in hypotonic electroporation buffer at $20 \times 10^6$ cells/mL. Twenty-five micrograms of the plasmid IL13ζ/HyTK-pMG, together with 400 µL of cell suspension, were added to a sterile 0.2 cm electroporation cuvette. Each cuvette was subjected to a single electrical pulse of 250V/40 µs and again incubated for ten minutes at room temperature. Surviving cells were harvested from cuvettes, pooled, and resuspended in culture media containing 25 U/mL rhIL2. Flasks were placed in the patient's designated tissue culture incubator. Three days following electroporation, hygromycin was added to cells at a final concentration of 0.2 mg/mL. Electroporated PBMC were cultured for a total of 14 days with media and IL2 supplementation every 48 hours.

The cloning of hygromycin-resistant CD8$^+$ CTL from electroporated OKT3-activated patient PBMC was initiated on day 14 of culture. Briefly, viable patient PBMC were added to a mixture of $100 \times 10^6$ cryopreserved irradiated feeder PBMC and $20 \times 10^6$ irradiated TM-LCL (EBV-transformed lymphoblastoid cells that act as feeder cells) in a volume of 200 mL of culture media containing 30 ng/mL OKT3 and 50 U/mL rhIL2. This mix was plated 0.2 mL into each well of ten 96-well cloning plates. Plates were wrapped in aluminum foil to decrease evaporative loss and placed in the patient's designated tissue culture incubator. On day 19 of culture, each well received hygromycin to a final concentration of 0.2 mg/mL. Wells were visually inspected for cellular outgrowth on an inverted microscope at Day 30 and positive wells were marked for restimulation.

The contents of each cloning well with cell growth were individually transferred to T-25 flasks containing $50 \times 10^6$ irradiated PBMC, $10 \times 10^6$ irradiated LCL, and 30 ng/mL OKT3 in 25 mL tissue culture media. On days 1, 3, 5, 7, 9, 11, and/or 13 after restimulation, flasks received 50 U/mL rhIL2 and 15 mL fresh media when needed. On day 5 of the stimulation cycle, flasks also were supplemented with hygromycin 0.2 mg/mL. Fourteen days after seeding, cells were harvested, counted, and restimulated in T-75 flasks containing $100 \times 10^6$ irradiated PBMC, $20 \times 10^6$ irradiated TM-LCL and 30 ng/mL OKT3 in 50 mL tissue culture media. Flasks received additions to culture of rhIL2 and hygromycin as outlined above.

CTL selected for expansion for possible use in therapy were analyzed by immunofluorescence on a fluorescence-activated cell sorter, using FITC-conjugated monoclonal antibodies WT/31 (αβTCR), Leu 2a (CD8), and OKT4 (CD4) to confirm the clone phenotype (αβTCR$^+$, CD4$^-$, CD8$^+$, and IL13$^+$). Criteria for selection of clones for clinical use included uniform TCR αβ$^+$, CD4$^-$, CD8$^+$ and IL13$^+$ as compared to isotype control FITC/PE-conjugated antibody. A single site of plasmid vector chromosomal integration was confirmed by Southern blot analysis. DNA from genetically modified T cell clones were screened with a DNA probe specific for the plasmid vector.

Expression of IL13-CD28-41BBζ was determined by western blot to detect chimeric receptor protein using the anti-CD3ζ zeta chain antibody described above according to standard methods. Briefly, whole cell lysates of transfected T cell clones were generated by lysis of $2 \times 10^7$ washed cells in 1 mL RIPA buffer (PBS, 1% NP40, 0.5% sodium deoxycholate, 0.1% SDS) containing 1 tablet/10 mL Complete Protease Inhibitor Cocktail. After an 80-minute incubation on ice, aliquots of centrifuged whole cell lysate supernatant were harvested and boiled in an equal volume of loading buffer under reducing conditions then subjected to SDS-PAGE electrophoresis on a precast 12% acrylamide gel. Following transfer to nitrocellulose, the membrane then was blocked in Blotto™ solution containing 4% non-fat dried milk in T-TBS (0.1% Tween 20™ in Tris buffered saline, pH 8.0) for one hour. Membranes were washed in T-TBS, then incubated with primary mouse anti-human CD3ζ monoclonal antibody 8D3 (Pharmingen™) at a concentration of 0.5 µg/mL for one hour. Following an additional four washes in T-TBS, membranes were incubated with a 1:3000 dilution (in Blotto™ solution) of goat anti-mouse IgG alkaline phosphatase-conjugated secondary antibody for 1 hour. Prior to adding substrate, membranes were rinsed in T-TBS, then incubated with 3 mL phosphatase substrate solution (Bio-Rad™ ImmunoStar™ kit) according to the manufacturer's instructions.

Suitable doses for a therapeutic effect are between about $10^6$ and about $10^9$ cells per dose, preferably in a series of dosing cycles. A preferred dosing regimen consists of four one-week dosing cycles of escalating doses, starting at about $10^7$ cells on Day 0, increasing incrementally up to a target dose of about $10^8$ cells by Day 5. Suitable modes of administration include intravenous, subcutaneous, intracavitary (for example by reservoir-access device), intraperitoneal, and direct injection into a tumor mass.

Example 7

Treatment of Intracranial Recurrent Glioma in Human Patients

Treatment of glioma or any other cancer as described herein using IL13-CD28-41BBζ-expressing T cells according to this invention was performed as follows. T cell clones, preferably as described in Example 6, were selected for:

a. TCRα/β+, CD4−, CD8+, IL13+ cell surface phenotype;
b. the presence of a single copy of chromosomally integrated plasmid vector DNA;
c. expression of the IL13-CD28-41BBζ protein;
d. specific lysis of human IL13Rα2+ targets;
e. dependence on exogenous IL2 for in vitro growth;
f. mycoplasma, fungal and bacterial sterility and endotoxin levels less than 5 EU/mL; and
g. in vitro sensitivity of clones to ganciclovir.

Peripheral blood mononuclear cells were obtained from the patient by leukopheresis, preferably following recovery from initial resection surgery and at a time at least three weeks from tapering off steroids and/or their most recent systemic chemotherapy. The target leukopheresis mononuclear cell yield generally was 5×10$^9$ and the target number of hygromycin-resistant cytolytic T cell clones was 25. In general, at least five clones were identified that met all quality control parameters for in vitro expansion. Clones were cryopreserved and patients monitored by serial radiographic and clinical examinations. When recurrence of progression of disease was documented, patients underwent a re-resection and/or placement of a reservoir-access device for delivering T cells to the tumor resection cavity.

Following recovery from surgery and tapering of steroids, if applicable, the patient commenced T cell therapy as follows. The patient received a target of at least four one-week cycles of therapy. During the first cycle, cell dose escalation proceeded from an initial dose on Day 0 of about 10$^7$ cells, followed by about 5×10$^7$ cells on Day 3 to a target dose of about 10$^8$ cells on Day 5. Cycle 2 commenced as early as one week from commencement of cycle 1. On the days of T cell administration, expanded clones were aseptically processed by washing twice in 50 cc of PBS then resuspended in pharmaceutical preservative-free normal saline in a volume that resulted in the cell dose for patient delivery in 2 mL. Preferably, T cells were instilled over 5-10 minutes, followed by a 2 mL PFNS flush administered over 5 minutes. Response to therapy was assessed by MRI +/− gandolinium, with spectroscopy.

In general, cell doses were at least a log less than doses given in studies employing intracavitary LAK cells (individual cell doses up to 10$^9$ and cumulative cell numbers as high as 2.75×10$^{10}$), ex vivo expanded TILs (up to 10$^9$ cells/dose) and allo-reactive lymphocyte (starting cell dose 10$^8$ with cumulative cell doses up to 51.5×10$^8$). Low-dose repetitive dosing is favored to avoid potentially dangerous inflammatory responses that might occur with single large cell number instillations. Each infusion preferably consisted of a single T cell clone, and the same clone preferably was administered throughout a patient's treatment course.

Those patients demonstrating tumor regression with residual disease on MRI may have additional courses of therapy beginning no earlier than Week 7, consisting of repetition of Cycles 3 and 4 followed by one week of rest/restaging provided these treatments are well tolerated until such time that disease progression is documented, or a complete response (CR) is achieved based on radiographic evaluation. Maximum toxicities generally accepted are less than grade 3, however this is at the discretion of the treating physician.

Treatment with ganciclovir leads to the ablation of CAR+ HyTK+ CD8+ CTL clones. Therefore, any side effects associated with therapy (headache, fever, chills, nausea, etc.) which may occur can be managed using established treatments appropriate for the condition. For example, the patient may receive ganciclovir if any new grade 3 toxicity that progresses to grade 4, or any grade 4 treatment-related toxicity is observed that, in the opinion of the treating physician, puts the patient in significant medical danger. Parentally administered ganciclovir is dosed at 10 mg/kg/day divided every 12 hours. Patients should be hospitalized for the first 72 hours of ganciclovir therapy for monitoring purposes. If symptoms do not respond to ganciclovir within 48 hours, additional immunosuppressive agents, including but not limited to corticosteroids and cyclosporin, may be added at the discretion of the treating physician. If toxicities are severe, decadron and/or other immunosuppressive drugs along with ganciclovir also may be used at the discretion of the treating physician.

Preliminary safety studies using the protocol outlined above, where IL13-CAR-expressing CTL clones were administered to human patients with intracranial recurrent glioma, indicated that of the adverse events that had possible correlation with the intracavitary administration of T cells, the only Grade 3 events have been headaches that occurred with administration of 10$^8$ cells in each of the two patients treated to date. At no time were Grade 4 or 5 adverse events found to be associated with administration of the genetically altered T cells. Thus, the overall safety profile of this adoptive transfer therapy here was acceptable.

Examples 8-12

Exemplary CAR Molecules

FIGS. 14-18 provide the sequences of additional CARs according to the invention. These serve as non-limiting examples of embodiments of the invention.

FIG. 14 provides the sequence of an IL13-IgG$_4$-cd28tm-CD28gg-Zeta (CO) CAR (SEQ ID NO:36). This sequence encodes (1) the IL13 molecule with the E13Y mutation (which is the ligand for the tumor surface receptor IL13Rα2 on the tumor surface (IL13)), (2) the Fc portion of the immunoglobulin isotype G$_4$ extracellular domain (IgG$_4$), (3) the transmembrane portion of the costimulatory molecule CD28 (cd28tm), (4) the signaling domain of CD28 with two leucines changed to glycines for the purpose of increased expression (CD28gg), and (5) the signaling domain of the CD3ζ chain of the T cell receptor (Zeta). All of the segments were codon optimized (CO) for increased mammalian expression. The underlined portion of the sequence is the coding sequence for CD28gg.

FIG. 15 provides the sequence of an IL13-IgG$_4$-cd4tm-CD28-4-1BB-Zeta CAR (also referred to herein as IL13-CD28-41BBζ; SEQ ID NO:37). This sequence encodes an amino acid sequence (SEQ ID NO: 54) comprising (1) the IL13 molecule with the E13Y mutation (which is the ligand for the tumor surface receptor IL13Rα2 on the tumor surface (IL13)), (2) the Fc portion of the immunoglobulin isotype G$_4$ extracellular domain (IgG$_4$), (3) the transmembrane portion of CD4 (cd4tm); the signaling domain of the costimulatory molecule CD28 (CD28)(4) the signaling domain of the costimulatory molecule 4-1BB (4-1BB), and (5) the signaling domain of the CD3ζ chain of the T cell receptor (Zeta). The underlined portion of the sequence encodes CD28 and the Bold portion of the sequence encodes 4-1BB.

FIG. 16 provides the sequence of an IL13-IgG$_4$-cd28tm-CD28-Ox40-Zeta CAR (SEQ ID NO:38). This sequence encodes (1) the IL13 molecule with the E13Y mutation (which is the ligand for the tumor surface receptor IL13Rα2 on the tumor surface (IL13)), (2) the Fc portion of the immunoglobulin isotype G$_4$ extracellular domain (IgG$_4$), (3) the transmembrane portion of the costimulatory molecule CD28 (cd28tm), (4) the signaling domain of CD28 (CD28), (5) the signaling domain of the costimulatory molecule OX-40 (Ox40), and (6) the signaling domain of the CD3z chain of the T cell receptor (Zeta). The sequence encoding cd28tm is underlined (amino acids 364-390); the sequence encoding CD28 is in italics (amino acids 391-431); the sequence encoding Ox40 is in bold (amino acids 432-467); and the sequence encoding Zeta is both underlined and in italics (amino acids 468-580).

FIG. 17 provides the sequence of an IL13-IgG$_4$-cd28tm-CD28gg-4-1BB-Zeta CAR (SEQ ID NO:39). This sequence encodes (1) the IL13 molecule with the E13Y mutation (which is the ligand for the tumor surface receptor IL13Rα2 on the tumor surface (IL13)), (2) the Fc portion of the immunoglobulin isotype G$_4$ extracellular domain (IgG$_4$), (3) the transmembrane portion of the costimulatory molecule CD28 (cd28tm), (4) the signaling domain of CD28 with two leucines changed to glycines for the purpose of increased expression (CD28gg), (5) the signaling domain of the costimulatory molecule 4-1BB (4-1BB), and (6) the signaling domain of the CD3ζ chain of the T cell receptor (Zeta). The underlined portion of the sequence encodes CD28gg and the bold portion of the sequence encodes 4-1BB.

FIG. 18 provides the sequence of an IL13-IgG$_4$ cd28tm-CD28gg^199-4-1BB-Zeta CAR (SEQ ID NO:40). This sequence encodes (1) the IL13 molecule with the E13Y mutation (which is the ligand for the tumor surface receptor IL13Rα2 on the tumor surface (IL13)), (2) the Fc portion of the immunoglobulin isotype G$_4$ extracellular domain (IgG$_4$), (3) the transmembrane portion of the costimulatory molecule CD28 (cd28tm), (4) the signaling domain of CD28 with two leucines changed to glycines for the purpose of increased expression, and its kinase domain deleted for the purpose of removing its signaling activity (i.e., as a negative control for SEQ ID NO:39) (CD28gg^199), (5) the signaling domain of the costimulatory molecule 4-1BB (4-1BB), and (6) the signaling domain of the CD3ζ chain of the T cell receptor (Zeta). The underlined portion of the sequence encodes CD28gg^199 and the bold portion of the sequence encodes 4-1BB.

The invention claimed is:

1. A chimeric antigen receptor (CAR) comprising the amino acid sequence of SEQ ID NO: 54.
2. The CAR of claim 1, wherein the CAR is encoded by the DNA of SEQ ID NO: 37.
3. An isolated T lymphocyte that expresses the CAR of claim 1.
4. A method of cancer immunotherapy which comprises administering to a patient in need thereof a T lymphocyte that expresses the CAR of claim 1.
5. A method of cancer immunotherapy which comprises administering to a patient in need thereof a T lymphocyte of claim 3.
6. A method of claim 5 wherein said cancer is selected from the group consisting of glioblastoma, medulloblastoma, breast cancer, head and neck cancer, kidney cancer, ovarian cancer, Kaposi's sarcoma, acute myelogenous leukemia, and B-lineage malignancies.
7. A method of enhancing activity of a chimeric antigen receptor against a tumor, which comprises adding CD28 and 4-1BB signaling domains to said receptor to produce the CAR of claim 1.

* * * * *

```
                        SEQUENCE LISTING

<160> NUMBER OF SEQ ID NOS: 54

<210> SEQ ID NO 1
<211> LENGTH: 132
<212> TYPE: PRT
<213> ORGANISM: Homo sapiens

<400> SEQUENCE: 1

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Tyr Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130

<210> SEQ ID NO 2
<211> LENGTH: 416
<212> TYPE: DNA
<213> ORGANISM: Homo sapiens

<400> SEQUENCE: 2
tatgaattca tggcgctttt gttgaccacg gtcattgctc tcacttgcct tggcggcttt      60
gcctccccag gccctgtgcc tccctctaca gccctcaggt acctcattga ggagctggtc     120
aacatcaccc agaaccagaa ggctccgctc tgcaatggca gcatggtatg gagcatcaac     180
ctgacagctg gcatgtactg tgcagccctg gaatccctga tcaacgtgtc aggctgcagt     240
```

```
gccatcgaga agacccagag gatgctgagc ggattctgcc cgcacaaggt ctcagctggg    300
cagttttcca gcttgcatgt ccgagacacc aaaatcgagg tggcccagtt tgtaaaggac    360
ctgctcttac atttaaagaa acttttccgc gagggacggt tcaactgagg atccga       416
```

<210> SEQ ID NO 3
<211> LENGTH: 416
<212> TYPE: DNA
<213> ORGANISM: Homo sapiens

<400> SEQUENCE: 3

```
atacttaagt accgcgaaaa caactggtgc cagtaacgag agtgaacgga accgccgaaa     60 cggagggggtc cgggacacgg agggagatgt cgggagtcca tggagtaact cctcgaccag   120
ttgtagtggg tcttggtctt ccgaggcgag acgttaccgt cgtaccatac ctcgtagttg    180
gactgtcgac cgtacatgac acgtcgggac cttagggact agttgcacag tccgacgtca   240
cggtagctct tctgggtctc ctacgactcg cctaagacgg gcgtgttcca gagtcgaccc    300 gtcaaaggt cgaacgtaca ggctctgtgg ttttagctcc accgggtcaa acatttcctg    360
gacgagaatg taaatttctt tgaaaaagcg ctccctgcca agttgactcc taggct        416
```

<210> SEQ ID NO 4
<211> LENGTH: 497
<212> TYPE: PRT
<213> ORGANISM: Homo sapiens

<400> SEQUENCE: 4

```
Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
    130                 135                 140

Cys Pro Ala Pro Glu Phe Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
```

```
           225                 230                 235                 240
Asn Lys Gly Leu Pro Ser Ser Ile Glu Lys Thr Ile Ser Lys Ala Lys
                    245                 250                 255
Gly Gln Pro Arg Glu Pro Gln Val Tyr Thr Leu Pro Pro Ser Gln Glu
                260                 265                 270
Glu Met Thr Lys Asn Gln Val Ser Leu Thr Cys Leu Val Lys Gly Phe
            275                 280                 285
Tyr Pro Ser Asp Ile Ala Val Glu Trp Glu Ser Asn Gly Gln Pro Glu
        290                 295                 300
Asn Asn Tyr Lys Thr Thr Pro Pro Val Leu Asp Ser Asp Gly Ser Phe
305                 310                 315                 320
Phe Leu Tyr Ser Arg Leu Thr Val Asp Lys Ser Arg Trp Gln Glu Gly
                325                 330                 335
Asn Val Phe Ser Cys Ser Val Met His Glu Ala Leu His Asn His Tyr
                340                 345                 350
Thr Gln Lys Ser Leu Ser Leu Ser Leu Gly Lys Met Ala Leu Ile Val
                355                 360                 365
Leu Gly Gly Val Ala Gly Leu Leu Leu Phe Ile Gly Leu Gly Ile Phe
            370                 375                 380
Phe Arg Val Lys Phe Ser Arg Ser Ala Asp Ala Pro Ala Tyr Gln Gln
385                 390                 395                 400
Gly Gln Asn Gln Leu Tyr Asn Glu Leu Asn Leu Gly Arg Arg Glu Glu
                    405                 410                 415
Tyr Asp Val Leu Asp Lys Arg Arg Gly Arg Asp Pro Glu Met Gly Gly
                420                 425                 430
Lys Pro Arg Arg Lys Asn Pro Gln Glu Gly Leu Tyr Asn Glu Leu Gln
            435                 440                 445
Lys Asp Lys Met Ala Glu Ala Tyr Ser Glu Ile Gly Met Lys Gly Glu
        450                 455                 460
Arg Arg Arg Gly Lys Gly His Asp Gly Leu Tyr Gln Gly Leu Ser Thr
465                 470                 475                 480
Ala Thr Lys Asp Thr Tyr Asp Ala Leu His Met Gln Ala Leu Pro Pro
                485                 490                 495
Arg

<210> SEQ ID NO 5
<211> LENGTH: 1522
<212> TYPE: DNA
<213> ORGANISM: Homo sapiens

<400> SEQUENCE: 5
atctctagag ccgccaccat gcttctcctg gtgacaagcc ttctgctctg tgagttacca      60
cacccagcat tcctcctgat cccaggccct gtgcctccct ctacagccct caggtacctc     120
attgaggagc tggtcaacat cacccagaac cagaaggctc cgctctgcaa tggcagcatg     180
gtatggagca tcaacctgac agctggcatg tactgtgcag ccctggaatc cctgatcaac     240
gtgtcaggct gcagtgccat cgagaagacc cagaggatgc tgagcggatt ctgcccgcac     300
aaggtctcag ctgggcagtt ttccagcttg catgtccgag acaccaaaat cgaggtggcc     360
cagtttgtaa aggacctgct cttacattta aagaaacttt ttcgcgaggg acggttcaac     420
gagtccaaat atggtccccc atgcccacca tgcccagcac ctgagttcct ggggggacca     480
tcagtcttcc tgttcccccc aaaacccaag gacactctca tgatctcccg gacccctgag     540
gtcacgtgcg tggtggtgga cgtgagccag gaagaccccg aggtccagtt caactggtac     600
```

```
gtggatggcg tggaggtgca taatgccaag acaaagccgc gggaggagca gttcaacagc    660
acgtaccgtg tggtcagcgt cctcaccgtc ctgcaccagg actggctgaa cggcaaggag    720
tacaagtgca aggtctccaa caaaggcctc ccgtcctcca tcgagaaaac catctccaaa    780 gccaagggc agccccgaga gccacaggtg tacaccctgc ccccatccca ggaggagatg     840
accaagaacc aggtcagcct gacctgcctg gtcaaaggct tctaccccag cgacatcgcc    900
gtggagtggg agagcaatgg gcagccggag aacaactaca agaccacgcc tcccgtgctg    960
gactccgacg gctccttctt cctctacagc aggctaaccg tggacaagag caggtggcag    1020
gaggggaatg tcttctcatg ctccgtgatg catgaggctc tgcacaacca ctacacacag    1080
aagagcctct ccctgtctct gggtaaaatg gccctgattg tgctgggggg cgtcgccggc    1140
ctcctgcttt tcattgggct aggcatcttc ttcagagtga agttcagcag gagcgcagac    1200
gcccccgcgt accagcaggg ccagaaccag ctctataacg agctcaatct aggacgaaga    1260
gaggagtacg atgttttgga caagagacgt ggccgggacc ctgagatggg gggaaagccg    1320
agaaggaaga accctcagga aggcctgtac aatgaactgc agaaagataa gatggcggag    1380
gcctacagtg agattgggat gaaaggcgag cgccggaggg gcaaggggca cgatggcctt    1440
taccagggtc tcagtacagc caccaaggac acctacgacg cccttcacat gcaggccctg    1500
ccccctcgct aagcggccgc at                                             1522

<210> SEQ ID NO 6
<211> LENGTH: 1522
<212> TYPE: DNA
<213> ORGANISM: Homo sapiens

<400> SEQUENCE: 6
tagagatctc ggcggtggta cgaagaggac cactgttcgg aagacgagac actcaatggt     60
gtgggtcgta aggaggacta gggtccggga cacggaggga gatgtcggga gtccatggag    120
taactcctcg accagttgta gtgggtcttg gtcttccgag gcgagacgtt accgtcgtac    180
catacctcgt agttggactg tcgaccgtac atgacacgtc gggaccttag ggactagttg    240
cacagtccga cgtcacggta gctcttctgg gtctcctacg actcgcctaa gacgggcgtg    300
ttccagagtc gacccgtcaa aaggtcgaac gtacaggctc tgtggtttta gctccaccgg    360
gtcaaacatt tcctggacga gaatgtaaat ttctttgaaa aagcgctccc tgccaagttg    420
ctcaggttta taccaggggg tacgggtggt acgggtcgtg gactcaagga ccccccctggt   480 agtcagaagg acaaggggg ttttgggttc ctgtgagagt actagagggc ctggggactc     540
cagtgcacgc accaccacct gcactcggtc cttctgggc tccaggtcaa gttgaccatg     600
cacctaccgc acctccacgt attacggttc tgtttcggcg ccctcctcgt caagttgtcg    660
tgcatggcac accagtcgca ggagtggcag gacgtggtcc tgaccgactt gccgttcctc    720
atgttcacgt tccagaggtt gtttccggag ggcaggagg agctcttttg gtagaggttt     780
cggtttcccg tcgggctct cggtgtccac atgtgggacg ggggtagggt cctcctctac     840
tggttcttgg tccagtcgga ctggacggac cagtttccga agatggggtc gctgtagcgg    900
cacctcaccc tctcgttacc cgtcggcctc ttgttgatgt tctggtgcgg agggcacgac    960
ctgaggctgc cgaggaagaa ggagatgtcg tccgattggc acctgttctc gtccaccgtc   1020
ctccccttac agaagagtac gaggcactac gtactccgag acgtgttggt gatgtgtgtc   1080
ttctcggaga gggacagaga cccatttttac cgggactaac acgacccccc gcagcggccg   1140
```

```
gaggacgaaa agtaacccga tccgtagaag aagtctcact tcaagtcgtc ctcgcgtctg    1200
cgggggcgca tggtcgtccc ggtcttggtc gagatattgc tcgagttaga tcctgcttct    1260
ctcctcatgc tacaaaacct gttctctgca ccggccctgg gactctaccc cccttcggc     1320 tcttccttct tgggagtcct tccggacatg ttacttgacg tctttctatt ctaccgcctc    1380
cggatgtcac tctaacccta ctttccgctc gcggcctccc cgttcccgt  gctaccggaa    1440 atggtcccag agtcatgtcg gtggttcctg tggatgctgc gggaagtgta cgtccgggac    1500
gggggagcga ttcgccggcg ta                                             1522

<210> SEQ ID NO 7
<211> LENGTH: 84
<212> TYPE: DNA
<213> ORGANISM: Homo sapiens

<400> SEQUENCE: 7
atctctagag ccgccaccat gcttctcctg gtgacaagcc ttctgctctg tgagttacca    60
cacccagcat tcctcctgat ccca                                           84

<210> SEQ ID NO 8
<211> LENGTH: 336
<212> TYPE: DNA
<213> ORGANISM: Homo sapiens

<400> SEQUENCE: 8
ggccctgtgc ctccctctac agccctcagg tacctcattg aggagctggt caacatcacc    60
cagaaccaga aggctccgct ctgcaatggc agcatggtat ggagcatcaa cctgacagct    120
ggcatgtact gtgcagccct ggaatccctg atcaacgtgt caggctgcag tgccatcgag    180
aagacccaga ggatgctgag cggattctgc ccgcacaagg tctcagctgg gcagtttttcc   240 agcttgcatg tccgagacac caaaatcgag gtggcccagt ttgtaaagga cctgctctta    300
catttaaaga aacttttttcg cgagggacgg ttcaac                             336

<210> SEQ ID NO 9
<211> LENGTH: 686
<212> TYPE: DNA
<213> ORGANISM: Homo sapiens

<400> SEQUENCE: 9
gagtccaaat atggtccccc atgcccacca tgcccagcac ctgagttcct ggggggacca    60
tcagtcttcc tgttcccccc aaaacccaag gacactctca tgatctcccg gaccctgag    120 gtcacgtgcg tggtggtgga cgtgagccag gaagaccccg aggtccagtt caactggtac    180
gtggatggcg tggaggtgca taatgccaag acaaagccgc gggaggagca gttcaacagc    240
acgtaccgtg tggtcagcgt cctcaccgtc ctgcaccagg actggctgaa cggcaaggag    300
tacaagtgca aggtctccaa caaaggcctc ccgtcctcca tcgagaaaac catctccaaa    360
gccaaagggc agccccgaga gccacaggtg tacaccctgc ccccatccca ggaggagatg    420
accaagaacc aggtcagcct gacctgcctg gtcaaaggct tctaccccag cgacatcgcc    480
gtggagtggg agagcaatgg gcagccggag aacaactaca agaccacgcc tcccgtgctg    540
gactccgacg gctccttctt cctctacagc aggctaaccg tggacaagag caggtggcag    600 gagggggaatg tcttctcatg ctccgtgatg catgaggctc tgcacaacca ctacacacag    660
aagagcctct ccctgtctct gggtaa                                         686
```

```
<210> SEQ ID NO 10
<211> LENGTH: 67
<212> TYPE: DNA
<213> ORGANISM: Homo sapiens

<400> SEQUENCE: 10
aatggccctg attgtgctgg ggggcgtcgc cggcctcctg cttttcattg ggctaggcat      60
cttcttc                                                               67

<210> SEQ ID NO 11
<211> LENGTH: 339
<212> TYPE: DNA
<213> ORGANISM: Homo sapiens

<400> SEQUENCE: 11
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg atgggggg aaagccgaga aggaagaacc ctcaggaagg cctgtacaat      180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgctaa                           339

<210> SEQ ID NO 12
<211> LENGTH: 1092
<212> TYPE: DNA
<213> ORGANISM: Artificial Sequence
<220> FEATURE:
<223> OTHER INFORMATION: plasmid vector

<400> SEQUENCE: 12
gagtccaaat atggtccccc atgcccacca tgcccagcac ctgagttcct ggggggacca      60
tcagtcttcc tgttcccccc aaacccaag gacactctca tgatctcccg gacccctgag      120
gtcacgtgcg tggtggtgga cgtgagccag gaagaccccg aggtccagtt caactggtac     180
gtggatggcg tggaggtgca taatgccaag acaaagccgc gggaggagca gttcaacagc     240
acgtaccgtg tggtcagcgt cctcaccgtc ctgcaccagg actggctgaa cggcaaggag     300
tacaagtgca aggtctccaa caaaggcctc ccgtcctcca tcgagaaaac catctccaaa     360
gccaaagggc agccccgaga gccacaggtg tacaccctgc ccccatccca ggaggagatg     420
accaagaacc aggtcagcct gacctgcctg gtcaaaggct tctaccccag cgacatcgcc     480
gtggagtggg agagcaatgg gcagccggag aacaactaca agaccacgcc tcccgtgctg     540
gactccgacg gctccttctt cctctacagc aggctaaccg tggacaagag caggtggcag     600
gaggggaatg tcttctcatg ctccgtgatg catgaggctc tgcacaacca ctacacacag     660
aagagcctct ccctgtctct gggtaaaatg gccctgattg tgctgggggg cgtcgccggc     720
ctcctgcttt tcattgggct aggcatcttc ttcagagtga agttcagcag gagcgcagac     780
gcccccgcgt accagcaggg ccagaaccag ctctataacg agctcaatct aggacgaaga     840
gaggagtacg atgttttgga caagagacgt ggccgggacc ctgagatggg gggaaagccg     900
agaaggaaga cccctcagga aggcctgtac aatgaactgc agaaagataa gatggcggag     960
gcctacagtg agattgggat gaaaggcgag cgccggaggg gcaaggggca cgatggcctt    1020
taccagggtc tcagtacagc caccaaggac acctacgacg cccttcacat gcaggccctg    1080 cccctcgct aa                                                        1092
```

<210> SEQ ID NO 13
<211> LENGTH: 6770
<212> TYPE: DNA
<213> ORGANISM: Artificial Sequence
<220> FEATURE:
<223> OTHER INFORMATION: plasmid vector

<400> SEQUENCE: 13

```
tcgaaggatc tgcgatcgct ccggtgcccg tcagtgggca gagcgcacat cgcccacagt      60
ccccgagaag ttgggggag gggtcggcaa ttgaaccggt gcctagagaa ggtggcgcgg      120
ggtaaactgg gaaagtgatg tcgtgtactg gctccgcctt tttcccgagg gtgggggaga     180
accgtatata agtgcagtag tcgccgtgaa cgttcttttt cgcaacgggt ttgccgccag     240
aacacagctg aagcttcgag gggctcgcat ctctccttca cgcgcccgcc gccctacctg     300
aggccgccat ccacgccggt tgagtcgcgt tctgccgcct cccgcctgtg gtgcctcctg     360
aactgcgtcc gccgtctagg taagtttaaa gctcaggtcg agaccgggcc tttgtccggc     420
gctcccttgg agcctaccta gactcagccg gctctccacg ctttgcctga ccctgcttgc     480
tcaactctac gtctttgttt cgttttctgt tctgcgccgt tacagatcca agctgtgacc     540
ggcgcctacg taagtgatat ctactagatt tatcaaaaag agtgttgact tgtgagcgct     600
cacaattgat acggattcat cgagagggac acgtcgacta ctaaccttct tctctttcct     660
acagctgaga tcaccctaga gccgccacca tgcttctcct ggtgacaagc cttctgctct     720
gtgagttacc acaccagca ttcctcctga tcccaggccc tgtgcctccc tctacagccc      780
tcaggtacct cattgaggag ctggtcaaca tcacccagaa ccagaaggct ccgctctgca     840
atggcagcat ggtatggagc atcaacctga gctggcat gtactgtgca gccctggaat       900
ccctgatcaa cgtgtcaggc tgcagtgcca tcgagaagac ccagaggatg ctgagcggat     960
tctgcccgca caaggtctca gctgggcagt tttccagctt gcatgtccga cacaccaaaa    1020
tcgaggtggc ccagtttgta aaggacctgc tcttacattt aaagaaactt tttcgcgagg    1080
gacggttcaa cgagtccaaa tatggtcccc catgcccacc atgcccagca cctgagttcc    1140
tggggggacc atcagtcttc ctgttccccc caaaacccaa ggacactctc atgatctccc    1200
ggaccctga ggtcacgtgc gtggtggtgg acgtgagcca ggaagacccc gaggtccagt    1260
tcaactggta cgtggatggc gtggaggtgc ataatgccaa gacaaagccg cgggaggagc    1320
agttcaacag cacgtaccgt gtggtcagcg tcctcaccgt cctgcaccag gactggctga    1380
acggcaagga gtacaagtgc aaggtctcca caaaggccc cgtcctcc atcgagaaaa    1440
ccatctccaa agccaaaggg cagccccgag agccacaggt gtacaccctg cccccatccc    1500
aggaggagat gaccaagaac caggtcagcc tgacctgcct ggtcaaaggc ttctacccca    1560
gcgacatcgc cgtggagtgg gagagcaatg ggcagccgga gaacaactac aagaccacgc    1620
ctcccgtgct ggactccgac ggctccttct cctctacag caggctaacc gtggacaaga    1680
gcaggtggca ggaggggaat gtcttctcat gctccgtgat gcatgaggct ctgcacaacc    1740
actacacaca gaagagcctc tccctgtccc taggtaaaat ggccctgatt gtgctggggg    1800
gcgtcgccgg cctcctgctt ttcattgggc taggcatctt cttcagagtg aagttcagca    1860
ggagcgcaga cgccccgcg taccagcagg gccagaacca gctctataac gagctcaatc    1920
taggacgaag agaggagtac gatgttttgg acaagagacg tggccgggac cctgagatgg    1980
ggggaaagcc gagaaggaag aaccctcagg aaggcctgta caatgaactg cagaaagata    2040
agatggcgga ggcctacagt gagattggga tgaaaggcga gcgccggagg ggcaaggggc    2100
```

```
acgatggcct ttaccagggt ctcagtacag ccaccaagga cacctacgac gcccttcaca    2160
tgcaggccct gcccctcgc tgagcggccg gcgaaggagg cctagatcta tcgattgtac     2220
agctagctcg acatgataag atacattgat gagtttggac aaaccacaac tagaatgcag    2280 tgaaaaaat gctttatttg tgaaattgt gatgctattg ctttatttgt gaaatttgtg      2340
atgctattgc tttatttgta accattataa gctgcaataa acaagttaac aacaacaatt    2400
gcattcattt tatgtttcag gttcaggggg aggtgtggga ggttttttaa agcaagtaaa    2460
acctctacaa atgtggtaga tccatttaaa tgttagcgaa gaacatgtga gcaaaaggcc    2520
agcaaaaggc caggaaccgt aaaaaggccg cgttgctggc gttttccat aggctccgcc     2580 cccctgacga gcatcacaaa aatcgacgct caagtcagag gtggcgaaac ccgacaggac    2640
tataaagata ccaggcgttt ccccctggaa gctccctcgt gcgctctcct gttccgaccc    2700
tgccgcttac cggatacctg tccgcctttc tcccttcggg aagcgtggcg ctttctcaat    2760
gctcacgctg taggtatctc agttcggtgt aggtcgttcg ctccaagctg gctgtgtgc    2820 acgaaccccc cgttcagccc gaccgctgcg ccttatccgg taactatcgt cttgagtcca    2880
acccggtaag acacgactta tcgccactgg cagcagccac tggtaacagg attagcagag    2940
cgaggtatgt aggcggtgct acagagttct tgaagtggtg gcctaactac ggctacacta    3000
gaagaacagt atttggtatc tgcgctctgc tgaagccagt taccttcgga aaaagagttg    3060
gtagctcttg atccggcaaa caaaccaccg ctggtagcgg tggtttttt gtttgcaagc    3120 agcagattac gcgcagaaaa aaaggatctc aagaagatcc tttgatcttt tctacggggt    3180
ctgacgctca gtggaacgaa aactcacgtt aagggatttt ggtcatggct agttaattaa    3240
gctgcaataa acaatcatta ttttcattgg atctgtgtgt tggttttttg tgtgggcttg    3300
ggggaggggg aggccagaat gactccaaga gctacaggaa ggcaggtcag agaccccact    3360
ggacaaacag tggctggact ctgcaccata acacacaatc aacaggggag tgagctggat    3420
cgagctagag tccgttacat aacttacggt aaatggcccg cctggctgac cgcccaacga    3480
cccccgccca ttgacgtcaa taatgacgta tgttcccata gtaacgccaa tagggacttt    3540
ccattgacgt caatgggtgg agtatttacg gtaaactgcc cacttggcag tacatcaagt    3600
gtatcatatg ccaagtacgc cccctattga cgtcaatgac ggtaaatggc ccgcctggca    3660
ttatgcccag tacatgacct tatgggactt tcctacttgg cagtacatct acgtattagt    3720
catcgctatt accatggtga tgcggttttg gcagtacatc aatgggcgtg atagcggtt    3780 tgactcacgg ggatttccaa gtctccaccc cattgacgtc aatgggagtt gttttggca    3840 ccaaaatcaa cgggactttc caaaatgtcg taacaactcc gccccattga cgcaaatggg    3900
cggtaggcgt gtacggtggg aggtctatat aagcagagct cgtttagtga accgtcagat    3960
cgcctggaga cgccatccac gctgttttga cctccataga agacaccggg accgatccag    4020
cctccgcggc cgggaacggt gcattggaac gcggattccc cgtgccaaga gtgacgtaag    4080
taccgcctat agagtctata ggcccaccta gttgtgaccg cgcctagtg ttgacaatta    4140 atcatcggca tagtataata cgactcacta taggagggcc accatgtcga ctactaacct    4200
tcttctcttt cctacagctg agatcaccgg taggagggcc atcatgaaaa agcctgaact    4260
caccgcgacg tctgtcgcga agtttctgat cgaaaagttc gacagcgtct ccgacctgat    4320
gcagctctcg gagggcgaag aatctcgtgc tttcagcttc gatgtaggag ggcgtggata    4380
tgtcctgcgg gtaaatagct gcgccgatgg tttctacaaa gatcgttatg tttatcggca    4440
```

```
ctttgcatcg gccgcgctcc cgattccgga agtgcttgac attggggaat tcagcgagag      4500
cctgacctat tgcatctccc gccgtgcaca gggtgtcacg ttgcaagacc tgcctgaaac      4560
cgaactgccc gctgttctgc aacccgtcgc ggagctcatg gatgcgatcg ctgcggccga      4620
tcttagccag acgagcgggt tcggcccatt cggaccgcaa ggaatcggtc aatacactac      4680
atggcgtgat ttcatatgcg cgattgctga tccccatgtg tatcactggc aaactgtgat      4740
ggacgacacc gtcagtgcgt ccgtcgcgca ggctctcgat gagctgatgc tttgggccga      4800
ggactgcccc gaagtccggc acctcgtgca cgcggatttc ggctccaaca atgtcctgac      4860
ggacaatggc cgcataacag cggtcattga ctggagcgag gcgatgttcg gggattccca      4920
atacgaggtc gccaacatct tcttctggag gccgtggttg gcttgtatgg agcagcagac      4980
gcgctacttc gagcggaggc atccggagct tgcaggatcg ccgcggctcc gggcgtatat      5040
gctccgcatt ggtcttgacc aactctatca gagcttggtt gacggcaatt tcgatgatgc      5100
agcttgggcg cagggtcgat gcgacgcaat cgtccgatcc ggagccggga ctgtcgggcg      5160
tacacaaatc gcccgcagaa gcgcggccgt ctggaccgat ggctgtgtag aagtcgcgtc      5220
tgcgttcgac caggctgcgc gttctcgcgg ccatagcaac cgacgtacgg cgttgcgccc      5280
tcgccggcag caagaagcca cggaagtccg cccggagcag aaaatgccca cgctactgcg      5340
ggtttatata gacggtcccc acgggatggg gaaaaccacc accacgcaac tgctggtggc      5400
cctgggttcg cgcgacgata tcgtctacgt acccgagccg atgacttact ggcgggtgct      5460
gggggcttcc gagacaatcg cgaacatcta caccacacaa caccgcctcg accagggtga      5520
gatatcggcc ggggacgcgg cggtggtaat gacaagcgcc cagataacaa tgggcatgcc      5580
ttatgccgtg accgacgccg ttctggctcc tcatatcggg ggggaggctg ggagctcaca      5640
tgccccgccc ccgccctca ccctcatctt cgaccgccat cccatcgccg ccctcctgtg      5700
ctacccggcc gcgcggtacc ttatgggcag catgaccccc caggccgtgc tggcgttcgt      5760
ggccctcatc ccgccgacct tgcccggcac caacatcgtg cttggggccc ttccggagga      5820
cagacacatc gaccgcctgg ccaaacgcca gcgccccggc gagcggctgg acctggctat      5880
gctggctgcg attcgccgcg tttacgggct acttgccaat acggtgcggt atctgcagtg      5940
cggcgggtcg tggcgggagg actggggaca gctttcgggg acggccgtgc cgccccaggg      6000
tgccgagccc cagagcaacg cgggcccacg accccatatc ggggacacgt tatttaccct      6060
gtttcgggcc cccgagttgc tggccccaa cggcgacctg tataacgtgt ttgcctgggc      6120
cttgacgtc ttggccaaac gcctccgttc catgcacgtc tttatcctgg attacgacca      6180
atcgcccgcc ggctgccggg acgccctgct gcaacttacc tccgggatgg tccagaccca      6240
cgtcaccacc cccggctcca taccgacgat atgcgacctg gcgcgcacgt ttgcccggga      6300
gatgggggag gctaactgag tcgagaattc gctagagggc cctattctat agtgtcacct      6360
aaatgctaga gctcgctgat cagcctcgac tgtgccttct agttgccagc catctgttgt      6420
ttgcccctcc cccgtgcctt ccttgaccct ggaaggtgcc actcccactg tcctttccta      6480
ataaaatgag gaaattgcat cgcattgtct gagtaggtgt cattctattc tggggggtgg      6540
ggtggggcag gacagcaagg gggaggattg ggaagacaat agcaggcatg cgcagggccc      6600
aattgctcga gcggccgcaa taaaatatct ttattttcat tacatctgtg tgttggtttt      6660
ttgtgtgaat cgtaactaac atacgctctc catcaaaaca aacgaaaca aaacaaacta      6720
gcaaaatagg ctgtccccag tgcaagtgca ggtgccagaa catttctcta              6770
```

```
<210> SEQ ID NO 14
<211> LENGTH: 6770
<212> TYPE: DNA
<213> ORGANISM: Homo sapiens

<400> SEQUENCE: 14
agcttcctag acgctagcga ggccacgggc agtcacccgt ctcgcgtgta gcgggtgtca    60
ggggctcttc aaccccctc cccagccgtt aacttggcca cggatctctt ccaccgcgcc    120
ccatttgacc ctttcactac agcacatgac cgaggcggaa aaagggctcc cacccctct    180 tggcatatat tcacgtcatc agcggcactt gcaagaaaaa gcgttgccca acggcggtc    240 ttgtgtcgac ttcgaagctc cccgagcgta gagaggaagt gcgcgggcgg cgggatggac    300
tccggcggta ggtgcggcca actcagcgca agacggcgga gggcggacac cacggaggac    360
ttgacgcagg cggcagatcc attcaaattt cgagtccagc tctggcccgg aaacaggccg    420
cgagggaacc tcggatggat ctgagtcggc cgagaggtgc gaaacggact gggacgaacg    480
agttgagatg cagaaacaaa gcaaaagaca agacgcggca atgtctaggt tcgacactgg    540
ccgcggatgc attcactata gatgatctaa atagtttttc tcacaactga acactcgcga    600
gtgttaacta tgcctaagta gctctccctg tgcagctgat gattggaaga agagaaagga    660
tgtcgactct agtgggatct cggcggtggt acgaagagga ccactgttcg gaagacgaga    720
cactcaatgg tgtgggtcgt aaggaggact agggtccggg acacggaggg agatgtcggg    780
agtccatgga gtaactcctc gaccagttgt agtgggtctt ggtcttccga ggcgagacgt    840
taccgtcgta ccatacctcg tagttggact gtcgaccgta catgacacgt cgggaccttc   900
gggactagtt gcacagtccg acgtcacggt agctcttctg ggtctcctac gactcgccta    960
agacgggcgt gttccagagt cgacccgtca aaaggtcgaa cgtacaggct ctgtggtttt   1020
agctccaccg ggtcaaacat ttcctggacg agaatgtaaa tttctttgaa aaagcgctcc   1080
ctgccaagtt gctcaggttt ataccagggg gtacgggtgg tacgggtcgt ggactcaagg   1140 accccctgg tagtcagaag gacaaggggg gttttgggtt cctgtgagag tactagaggg   1200 cctgggact ccagtgcacg caccaccacc tgcactcggt ccttctgggg ctccaggtca   1260
agttgaccat gcacctaccg cacctccacg tattacggtt ctgtttcggc gccctcctcg   1320
tcaagttgtc gtgcatggca caccagtcgc aggagtggca ggacgtggtc ctgaccgact   1380
tgccgttcct catgttcacg ttccagaggt tgtttccgga gggcaggagg tagctctttt   1440
ggtagaggtt tcggtttccc gtcggggctc tcggtgtcca catgtgggac ggggtaggg   1500 tcctcctcta ctggttcttg gtccagtcgg actggacgga ccagtttccg aagatggggt   1560
cgctgtagcg gcacctcacc ctctcgttac ccgtcggcct cttgttgatg ttctggtgcg   1620
gagggcacga cctgaggctg ccgaggaaga aggagatgtc gtccgattgg cacctgttct   1680
cgtccaccgt cctcccctta cagaagagta cgaggcacta cgtactccga gacgtgttgg   1740
tgatgtgtgt cttctcggag agggacaggg atccattta ccgggactaa cacgaccccc   1800
cgcagcggcc ggaggacgaa aagtaacccg atccgtagaa gaagtctcac ttcaagtcgt   1860
cctcgcgtct gcggggcgc atggtcgtcc cggtcttggt cgagatattg ctcgagttag   1920
atcctgcttc tctcctcatg ctacaaaacc tgttctctgc accggccctg ggactctacc   1980
cccctttcgg ctcttccttc ttgggagtcc ttccggacat gttacttgac gtctttctat   2040
tctaccgcct ccggatgtca ctctaaccct actttccgct cgcggcctcc ccgttccccg   2100
tgctaccgga aatggtccca gagtcatgtc ggtggttcct gtggatgctg cgggaagtgt   2160
```

```
acgtccggga cggggagcg actcgccggc cgcttcctcc ggatctagat agctaacatg   2220
tcgatcgagc tgtactattc tatgtaacta ctcaaacctg tttggtgttg atcttacgtc   2280
acttttttta cgaaataaac actttaaaca ctacgataac gaaataaaca ctttaaacac   2340
tacgataacg aaataaacat tggtaatatt cgacgttatt tgttcaattg ttgttgttaa   2400
cgtaagtaaa atacaaagtc caagtccccc tccacaccct ccaaaaaatt tcgttcattt   2460
tggagatgtt tacaccatct aggtaaattt acaatcgctt cttgtacact cgttttccgg   2520
tcgttttccg gtccttggca ttttttcggc gcaacgaccg caaaaaggta tccgaggcgg   2580
ggggactgct cgtagtgttt ttagctgcga gttcagtctc caccgctttg gctgtcctg    2640 atatttctat ggtccgcaaa gggggacctt cgagggagca cgcgagagga caaggctggg   2700
acggcgaatg gcctatggac aggcggaaag agggaagccc ttcgcaccgc gaaagagtta   2760
cgagtgcgac atccatagag tcaagccaca tccagcaagc gaggttcgac ccgacacacg   2820
tgcttggggg gcaagtcggg ctggcgacgc ggaataggcc attgatagca gaactcaggt   2880
tgggccattc tgtgctgaat agcggtgacc gtcgtcggtg accattgtcc taatcgtctc   2940
gctccataca tccgccacga tgtctcaaga acttcaccac cggattgatg ccgatgtgat   3000
cttcttgtca taaccatag acgcgagacg acttcggtca atggaagcct ttttctcaac    3060
catcgagaac taggccgttt gtttggtggc gaccatcgcc accaaaaaaa caaacgttcg   3120
tcgtctaatg cgcgtctttt tttcctagag ttcttctagg aaactagaaa agatgcccca   3180
gactgcgagt caccttgctt ttgagtgcaa ttccctaaaa ccagtaccga tcaattaatt   3240
cgacgttatt tgttagtaat aaaagtaacc tagacacaca accaaaaaac acacccgaac   3300
cccctccccc tccggtctta ctgaggttct cgatgtcctt ccgtccagtc tctggggtga   3360
cctgtttgtc accgacctga gacgtggtat tgtgtgttag ttgtcccctc actcgaccta   3420
gctcgatctc aggcaatgta ttgaatgcca tttaccgggc ggaccgactg cgggttgct    3480 gggggcgggt aactgcagtt attactgcat acaagggtat cattgcggtt atccctgaaa   3540
ggtaactgca gttacccacc tcataaatgc catttgacgg gtgaaccgtc atgtagttca   3600
catagtatac ggttcatgcg ggggataact gcagttactg ccatttaccg gcggaccgt    3660 aatacgggtc atgtactgga ataccctgaa aggatgaacc gtcatgtaga tgcataatca   3720
gtagcgataa tggtaccact acgccaaaac cgtcatgtag ttaccgcac ctatcgccaa    3780 actgagtgcc cctaaaggtt cagaggtggg gtaactgcag ttaccctcaa acaaaaccgt   3840
ggttttagtt gccctgaaag gttttacagc attgttgagg cggggtaact gcgtttaccc   3900
gccatccgca catgccaccc tccagatata ttcgtctcga gcaaatcact ggcagtcta    3960 gcggacctct gcggtaggtg cgacaaaact ggaggtatct tctgtggccc tggctaggtc   4020
ggaggcgccg gcccttgcca cgtaaccttg cgcctaaggg gcacggttct cactgcattc   4080
atggcggata tctcagatat ccgggtggat caacactggc cgcggatcac aactgttaat   4140
tagtagccgt atcatattat gctgagtgat atcctcccgg tggtacagct gatgattgga   4200
agaagagaaa ggatgtcgac tctagtggcc atcctcccgg tagtactttt tcggacttga   4260
gtggcgctgc agacagcgct tcaaagacta gcttttcaag ctgtcgcaga ggctggacta   4320
cgtcgagagc ctcccgcttc ttagagcacg aaagtcgaag ctacatcctc ccgcacctat   4380
acaggacgcc catttatcga cgcggctacc aaagatgttt ctagcaatac aaatagccgt   4440
gaaacgtagc cggcgcgagg gctaaggcct tcacgaactg taaccccta agtcgctctc    4500 ggactggata acgtagaggg cggcacgtgt cccacagtgc aacgttctgg acggactttg   4560
```

-continued

```
gcttgacggg cgacaagacg ttgggcagcg cctcgagtac ctacgctagc gacgccggct    4620
agaatcggtc tgctcgccca agccgggtaa gcctggcgtt ccttagccag ttatgtgatg    4680
taccgcacta aagtatacgc gctaacgact aggggtacac atagtgaccg tttgacacta    4740
cctgctgtgg cagtcacgca ggcagcgcgt ccgagagcta ctcgactacg aaacccggct    4800
cctgacgggg cttcaggccg tggagcacgt gcgcctaaag ccgaggttgt tacaggactg    4860
cctgttaccg gcgtattgtc gccagtaact gacctcgctc cgctacaagc ccctaagggt    4920
tatgctccag cggttgtaga agaagacctc cggcaccaac cgaacatacc tcgtcgtctg    4980
cgcgatgaag ctcgcctccg taggcctcga acgtcctagc ggcgccgagg cccgcatata    5040
cgaggcgtaa ccagaactgg ttgagatagt ctcgaaccaa ctgccgttaa agctactacg    5100
tcgaacccgc gtcccagcta cgctgcgtta gcaggctagg cctcggccct dacagcccgc    5160
atgtgtttag cgggcgtctt cgcgccggca gacctggcta ccgacacatc ttcagcgcag    5220
acgcaagctg gtccgacgcg caagagcgcc ggtatcgttg gctgcatgcc gcaacgcggg    5280
agcggccgtc gttcttcggt gccttcaggc gggcctcgtc ttttacgggt gcgatgacgc    5340
ccaaatatat ctgccagggg tgccctaccc cttttggtgg tggtgcgttg acgaccaccg    5400
ggacccaagc gcgctgctat agcagatgca tgggctcggc tactgaatga ccgcccacga    5460
cccccgaagg ctctgttagc gcttgtagat gtggtgtgtt gtggcggagc tggtcccact    5520
ctatagccgg cccctgcgcc gccaccatta ctgttcgcgg gtctattgtt acccgtacgg    5580 aatacgcac tggctgcggc aagaccgagg agtatagccc ccctccgac cctcgagtgt    5640 acggggcggg ggccgggagt gggagtagaa gctggcggta gggtagcggc gggaggacac    5700
gatgggccgg cgcgccatgg aatacccgtc gtactggggg gtccggcacg accgcaagca    5760
ccgggagtag ggcggctgga acgggccgtg gttgtagcac gaaccccggg aaggcctcct    5820
gtctgtgtag ctggcggacc ggtttgcggt cgcggggccg ctcgccgacc tggaccgata    5880
cgaccgacgc taagcggcgc aaatgcccga tgaacggtta tgccacgcca tagacgtcac    5940
gccgcccagc accgccctcc tgaccccctgt cgaaagcccc tgccggcacg gcggggtccc    6000
acggctcggg gtctcgttgc gcccgggtgc tgggtatag cccctgtgca ataaatggga    6060
caaagcccgg gggctcaacg accggggggtt gccgctggac atattgcaca aacggacccg    6120
gaacctgcag aacggtttg cggaggcaag gtacgtgcag aaataggacc taatgctggt    6180
tagcgggcgg ccgacggccc tgcgggacga cgttgaatgg aggccctacc aggtctgggt    6240
gcagtggtgg gggccgaggt atggctgcta tacgctggac cgcgcgtgca aacgggccct    6300 ctacccctc cgattgactc agctcttaag cgatctcccg ggataagata tcacagtgga    6360
tttacgatct cgagcgacta gtcggagctg acacggaaga tcaacggtcg gtagacaaca    6420
aacggggagg gggcacggaa ggaactggga ccttccacgg tgagggtgac aggaaaggat    6480 tatttactc ctttaacgta gcgtaacaga ctcatccaca gtaagataag accccccacc    6540
ccaccccgtc ctgtcgttcc ccctcctaac ccttctgtta tcgtccgtac gcgtcccggg    6600
ttaacgagct cgccggcgtt attttataga aataaaagta atgtagacac acaaccaaaa    6660
aacacactta gcattgattg tatgcgagag gtagttttgt tttgctttgt tttgtttgat    6720
cgttttatcc gacaggggtc acgttcacgt ccacggtctt gtaaagagat              6770
```

<210> SEQ ID NO 15
<211> LENGTH: 497
<212> TYPE: PRT

<213> ORGANISM: Homo sapiens

<400> SEQUENCE: 15

```
Met Leu Leu Leu Val Thr Ser Leu Leu Leu Cys Glu Leu Pro His Pro
1               5                   10                  15

Ala Phe Leu Leu Ile Pro Gly Pro Val Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
        50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu His Leu Lys Lys Leu Phe
        115                 120                 125

Arg Glu Gly Arg Phe Asn Glu Ser Lys Tyr Gly Pro Pro Cys Pro Pro
130                 135                 140

Cys Pro Ala Pro Glu Phe Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Asn Ser Thr Tyr Arg Val Val Ser Val Leu Thr Val
210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
            290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335

Asn Val Phe Ser Cys Ser Val Met His Glu Ala Leu His Asn His Tyr
            340                 345                 350

Thr Gln Lys Ser Leu Ser Leu Ser Leu Gly Lys Met Ala Leu Ile Val
        355                 360                 365

Leu Gly Gly Val Ala Gly Leu Leu Phe Ile Gly Leu Gly Ile Phe
            370                 375                 380

Phe Arg Val Lys Phe Ser Arg Ser Ala Asp Ala Pro Ala Tyr Gln Gln
385                 390                 395                 400
```

-continued

Gly Gln Asn Gln Leu Tyr Asn Glu Leu Asn Leu Gly Arg Arg Glu Glu
                        405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 16
<211> LENGTH: 691
<212> TYPE: PRT
<213> ORGANISM: Homo sapiens

<400> SEQUENCE: 16

Met Lys Lys Pro Glu Leu Thr Ala Thr Ser Val Ala Lys Phe Leu Ile
1               5                   10                  15

Glu Lys Phe Asp Ser Val Ser Asp Leu Met Gln Leu Ser Glu Gly Glu
                20                  25                  30

Glu Ser Arg Ala Phe Ser Phe Asp Val Gly Gly Arg Gly Tyr Val Leu
            35                  40                  45

Arg Val Asn Ser Cys Ala Asp Gly Phe Tyr Lys Asp Arg Tyr Val Tyr
        50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
                100                 105                 110

Gln Pro Val Ala Glu Leu Met Asp Ala Ile Ala Ala Ala Asp Leu Ser
            115                 120                 125

Gln Thr Ser Gly Phe Gly Pro Phe Gly Pro Gln Gly Ile Gly Gln Tyr
        130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
        210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg His Pro Glu Leu
                245                 250                 255

Ala Gly Ser Pro Arg Leu Arg Ala Tyr Met Leu Arg Ile Gly Leu Asp
            260                 265                 270

```
Gln Leu Tyr Gln Ser Leu Val Asp Gly Asn Phe Asp Ala Ala Trp
            275                 280                 285

Ala Gln Gly Arg Cys Asp Ala Ile Val Arg Ser Gly Ala Gly Thr Val
290                 295                 300

Gly Arg Thr Gln Ile Ala Arg Arg Ser Ala Ala Val Trp Thr Asp Gly
305                 310                 315                 320

Cys Val Glu Val Ala Ser Ala Phe Asp Gln Ala Ala Arg Ser Arg Gly
                325                 330                 335

His Ser Asn Arg Arg Thr Ala Leu Arg Pro Arg Gln Gln Glu Ala
            340                 345                 350

Thr Glu Val Arg Pro Glu Gln Lys Met Pro Thr Leu Leu Arg Val Tyr
                355                 360                 365

Ile Asp Gly Pro His Gly Met Gly Lys Thr Thr Thr Gln Leu Leu
370                 375                 380

Val Ala Leu Gly Ser Arg Asp Asp Ile Val Tyr Val Pro Glu Pro Met
385                 390                 395                 400

Thr Tyr Trp Arg Val Leu Gly Ala Ser Glu Thr Ile Ala Asn Ile Tyr
                405                 410                 415

Thr Thr Gln His Arg Leu Asp Gln Gly Glu Ile Ser Ala Gly Asp Ala
                420                 425                 430

Ala Val Val Met Thr Ser Ala Gln Ile Thr Met Gly Met Pro Tyr Ala
            435                 440                 445

Val Thr Asp Ala Val Leu Ala Pro His Ile Gly Gly Glu Ala Gly Ser
    450                 455                 460

Ser His Ala Pro Pro Pro Ala Leu Thr Leu Ile Phe Asp Arg His Pro
465                 470                 475                 480

Ile Ala Ala Leu Leu Cys Tyr Pro Ala Ala Arg Tyr Leu Met Gly Ser
                485                 490                 495

Met Thr Pro Gln Ala Val Leu Ala Phe Val Ala Leu Ile Pro Pro Thr
            500                 505                 510

Leu Pro Gly Thr Asn Ile Val Leu Gly Ala Leu Pro Glu Asp Arg His
    515                 520                 525

Ile Asp Arg Leu Ala Lys Arg Gln Arg Pro Gly Glu Arg Leu Asp Leu
530                 535                 540

Ala Met Leu Ala Ala Ile Arg Arg Val Tyr Gly Leu Leu Ala Asn Thr
545                 550                 555                 560

Val Arg Tyr Leu Gln Cys Gly Gly Ser Trp Arg Glu Asp Trp Gly Gln
                565                 570                 575

Leu Ser Gly Thr Ala Val Pro Pro Gln Gly Ala Glu Pro Gln Ser Asn
            580                 585                 590

Ala Gly Pro Arg Pro His Ile Gly Asp Thr Leu Phe Thr Leu Phe Arg
            595                 600                 605

Ala Pro Glu Leu Leu Ala Pro Asn Gly Asp Leu Tyr Asn Val Phe Ala
610                 615                 620

Trp Ala Leu Asp Val Leu Ala Lys Arg Leu Arg Ser Met His Val Phe
625                 630                 635                 640

Ile Leu Asp Tyr Asp Gln Ser Pro Ala Gly Cys Arg Asp Ala Leu Leu
                645                 650                 655

Gln Leu Thr Ser Gly Met Val Gln Thr His Val Thr Thr Pro Gly Ser
            660                 665                 670

Ile Pro Thr Ile Cys Asp Leu Ala Arg Thr Phe Ala Arg Glu Met Gly
            675                 680                 685

Glu Ala Asn
```

<210> SEQ ID NO 17
<211> LENGTH: 102
<212> TYPE: DNA
<213> ORGANISM: Homo sapiens

<400> SEQUENCE: 17

```
tatgaattca tggcgctttt gttgaccacg gtcattgctc tcacttgcct tggcggcttt    60
gcctccccag gccctgtgcc tccctctaca gccctcaggt ac                      102
```

<210> SEQ ID NO 18
<211> LENGTH: 101
<212> TYPE: DNA
<213> ORGANISM: Homo sapiens

<400> SEQUENCE: 18

```
gttgatgctc cataccatgc tgccattgca gagcggagcc ttctggttct gggtgatgtt    60
gaccagctcc tcaatgaggt acctgagggc tgtagaggga g                       101
```

<210> SEQ ID NO 19
<211> LENGTH: 100
<212> TYPE: DNA
<213> ORGANISM: Homo sapiens

<400> SEQUENCE: 19

```
ctctgggtct tctcgatggc actgcagcct gacacgttga tcagggattc cagggctgca    60
cagtacatgc cagctgtcag gttgatgctc cataccatgc                         100
```

<210> SEQ ID NO 20
<211> LENGTH: 100
<212> TYPE: DNA
<213> ORGANISM: Homo sapiens

<400> SEQUENCE: 20

```
cctcgatttt ggtgtctcgg acatgcaagc tggaaaactg cccagctgag accttgtgcg    60
ggcagaatcc gctcagcatc ctctgggtct tctcgatggc                         100
```

<210> SEQ ID NO 21
<211> LENGTH: 96
<212> TYPE: DNA
<213> ORGANISM: Homo sapiens

<400> SEQUENCE: 21

```
tcggatcctc agttgaaccg tccctcgcga aaaagtttct ttaaatgtaa gagcaggtcc    60
tttacaaact gggccacctc gattttggtg tctcgg                             96
```

<210> SEQ ID NO 22
<211> LENGTH: 39
<212> TYPE: DNA
<213> ORGANISM: Homo sapiens

<400> SEQUENCE: 22

```
caacctgaca gctggcatgt actgtgcagc cctggaatc                           39
```

<210> SEQ ID NO 23
<211> LENGTH: 39
<212> TYPE: DNA
<213> ORGANISM: Homo sapiens

<400> SEQUENCE: 23

```
gttggactgt cgaccgtaca tgacacgtcg ggaccttag                               39
```

<210> SEQ ID NO 24
<211> LENGTH: 43
<212> TYPE: DNA
<213> ORGANISM: Homo sapiens

<400> SEQUENCE: 24

```
atctctagag ccgccaccat gcttctcctg gtgacaagcc ttc                         43
```

<210> SEQ ID NO 25
<211> LENGTH: 34
<212> TYPE: DNA
<213> ORGANISM: Homo sapiens

<400> SEQUENCE: 25

```
gagggaggca cagggcctgg gatcaggagg aatg                                   34
```

<210> SEQ ID NO 26
<211> LENGTH: 34
<212> TYPE: DNA
<213> ORGANISM: Homo sapiens

<400> SEQUENCE: 26

```
cattcctcct gatcccaggc cctgtgcctc cctc                                   34
```

<210> SEQ ID NO 27
<211> LENGTH: 35
<212> TYPE: DNA
<213> ORGANISM: Homo sapiens

<400> SEQUENCE: 27

```
gggaccatat ttggactcgt tgaaccgtcc ctcgc                                  35
```

<210> SEQ ID NO 28
<211> LENGTH: 35
<212> TYPE: DNA
<213> ORGANISM: Homo sapiens

<400> SEQUENCE: 28

```
gcgagggacg gttcaacgag tccaaatatg gtccc                                  35
```

<210> SEQ ID NO 29
<211> LENGTH: 26
<212> TYPE: DNA
<213> ORGANISM: Homo sapiens

<400> SEQUENCE: 29

```
atgcggccgc tcagcgaggg ggcagg                                            26
```

<210> SEQ ID NO 30
<211> LENGTH: 39
<212> TYPE: DNA
<213> ORGANISM: Homo sapiens

<400> SEQUENCE: 30

```
atcgaattcg ccgccaccat gggaaacagc tgttacaac                              39
```

<210> SEQ ID NO 31
<211> LENGTH: 36
<212> TYPE: DNA
<213> ORGANISM: Homo sapiens

<400> SEQUENCE: 31
gataagctta tcgattcacc acatcctcct tcagtt                                    36

<210> SEQ ID NO 32
<211> LENGTH: 43
<212> TYPE: DNA
<213> ORGANISM: Homo sapiens

<400> SEQUENCE: 32
cattgggcta ggcatcttct tcaggagtaa gaggagcagg ctc                            43

<210> SEQ ID NO 33
<211> LENGTH: 47
<212> TYPE: DNA
<213> ORGANISM: Homo sapiens

<400> SEQUENCE: 33
gtttctttct gccccgtttg ccacctccgg agcgataggc tgcgaag                        47

<210> SEQ ID NO 34
<211> LENGTH: 47
<212> TYPE: DNA
<213> ORGANISM: Homo sapiens

<400> SEQUENCE: 34
cttcgcagcc tatcgctccg gaggtggcaa acggggcaga agaaac                         47

<210> SEQ ID NO 35
<211> LENGTH: 38
<212> TYPE: DNA
<213> ORGANISM: Homo sapiens

<400> SEQUENCE: 35
gttgcggccg ctcacagttc acatcctcct tcttcttc                                  38

<210> SEQ ID NO 36
<211> LENGTH: 1644
<212> TYPE: DNA
<213> ORGANISM: Homo sapiens

<400> SEQUENCE: 36
atgctgctgc tggtgaccag cctgctgctg tgcgagctgc ccacccgc ctttctgctg            60 atccctggcc ccgtgccccc tagcaccgcc ctgcgctacc tgatcgagga actggtgaac         120
atcacccaga accagaaagc ccccctgtgc aacggcagca tggtgtggag catcaacctg         180
accgccggca tgtactgtgc cgccctggaa agcctgatca acgtgagcgg ctgcagcgcc         240
atcgagaaaa cccagcggat gctgtccggc ttctgccccc acaaggtgtc cgccggacag         300
ttcagcagcc tgcacgtgcg ggacaccaag atcgaggtgg cccagttcgt gaaggacctg         360
ctgctgcacc tgaagaagct gttccggag ggcggttca acgagagcaa gtacggccct          420
ccctgccccc cttgccctgc ccagagttc ctgggcggac ccagcgtgtt cctgttcccc          480
cccaagccca aggacaccct gatgatcagc cggaccccctg aggtgacctg cgtggtggtg        540
gacgtgagcc aggaagatcc tgaggtccag ttcaattggt acgtggacgg cgtggaagtg        600
cacaacgcca agaccaagcc cagagaggaa cagttcaaca gcacctaccg ggtggtgtct        660
gtgctgaccg tgctgcacca ggactggctg aacggcaaag aatacaagtg caaggtgtcc       720
aacaaggggc tgcccagcag catcgaaaag accatcagca aggccaaggg ccagcctcgc        780
gagccccagg tgtacaccct gcctccctcc caggaagaga tgaccaagaa ccaggtgtcc        840

-continued

```
ctgacctgcc tggtgaaggg cttctacccc agcgacatcg ccgtggagtg ggagagcaac      900
ggccagcctg agaacaacta caagaccacc cctcccgtgc tggacagcga cggcagcttc      960
ttcctgtaca gccggctgac cgtggacaag agccggtggc aggaaggcaa cgtctttagc     1020
tgcagcgtga tgcacgaggc cctgcacaac cactacaccc agaagagcct gagcctgtcc     1080
ctgggcaaga tgttctgggt gctggtggtg gtgggcgggg tgctggcctg ctacagcctg     1140
ctggtgacag tggccttcat catcttttgg gtgcggagca gcggagcag aggcggccac     1200
agcgactaca tgaacatgac ccccagacgg cctggcccca cccggaagca ctaccagccc     1260
tacgccccac ccagggactt tgccgcctac cggtccggcg agggcgggt gaagttcagc      1320
agaagcgccg acgccctgc ctaccagcag ggccagaatc agctgtacaa cgagctgaac     1380
ctgggcagaa gggaagagta cgacgtcctg gataagcgga gaggccggga ccctgagatg     1440
ggcggcaagc ctcggcggaa gaaccccag gaaggcctgt ataacgaact gcagaaagac      1500
aagatggccg aggcctacag cgagatcggc atgaagggcg agcggaggcg gggcaagggc     1560
cacgacggcc tgtatcaggg cctgtccacc gccaccaagg ataccTacga cgccctgcac     1620
atgcaggccc tgccccaag gtga                                             1644
```

<210> SEQ ID NO 37
<211> LENGTH: 1761
<212> TYPE: DNA
<213> ORGANISM: Homo sapiens

<400> SEQUENCE: 37

```
atgcttctcc tggtgacaag ccttctgctc tgtgagttac cacacccagc attcctcctg       60
atcccaggcc ctgtgcctcc ctctacagcc ctcaggagc tcattgagga gctggtcaac      120
atcacccaga accagaaggc tccgctctgc aatggcagca tggtatggag catcaacctg      180
acagctggca tgtactgtgc agccctggaa tccctgatca acgtgtcagg ctgcagtgcc      240
atcgagaaga cccagaggat gctgagcgga ttctgcccgc acaaggtctc agctgggcag      300
ttttccagct gcatgtccg agacaccaaa atcgaggtgg cccagtttgt aaaggacctg      360
ctcttacatt taaagaaact ttttcgcgag ggacggttca acgagtccaa atatggtccc      420
ccatgcccac catgcccagc acctgagttc ctggggggac catcagtctt cctgttcccc      480
ccaaaaccca aggacactct catgatctcc cggacccctg aggtcacgtg cgtggtggtg      540
gacgtgagcc aggaagaccc cgaggtccag ttcaactggt acgtggatgg cgtggaggtg      600
cataatgcca agacaaagcc gcgggaggag cagttcaaca gcacgtaccg tgtggtcagc      660
gtcctcaccg tcctgcacca ggactggctg aacggcaagg agtacaagtg caaggtctcc      720
aacaaaggc tcccgtcctc catcgagaaa accatctcca aagccaaagg cagcccccga      780
gagccacagg tgtacaccct gccccccatcc caggaggaga tgaccaagaa ccaggtcagc      840
ctgacctgcc tggtcaaagg cttctacccc agcgacatcg ccgtggagtg ggagagcaat      900
gggcagccgg agaacaacta caagaccacg cctcccgtgc tggactccga cggctccttc      960
ttcctctaca gcaggctaac cgtggacaag agcaggtggc aggaggggaa tgtcttctca     1020
tgctccgtga tgcatgaggc tctgcacaac cactacacac agaagagcct ctccctgtct     1080
ctgggtaaaa tggccctgat tgtgctgggg gcgtcgccg gcctcctgct tttcattggg     1140
ctaggcatct tcttcaggag taagaggagc aggctcctgc acagtgacta catgaacatg     1200
actccccgcc gcccctgggcc cacccgcaag cattaccagc cctatgcccc accacgcgac     1260
```

| | |
|---|---|
| ttcgcagcct atcgctccgg aggtggcaaa cggggcagaa agaaactcct gtatatattc | 1320 |
| aaacaaccat ttatgagacc agtacaaact actcaagagg aagatggctg tagctgccga | 1380 |
| tttccagaag aagaagaagg aggatgtgaa ctgggaggtg gcagagtgaa gttcagcagg | 1440 |
| agcgcagacg cccccgcgta ccagcagggc cagaaccagc tctataacga gctcaatcta | 1500 |
| ggacgaagag aggagtacga tgttttggac aagagacgtg gccgggaccc tgagatgggg | 1560 |
| ggaaagccga aaggaagaa ccctcaggaa ggcctgtaca atgaactgca gaaagataag | 1620 |
| atggcggagg cctacagtga gattgggatg aaaggcgagc gccggagggg caaggggcac | 1680 |
| gatggccttt accagggtct cagtacagcc accaaggaca cctacgacgc ccttcacatg | 1740 |
| caggccctgc cccctcgctg a | 1761 |

<210> SEQ ID NO 38
<211> LENGTH: 1740
<212> TYPE: DNA
<213> ORGANISM: Homo sapiens

<400> SEQUENCE: 38

| | |
|---|---|
| atgcttctcc tggtgacaag ccttctgctc tgtgagttac cacacccagc attcctcctg | 60 |
| atcccaggcc ctgtgcctcc ctctacagcc ctcaggtacc tcattgagga gctggtcaac | 120 |
| atcacccaga accagaaggc tccgctctgc aatggcagca tggtatggag catcaacctg | 180 |
| acagctggca tgtactgtgc agccctggaa tccctgatca acgtgtcagg ctgcagtgcc | 240 |
| atcgagaaga cccagaggat gctgagcgga ttctgcccgc acaaggtctc agctgggcag | 300 |
| ttttccagct tgcatgtccg agacaccaaa atcgaggtgg cccagtttgt aaaggacctg | 360 |
| ctcttacatt taaagaaact ttttcgcgag ggacggttca acgagtccaa atatggtccc | 420 |
| ccatgcccac catgcccagc acctgagttc ctgggggac catcagtctt cctgttcccc | 480 |
| ccaaaaccca aggacactct catgatctcc cggacccctg aggtcacgtg cgtggtggtg | 540 |
| gacgtgagcc aggaagaccc cgaggtccag ttcaactggt acgtggatgg cgtggaggtg | 600 |
| cataatgcca agacaaagcc gcgggaggag cagttcaaca gcacgtaccg tgtggtcagc | 660 |
| gtcctcaccg tcctgcacca ggactggctg aacggcaagg agtacaagtg caaggtctcc | 720 |
| aacaaaggcc tcccgtcctc catcgagaaa accatctcca aagccaaagg gcagccccga | 780 |
| gagccacagg tgtacaccct gcccccatcc caggaggaga tgaccaagaa ccaggtcagc | 840 |
| ctgacctgcc tggtcaaagg cttctacccc agcgacatcg ccgtggagtg ggagagcaat | 900 |
| gggcagccgg agaacaacta caagaccacg cctcccgtgc tggactccga cggctccttc | 960 |
| ttcctctaca gcaggctaac cgtggacaag agcaggtggc aggaggggaa tgtcttctca | 1020 |
| tgctccgtga tgcatgaggc tctgcacaac cactacacac agaagagcct ctccctgtcc | 1080 |
| ctaggtaaat ttgggtgct ggtggtggtt ggtggagtcc tggcttgcta tagcttgcta | 1140 |
| gtaacagtgg ccttattat tttctgggtg aggagtaaga ggagcaggct cctgcacagt | 1200 |
| gactacatga acatgactcc ccgccgcccc gggcccaccc gcaagcatta ccagccctat | 1260 |
| gccccaccac gcgacttcgc agcctatcgc tccagggacc agaggctgcc cccgatgcc | 1320 |
| cacaagcccc tgggggagg cagtttccgg acccccatcc aagaggagca ggccgacgcc | 1380 |
| cactccaccc tggccaagat cagagtgaag ttcagcagga gcgcagacgc ccccgcgtac | 1440 |
| cagcagggcc agaaccagct ctataacgag ctcaatctag gacgaagaga ggagtacgat | 1500 |
| gttttggaca gagacgtgg ccgggaccct gagatggggg gaaagccgag aaggaagaac | 1560 |
| cctcaggaag gcctgtacaa tgaactgcag aaagataaga tggcggaggc ctacagtgag | 1620 |

```
<210> SEQ ID NO 39
<211> LENGTH: 1779
<212> TYPE: DNA
<213> ORGANISM: Homo sapiens

<400> SEQUENCE: 39
atgcttctcc tggtgacaag ccttctgctc tgtgagttac cacacccagc attcctcctg      60
atcccaggcc ctgtgcctcc ctctacagcc ctcaggtacc tcattgagga gctggtcaac     120
atcacccaga accagaaggc tccgctctgc aatggcagca tggtatggag catcaacctg     180
acagctggca tgtactgtgc agccctggaa tccctgatca acgtgtcagg ctgcagtgcc     240
atcgagaaga cccagaggat gctgagcgga ttctgcccgc acaaggtctc agctgggcag     300
ttttccagct tgcatgtccg agacaccaaa atcgaggtgg cccagtttgt aaaggacctg     360
ctcttacatt taaagaaact ttttcgcgag ggacggttca acgagtccaa atatggtccc     420
ccatgcccac catgcccagc acctgagttc ctgggggac catcagtctt cctgttcccc     480
ccaaaaccca aggacactct catgatctcc cggacccctg aggtcacgtg cgtggtggtg     540
gacgtgagcc aggaagaccc cgaggtccag ttcaactggt acgtggatgg cgtggaggtg     600
cataatgcca agacaaagcc gcgggaggag cagttcaaca gcacgtaccg tgtggtcagc     660
gtcctcaccg tcctgcacca ggactggctg aacggcaagg agtacaagtg caaggtctcc     720
aacaaaggcc tcccgtcctc catcgagaaa accatctcca agccaaagg cagccccga     780
gagccacagg tgtacaccct gcccccatcc caggaggaga tgaccaagaa ccaggtcagc     840
ctgacctgcc tggtcaaagg cttctacccc agcgacatcg ccgtggagtg ggagagcaat     900
gggcagccgg agaacaacta caagaccacg cctcccgtgc tggactccga cggctccttc     960
ttcctctaca gcaggctaac cgtggacaag agcaggtggc aggaggggaa tgtcttctca    1020
tgctccgtga tgcatgaggc tctgcacaac cactacacac agaagagcct ctccctgtcc    1080
ctaggtaaaa tgttttgggt gctggtggtg gttggtggag tcctggcttg ctatagcttg    1140
ctagtaacag tggcctttat tattttctgg gtgaggagta agaggagcag ggcggacac    1200
agtgactaca tgaacatgac tccccgccgc cctgggccca cccgcaagca ttaccagccc    1260
tatgccccac cacgcgactt cgcagcctat cgctccggag gtggcaaacg gggcagaaag    1320
aaaactcctgt atatattcaa caaccatttt atgagaccag tacaaactac tcaagaggaa    1380
gatggctgta gctgccgatt tccagaagaa gaagaaggag gatgtgaact gggaggtggc    1440
agagtgaagt tcagcaggag cgcagacgcc cccgcgtacc agcagggcca gaaccagctc    1500
tataacgagc tcaatctagg acgaagagag gagtacgatg ttttggacaa gagacgtggc    1560
cgggaccctg agatgggggg aaagccgaga aggaagaacc tcaggaagg cctgtacaat    1620
gaactgcaga aagataagat ggcggaggcc tacagtgaga ttgggatgaa aggcgagcgc    1680
cggagggggca aggggcacga tggcctttac cagggtctca gtacagccac caaggacacc    1740
tacgacgccc ttcacatgca ggccctgccc cctcgctga                            1779

<210> SEQ ID NO 40
<211> LENGTH: 1779
<212> TYPE: DNA
<213> ORGANISM: Homo sapiens
```

<400> SEQUENCE: 40

```
atgcttctcc tggtgacaag ccttctgctc tgtgagttac cacacccagc attcctcctg      60
atcccaggcc ctgtgcctcc ctctacagcc ctcaggtacc tcattgagga gctggtcaac     120
atcacccaga accagaaggc tccgctctgc aatggcagca tggtatggag catcaacctg     180
acagctggca tgtactgtgc agccctggaa tccctgatca acgtgtcagg ctgcagtgcc     240
atcgagaaga cccagaggat gctgagcgga ttctgcccgc acaaggtctc agctgggcag     300
ttttccagct tgcatgtccg agacaccaaa atcgaggtgg cccagtttgt aaaggacctg     360
ctcttacatt taaagaaact ttttcgcgag gacggttca acgagtccaa atatggtccc      420
ccatgcccac catgcccagc acctgagttc ctgggggac catcagtctt cctgttcccc      480
ccaaaaccca aggacactct catgatctcc cggacccctg aggtcacgtg cgtggtggtg     540
gacgtgagcc aggaagaccc cgaggtccag ttcaactggt acgtggatgg cgtggaggtg     600
cataatgcca agacaaagcc gcgggaggag cagttcaaca gcacgtaccg tgtggtcagc     660
gtcctcaccg tcctgcacca ggactggctg aacggcaagg agtacaagtg caaggtctcc     720
aacaaaggcc tcccgtcctc catcgagaaa accatctcca aagccaaagg cagccccga     780
gagccacagg tgtacaccct gccccatcc caggaggaga tgaccaagaa ccaggtcagc     840
ctgacctgcc tggtcaaagg cttctacccc agcgacatcg ccgtggagtg ggagagcaat     900
gggcagccgg agaacaacta caagaccacg cctcccgtgc tggactccga cggctccttc     960
ttcctctaca gcaggctaac cgtggacaag agcaggtggc aggaggggaa tgtcttctca    1020
tgctccgtga tgcatgaggc tctgcacaac cactacacac agaagagcct ctccctgtcc    1080
ctaggtaaaa tgttttgggt gctggtggtg gttggtggag tcctggcttg ctatagcttg    1140
ctagtaacag tggccttat tattttctgg gtgaggagta agaggagcag gggcggacac    1200
agtgactaca tgaacatgac tccccgccgc cctgggccca cccgcaagca ttaccagccc    1260
tatgccccac cacgcgactt cgcagccgga ggtggcggag tggcaaacg gggcagaaag    1320
aaactcctgt atatattcaa acaaccattt atgagaccag tacaaactac tcaagaggaa    1380
gatggctgta gctgccgatt ccagaagaa gaagaaggag gatgtgaact gggaggtggc    1440
agagtgaagt tcagcaggag cgcagacgcc cccgcgtacc agcagggcca gaaccagctc    1500
tataacgagc tcaatctagg acgaagagag gagtacgatg ttttggacaa gagacgtggc    1560
cgggaccctg agatgggggg aaagccgaga aggaagaacc ctcaggaagg cctgtacaat    1620
gaactgcaga agataagat ggcggaggcc tacagtgaga ttgggatgaa aggcgagcgc    1680
cggaggggca aggggcacga tggcctttac cagggtctca gtacagccac caaggacacc    1740
tacgacgccc ttcacatgca ggccctgccc cctcgctga                           1779
```

<210> SEQ ID NO 41
<211> LENGTH: 544
<212> TYPE: DNA
<213> ORGANISM: Homo sapiens

<400> SEQUENCE: 41

```
ggatctgcga tcgctccggt gcccgtcagt gggcagagcg cacatcgccc acagtccccg     60
agaagttggg gggaggggtc ggcaattgaa ccggtgccta gagaaggtgg cgcggggtaa   120
actgggaaag tgatgtcgtg tactggctcc gccttttttcc cgagggtggg ggagaaccgt   180
atataagtgc agtagtcgcc gtgaacgttc ttttttcgcaa cgggtttgcc gccagaacac   240
agctgaagct tcgaggggct cgcatctctc cttcacgcgc ccgccgccct acctgaggcc   300
```

```
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctac                                                                544
```

<210> SEQ ID NO 42
<211> LENGTH: 1494
<212> TYPE: DNA
<213> ORGANISM: Homo sapiens

<400> SEQUENCE: 42

```
atgcttctcc tggtgacaag ccttctgctc tgtgagttac cacacccagc attcctcctg     60
atcccaggcc ctgtgcctcc ctctacagcc ctcaggtacc tcattgagga gctggtcaac    120
atcacccaga accagaaggc tccgctctgc aatggcagca tggtatggag catcaacctg    180
acagctggca tgtactgtgc agccctggaa tccctgatca acgtgtcagg ctgcagtgcc    240
atcgagaaga cccagaggat gctgagcgga ttctgcccgc acaaggtctc agctgggcag    300
ttttccagct tgcatgtccg agacaccaaa atcgaggtgg cccagtttgt aaaggacctg    360
ctcttacatt taaagaaact ttttcgcgag gacggttca acgagtccaa atatggtccc    420
ccatgcccac catgcccagc acctgagttc ctgggggac catcagtctt cctgttcccc    480
ccaaaaccca aggacactct catgatctcc cggacccctg aggtcacgtg cgtggtggtg    540
gacgtgagcc aggaagaccc cgaggtccag ttcaactggt acgtggatgg cgtggaggtg    600
cataatgcca agacaaagcc gcgggaggag cagttcaaca gcacgtaccg tgtggtcagc    660
gtcctcaccg tcctgcacca ggactggctg aacggcaagg agtacaagtg caaggtctcc    720
aacaaaggcc tcccgtcctc catcgagaaa accatctcca aagccaaagg gcagccccga    780
gagccacagg tgtacaccct gccccccatcc caggaggaga tgaccaagaa ccaggtcagc    840
ctgacctgcc tggtcaaagg cttctacccc agcgacatcg ccgtggagtg ggagagcaat    900
gggcagccgg agaacaacta caagaccacg cctcccgtgc tggactccga cggctccttc    960
ttcctctaca gcaggctaac cgtggacaag agcaggtggc aggagggaa tgtcttctca   1020 tgctccgtga tgcatgaggc tctgcacaac cactacacac agaagagcct ctccctgtcc   1080
ctaggtaaaa tggccctgat tgtgctgggg ggcgtcgccg gcctcctgct tttcattggg   1140
ctaggcatct tcttcagagt gaagttcagc aggagcgcac acgccccgc gtaccagcag   1200 ggccagaacc agctctataa cgagctcaat ctaggacgaa gagaggagta cgatgttttg   1260
gacaagagac gtggccggga ccctgagatg ggggaaagc cgagaaggaa gaaccctcag   1320
gaaggcctgt acaatgaact gcagaaagat aagatggcgg aggcctacag tgagattggg   1380
atgaaaggcg agcgcggag gggcaagggg cacgatggcc tttaccaggg tctcagtaca   1440
gccaccaagg acacctacga cgcccttcac atgcaggccc tgccccctcg ctga         1494
```

<210> SEQ ID NO 43
<211> LENGTH: 268
<212> TYPE: DNA
<213> ORGANISM: Homo sapiens

<400> SEQUENCE: 43

```
gacatgataa gatacattga tgagtttgga caaaccacaa ctagaatgca gtgaaaaaaa     60
```

| | |
|---|---|
| tgctttattt gtgaaatttg tgatgctatt gctttatttg tgaaatttgt gatgctattg | 120 |
| ctttatttgt aaccattata agctgcaata aacaagttaa caacaacaat tgcattcatt | 180 |
| ttatgtttca ggttcagggg gaggtgtggg aggttttta aagcaagtaa aacctctaca | 240 |
| aatgtggtag atccatttaa atgttagc | 268 |

<210> SEQ ID NO 44
<211> LENGTH: 748
<212> TYPE: DNA
<213> ORGANISM: Homo sapiens

<400> SEQUENCE: 44

| | |
|---|---|
| gaagaacatg tgagcaaaag ccagcaaaa ggccaggaac cgtaaaaagg ccgcgttgct | 60 |
| ggcgttttc cataggctcc gccccctga cgagcatcac aaaaatcgac gctcaagtca | 120 |
| gaggtggcga aacccgacag gactataaag ataccaggcg tttccccctg gaagctccct | 180 |
| cgtgcgctct cctgttccga ccctgccgct taccggatac ctgtccgcct ttctcccttc | 240 |
| gggaagcgtg gcgctttctc aatgctcacg ctgtaggtat ctcagttcgg tgtaggtcgt | 300 |
| tcgctccaag ctgggctgtg tgcacgaacc ccccgttcag cccgaccgct gcgccttatc | 360 |
| cggtaactat cgtcttgagt ccaacccggt aagacacgac ttatcgccac tggcagcagc | 420 |
| cactggtaac aggattagca gagcgaggta tgtaggcggt gctacagagt tcttgaagtg | 480 |
| gtggcctaac tacggctaca ctagaagaac agtatttggt atctgcgctc tgctgaagcc | 540 |
| agttaccttc ggaaaaagag ttggtagctc ttgatccggc aaacaaacca ccgctggtag | 600 |
| cggtggtttt tttgtttgca agcagcagat tacgcgcaga aaaaaaggat ctcaagaaga | 660 |
| tcctttgatc ttttctacgg ggtctgacgc tcagtggaac gaaaactcac gttaagggat | 720 |
| tttggtcatg gctagttaat taagctgc | 748 |

<210> SEQ ID NO 45
<211> LENGTH: 187
<212> TYPE: DNA
<213> ORGANISM: Homo sapiens

<400> SEQUENCE: 45

| | |
|---|---|
| aataaacaat cattattttc attggatctg tgtgttggtt ttttgtgtgg gcttgggga | 60 |
| gggggaggcc agaatgactc caagagctac aggaaggcag gtcagagacc ccactggaca | 120 |
| aacagtggct ggactctgca ccataacaca caatcaacag gggagtgagc tggatcgagc | 180 |
| tagagtc | 187 |

<210> SEQ ID NO 46
<211> LENGTH: 811
<212> TYPE: DNA
<213> ORGANISM: Homo sapiens

<400> SEQUENCE: 46

| | |
|---|---|
| cgttacataa cttacggtaa atggcccgcc tggctgaccg cccaacgacc cccgcccatt | 60 |
| gacgtcaata atgacgtatg ttcccatagt aacgccaata gggactttcc attgacgtca | 120 |
| atgggtggag tatttacggt aaactgccca cttggcagta catcaagtgt atcatatgcc | 180 |
| aagtacgccc cctattgacg tcaatgacgg taaatggccc gcctggcatt atgcccagta | 240 |
| catgacctta tgggactttc ctacttggca gtacatctac gtattagtca tcgctattac | 300 |
| catggtgatg cggttttggc agtacatcaa tgggcgtgga tagcggtttg actcacgggg | 360 |
| atttccaagt ctccaccccca ttgacgtcaa tgggagtttg ttttggcacc aaaatcaacg | 420 |

| | |
|---|---|
| ggactttcca aaatgtcgta acaactccgc cccattgacg caaatgggcg gtaggcgtgt | 480 |
| acggtgggag gtctatataa gcagagctcg tttagtgaac cgtcagatcg cctggagacg | 540 |
| ccatccacgc tgttttgacc tccatagaag acaccgggac cgatccagcc tccgcggccg | 600 |
| ggaacggtgc attggaacgc ggattccccg tgccaagagt gacgtaagta ccgcctatag | 660 |
| agtctatagg cccacctagt tgtgaccggc gcctagtgtt gacaattaat catcggcata | 720 |
| gtataatacg actcactata ggagggccac catgtcgact actaaccttc ttctctttcc | 780 |
| tacagctgag atcaccggta ggagggccat c | 811 |

<210> SEQ ID NO 47
<211> LENGTH: 2076
<212> TYPE: DNA
<213> ORGANISM: Homo sapiens

<400> SEQUENCE: 47

| | |
|---|---|
| atgaaaaagc ctgaactcac cgcgacgtct gtcgcgaagt ttctgatcga aaagttcgac | 60 |
| agcgtctccg acctgatgca gctctcggag ggcgaagaat ctcgtgcttt cagcttcgat | 120 |
| gtaggagggc gtggatatgt cctgcgggta aatagctgcg ccgatggttt ctacaaagat | 180 |
| cgttatgttt atcggcactt tgcatcggcc gcgctcccga ttccggaagt gcttgacatt | 240 |
| ggggaattca gcgagagcct gacctattgc atctcccgcc gtgcacaggg tgtcacgttg | 300 |
| caagacctgc ctgaaaccga actgcccgct gttctgcaac ccgtcgcgga gctcatggat | 360 |
| gcgatcgctg cggccgatct tagccagacg agcgggttcg gcccattcgg accgcaagga | 420 |
| atcggtcaat acactacatg gcgtgatttc atatgcgcga ttgctgatcc ccatgtgtat | 480 |
| cactggcaaa ctgtgatgga cgacaccgtc agtgcgtccg tcgcgcaggc tctcgatgag | 540 |
| ctgatgcttt gggccgagga ctgccccgaa gtccggcacc tcgtgcacgc ggatttcggc | 600 |
| tccaacaatg tcctgacgga caatggccgc ataacagcgg tcattgactg gagcgaggcg | 660 |
| atgttcgggg attcccaata cgaggtcgcc aacatcttct tctggaggcc gtggttggct | 720 |
| tgtatggagc agcagacgcg ctacttcgag cggaggcatc cggagcttgc aggatcgccg | 780 |
| cggctccggg cgtatatgct ccgcattggt cttgaccaac tctatcagag cttggttgac | 840 |
| ggcaatttcg atgatgcagc ttgggcgcag ggtcgatgcg acgcaatcgt ccgatccgga | 900 |
| gccgggactg tcgggcgtac acaaatcgcc cgcagaagcg cggccgtctg gaccgatggc | 960 |
| tgtgtagaag tcgcgtctgc gttcgaccag gctgcgcgtt ctcgcggcca tagcaaccga | 1020 |
| cgtacggcgt tgcgccctcg ccggcagcaa gaagccacgg aagtccgccc ggagcagaaa | 1080 |
| atgcccacgc tactgcgggt ttatatagac ggtccccacg gatgggggaa aaccaccacc | 1140 |
| acgcaactgc tggtggccct gggttcgcgc gacgatatcg tctacgtacc cgagccgatg | 1200 |
| acttactggc gggtgctggg ggcttccgag acaatcgcga acatctacac cacacaacac | 1260 |
| cgcctcgacc agggtgagat atcggccggg gacgcggcgg tggtaatgac aagcgcccag | 1320 |
| ataacaatgg gcatgcctta tgccgtgacc gacgccgttc tggctcctca tatcggggggg | 1380 |
| gaggctggga gctcacatgc cccgccccg gccctcaccc tcatcttcga ccgccatccc | 1440 |
| atcgccgccc tcctgtgcta cccggccgcg cggtacctta tgggcagcat gacccccag | 1500 |
| gccgtgctgg cgttcgtggc cctcatcccg ccgaccttgc ccggcaccaa catcgtgctt | 1560 |
| ggggcccttc cggaggacag acacatcgac cgcctggcca aacgccagcg ccccggcgag | 1620 |
| cggctggacc tggctatgct ggctgcgatt cgccgcgttt acgggctact tgccaatacg | 1680 |

```
gtgcggtatc tgcagtgcgg cgggtcgtgg cggaggact  ggggacagct ttcggggacg    1740
gccgtgccgc cccagggtgc cgagcccag  agcaacgcgg gcccacgacc ccatatcggg    1800
gacacgttat ttaccctgtt tcgggccccc gagttgctgg ccccaacgg  cgacctgtat    1860 aacgtgtttg cctgggcctt ggacgtcttg gccaaacgcc tccgttccat gcacgtcttt    1920
atcctggatt acgaccaatc gcccgccggc tgccgggacg ccctgctgca acttacctcc    1980
gggatggtcc agaccacgt  caccaccccc ggctccatac cgacgatatg cgacctggcg    2040
cgcacgtttg cccgggagat ggggaggct  aactga                              2076

<210> SEQ ID NO 48
<211> LENGTH: 299
<212> TYPE: DNA
<213> ORGANISM: Homo sapiens

<400> SEQUENCE: 48
gtcgagaatt cgctagaggg ccctattcta tagtgtcacc taaatgctag agctcgctga    60
tcagcctcga ctgtgccttc tagttgccag ccatctgttg tttgcccctc ccccgtgcct    120
tccttgaccc tggaaggtgc cactcccact gtcctttcct aataaaatga ggaaattgca    180
tcgcattgtc tgagtaggtg tcattctatt ctggggggtg gggtggggca ggacagcaag    240
ggggaggatt gggaagacaa tagcaggcat gcgcagggcc caattgctcg agcggccgc    299

<210> SEQ ID NO 49
<211> LENGTH: 75
<212> TYPE: DNA
<213> ORGANISM: Artificial Sequence
<220> FEATURE:
<223> OTHER INFORMATION: oligonucleotide with homology to foot and mouth
      disease gene

<400> SEQUENCE: 49
tctagaggag catgccagct gttgaatttt gaccttctta agcttgcggg agacgtcgag    60
tccaaccctg ggccc                                                    75

<210> SEQ ID NO 50
<211> LENGTH: 21
<212> TYPE: DNA
<213> ORGANISM: Homo sapiens

<400> SEQUENCE: 50
caagaatccc aaactcacca g                                              21

<210> SEQ ID NO 51
<211> LENGTH: 23
<212> TYPE: DNA
<213> ORGANISM: Homo sapiens

<400> SEQUENCE: 51
cgttgatatt gctgattaag tcc                                            23

<210> SEQ ID NO 52
<211> LENGTH: 24
<212> TYPE: DNA
<213> ORGANISM: Homo sapiens

<400> SEQUENCE: 52
atcccagtaa tggttgtcct gcct                                           24

<210> SEQ ID NO 53
```

```
<211> LENGTH: 24
<212> TYPE: DNA
<213> ORGANISM: Homo sapiens

<400> SEQUENCE: 53
tcttgcttag gttggctgcc tagt                                          24

<210> SEQ ID NO 54
<211> LENGTH: 586
<212> TYPE: PRT
<213> ORGANISM: Homo sapiens

<400> SEQUENCE: 54

Met Leu Leu Val Thr Ser Leu Leu Cys Glu Leu Pro His Pro
1               5                   10                  15

Ala Phe Leu Leu Ile Pro Gly Pro Val Pro Pro Ser Thr Ala Leu Arg
            20                  25                  30

Glu Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe Asn Glu Ser Lys Tyr Gly Pro Pro Cys Pro Pro
    130                 135                 140

Cys Pro Ala Pro Glu Phe Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335
```

-continued

```
Asn Val Phe Ser Cys Ser Val Met His Glu Ala Leu His Asn His Tyr
            340                 345                 350
Thr Gln Lys Ser Leu Ser Leu Ser Leu Gly Lys Met Ala Leu Ile Val
            355                 360                 365
Leu Gly Gly Val Ala Gly Leu Leu Leu Phe Ile Gly Leu Gly Ile Phe
            370                 375                 380
Phe Arg Ser Lys Arg Ser Arg Leu Leu His Ser Asp Tyr Met Asn Met
385                 390                 395                 400
Thr Pro Arg Arg Pro Gly Pro Thr Arg Lys His Tyr Gln Pro Tyr Ala
            405                 410                 415
Pro Pro Arg Asp Phe Ala Ala Tyr Arg Ser Gly Gly Gly Lys Arg Gly
            420                 425                 430
Arg Lys Lys Leu Leu Tyr Ile Phe Lys Gln Pro Phe Met Arg Pro Val
            435                 440                 445
Gln Thr Thr Gln Glu Glu Asp Gly Cys Ser Cys Arg Phe Pro Glu Glu
            450                 455                 460
Glu Glu Gly Gly Cys Glu Leu Gly Gly Gly Arg Val Lys Phe Ser Arg
465                 470                 475                 480
Ser Ala Asp Ala Pro Ala Tyr Gln Gln Gly Gln Asn Gln Leu Tyr Asn
            485                 490                 495
Glu Leu Asn Leu Gly Arg Arg Glu Glu Tyr Asp Val Leu Asp Lys Arg
            500                 505                 510
Arg Gly Arg Asp Pro Glu Met Gly Gly Lys Pro Arg Arg Lys Asn Pro
            515                 520                 525
Gln Glu Gly Leu Tyr Asn Glu Leu Gln Lys Asp Lys Met Ala Glu Ala
            530                 535                 540
Tyr Ser Glu Ile Gly Met Lys Gly Glu Arg Arg Arg Gly Lys Gly His
545                 550                 555                 560
Asp Gly Leu Tyr Gln Gly Leu Ser Thr Ala Thr Lys Asp Thr Tyr Asp
            565                 570                 575
Ala Leu His Met Gln Ala Leu Pro Pro Arg
            580                 585
```